US012767963B2

(12) United States Patent
Greenhalgh et al.

(10) Patent No.: US 12,767,963 B2
(45) Date of Patent: Oct. 20, 2026

(54) GENETICALLY ENGINEERED PEPTIDE SUPERSTRUCTURE AND MICROBE FOR PRODUCTION OF ISOPRENE AND METHOD OF PRODUCTION THEREOF

(71) Applicant: CycloKinetics, Inc., Salt Lake City, UT (US)

(72) Inventors: Jonathan Cloyd Greenhalgh, Salt Lake City, UT (US); Robert Andrew Price, Salt Lake City, UT (US)

(73) Assignee: CycloKinetics, Inc., Salt Lake City, UT (US)

( * ) Notice: Subject to any disclaimer, the term of this patent is extended or adjusted under 35 U.S.C. 154(b) by 0 days.

(21) Appl. No.: 19/374,049

(22) Filed: Oct. 30, 2025

(65) Prior Publication Data

US 2026/0117263 A1 Apr. 30, 2026

Related U.S. Application Data

(60) Provisional application No. 63/713,890, filed on Oct. 30, 2024.

(51) Int. Cl.
*C12P 5/00* (2006.01)
*C12N 9/88* (2006.01)
*C12N 9/90* (2006.01)

(52) U.S. Cl.
CPC ................ *C12P 5/007* (2013.01); *C12N 9/88* (2013.01); *C12N 9/90* (2013.01); *C12Y 402/03027* (2013.01); *C12Y 503/03002* (2013.01)

(58) Field of Classification Search
CPC .. C12P 5/007; C12P 5/00; C12P 11/00; C07C 11/18
See application file for complete search history.

(56) References Cited

U.S. PATENT DOCUMENTS

| | | | | |
|---|---|---|---|---|
| 9,121,038 | B2 | 9/2015 | Beck et al. | |
| 10,480,015 | B2 | 11/2019 | Kumaran et al. | |
| 2010/0311065 | A1 | 12/2010 | Ubersax et al. | |
| 2011/0045563 | A1 | 2/2011 | Melis | |
| 2018/0094282 | A1* | 4/2018 | Cartman ................ | C07C 11/12 |

FOREIGN PATENT DOCUMENTS

| | | | |
|---|---|---|---|
| CN | 111363709 | A | 5/2023 |
| CN | 117965414 | B | 6/2024 |
| JP | 2022150327 | A | 10/2022 |

OTHER PUBLICATIONS

Devos et al., (Proteins: Structure, Function and Genetics, 2000, vol. 41: 98-107). (Year: 2000).*

Whisstock et al., (Quarterly Reviews of Biophysics 2003, vol. 36 (3): 307-340). (Year: 2003).*

Witkowski et al., (Biochemistry 38:11643-11650, 1999). (Year: 1999).*

Chen, X.; Zaro, J. L.; Shen, W.-C. "Fusion Protein Linkers: Property, Design and Functionality," Advanced Drug Delivery Reviews, vol. 65, No. 10, pp. 1357-1369, Oct. 2013, Elsevier B.V., Amsterdam, The Netherlands.

Gao, X.; Gao, F.; Liu, D.; Zhang, H.; Nie, X.; Yang, C. "Engineering the Methylerythritol Phosphate Pathway in Cyanobacteria for Photosynthetic Isoprene Production from $CO_2$," Energy & Environmental Science, vol. 9, pp. 1400-1411, 2016, Royal Society of Chemistry, Cambridge, United Kingdom.

Yu, K.; Liu, C.; Kim, B.-G .; Lee, D.-Y. "Synthetic Fusion Protein Design and Applications," Biotechnology Advances, vol. 33, No. 1, pp. 155-164, Jan. 2015, Elsevier Inc., Amsterdam, The Netherlands.

Whited, G. M.; Feher, F. J.; Benko, D. A.; Cervin, M. A.; Chotani, G. K.; Mcauliffe, J. C.; Laduca, R. J.; Ben-Shoshan, E. A.; Sanford, K. J. "Technology Update: Development of a Gas-Phase Bioprocess for Isoprene- Monomer Production Using Metabolic Pathway Engineering," Industrial Biotechnology, vol. 6, No. 3, pp. 152-163, Jun. 2010, Mary Ann Liebert Inc., New Rochelle, United States.

Gossen, M.; Bujard, H. "Tight Control of Gene Expression in Mammalian Cells by Tetracycline-Responsive Promoters," Proceedings of the National Academy of Sciences of the United States of America, vol. 89, No. 12, pp. 5547-5551, Jun. 1992, National Academy of Sciences, Washington, D.C., United States.

Urlinger, S.; Baron, U.; Thellmann, M.; Hasan, M.T.; Bujard, H.; Hillen, W. "Exploring the Sequence Space for Tetracycline-Dependent Transcriptional Activators: Novel Mutations Yield Expanded Range and Sensitivity," Proceedings of the National Academy of Sciences of the United States of America, vol. 97, No. 14, pp. 7963-7968, Jul. 2000, National Academy of Sciences, Washington, D.C., United States.

Zhou, X.; Vink, M.; Klaver, B.; Berkhout, B.; Das, A.T. "Optimization of the Tet-On System for Regulated Gene Expression Through Viral Evolution," Gene Therapy, vol. 13, No. 19, pp. 1382-1390, May 2006, Nature Publishing Group, London, United Kingdom.

International Search Report; PCT/US2025/053306; Date: Feb. 23, 2026; By: Authorized Officer Taina Matos.

* cited by examiner

*Primary Examiner* — Tekchand Saidha
(74) *Attorney, Agent, or Firm* — CALDWELL LLC

(57) ABSTRACT

A genetically engineered microbe capable of producing isoprene, wherein the genetically engineered microbe including a heterologous nucleic acid construct encoding at least a portion of a peptide superstructure; the peptide superstructure including a first portion including a first binding site configured to catalyze a first chemical reaction, wherein the first reaction converts a substrate to an intermediate; and a second portion including a second binding site configured to catalyze a second chemical reaction, wherein the second binding site is located in proximity to the first binding site and the second chemical reaction converts the intermediate to isoprene.

5 Claims, 14 Drawing Sheets

Specification includes a Sequence Listing.

IDI_Linker3_IspS

1200A

1200B

GENETICALLY ENGINEERED PEPTIDE SUPERSTRUCTURE AND MICROBE FOR PRODUCTION OF ISOPRENE AND METHOD OF PRODUCTION THEREOF

REFERENCE TO RELATED APPLICATIONS

This application claims the benefit of priority of U.S. Provisional Application Ser. No. 63/713,890, filed on Oct. 30, 2024, and entitled "GENETICALLY ENGINEERED PEPTIDE SUPERSTRUCTURE AND MICROBE FOR PRODUCTION OF ISOPRENE AND METHOD OF PRODUCTION THEREOF," which is incorporated by reference herein in its entirety.

FIELD OF THE INVENTION

The present invention generally relates to the field of metabolic engineering. In particular, the present invention is directed to a genetically engineered peptide superstructure and microbe for production of isoprene.

REFERENCE TO SEQUENCE LISTING

This specification includes a sequence listing submitted herewith, which includes the file entitled 1656-002USU1.xml having the following size: 113,663 bytes which was created Oct. 20, 2025, the contents of which are incorporated by reference herein.

BACKGROUND

Isoprene is an important commodity chemical used in a wide range of industrial applications, from the production of synthetic rubber for tires and coatings to uses in adhesives and development of specialty elastomers. Current production of isoprene is derived mostly from unsustainable petrochemical sources and often involves resource-intensive methods that require extensive land use, high temperature, and/or use of precious metals. Biosynthesis of isoprene, while showing some progress, is often plagued by competing side reactions that limit the yield of isoprene.

SUMMARY OF THE DISCLOSURE

In an aspect, a genetically engineered microbe capable of producing isoprene, wherein the genetically engineered microbe including a heterologous nucleic acid construct encoding at least a portion of a peptide superstructure; the peptide superstructure including a first portion including a first binding site configured to catalyze a first chemical reaction, wherein the first reaction converts a substrate to an intermediate; and a second portion including a second binding site configured to catalyze a second chemical reaction, wherein the second binding site is located in proximity to the first binding site and the second chemical reaction converts the intermediate to isoprene.

In another aspect, a genetically engineered peptide superstructure for production of isoprene, the superstructure including a first portion including at least a functional fragment of isoprene synthase (IspS) configured to catalyze a first chemical reaction, and a second portion including at least a functional fragment of isopentenyl diphosphate (IPP) isomerase configured to catalyze a second chemical reaction, wherein the second chemical reaction converts a substrate to an intermediate, wherein the second portion is covalently linked to the first portion through a linker, and wherein the intermediate is converted into isoprene by the first chemical reaction.

In another aspect, a genetically engineered peptide superstructure for production of isoprene, the superstructure including a first portion including at least a functional fragment of isopentenyl diphosphate (IPP) isomerase configured to catalyze a first chemical reaction, wherein the first chemical reaction converts a substrate to an intermediate, and a second portion including at least a functional fragment of isoprene synthase (IspS) configured to catalyze a second chemical reaction, wherein the second portion is covalently linked to the first portion through a linker, and wherein the intermediate is converted into isoprene by the second chemical reaction.

In another aspect, a method of producing isoprene using a genetically engineered peptide superstructure, the method including culturing a genetically engineered microbe under suitable conditions, wherein the genetically engineered microbe includes a heterologous nucleic acid construct encoding at least a portion of a peptide superstructure, and the superstructure includes a first portion including a first binding site and a second portion including a second binding site, the second portion being covalently linked to the first portion through a linker; and providing a substrate to the cultured genetically engineered microbe, wherein the first binding site is configured to bind to the substrate and catalyze a first chemical reaction that converts the substrate to an intermediate, and the second binding site is configured to catalyze a second chemical reaction that converts the intermediate to isoprene.

These and other aspects and features of nonlimiting embodiments of the present invention will become apparent to those skilled in the art upon review of the following description of specific nonlimiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

Figure 1:
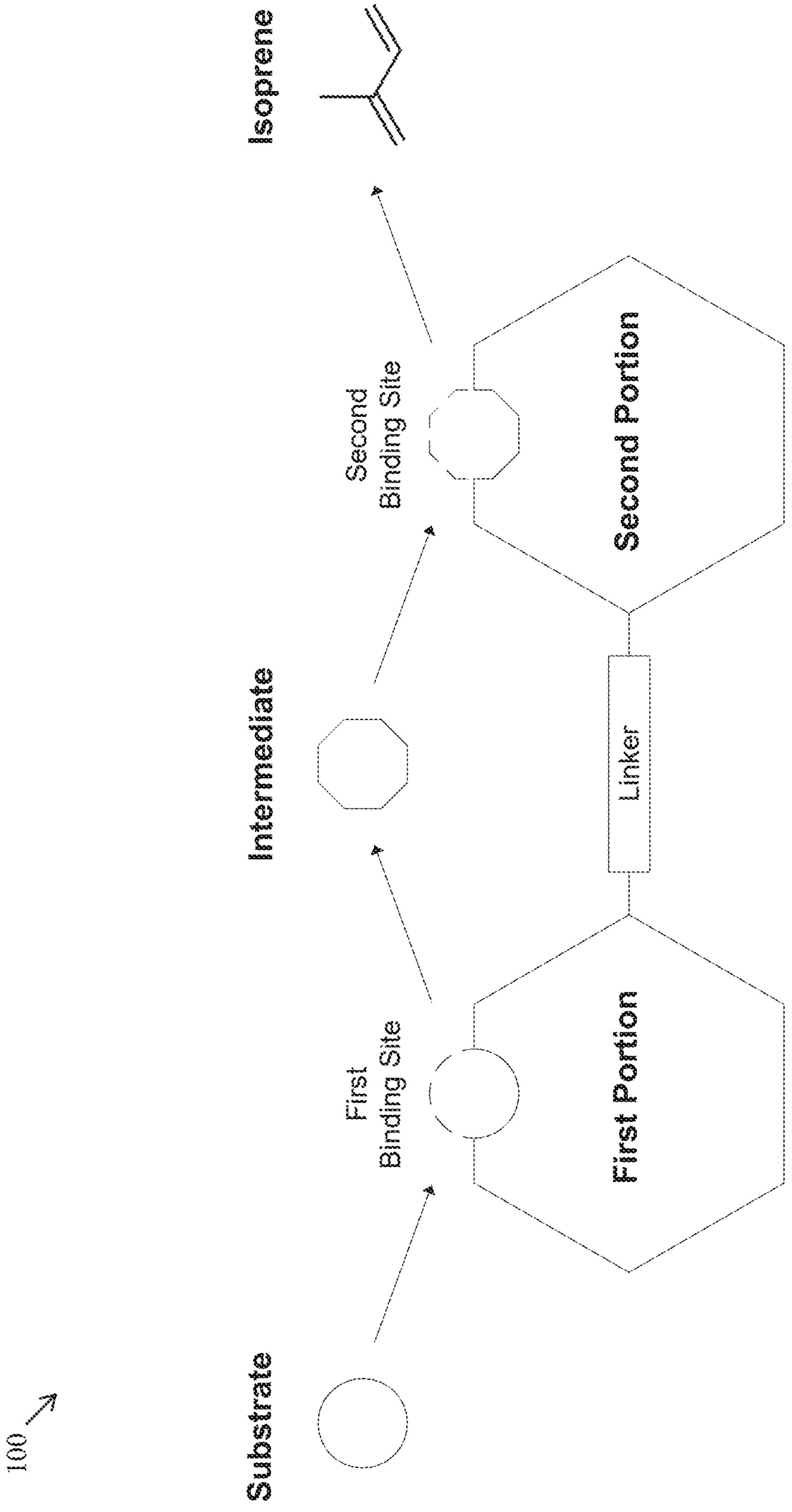
FIG. 1 is a schematic illustration of an exemplary embodiment of a genetically engineered peptide superstructure for production of isoprene and its working principle.

At a high level, aspects of the present disclosure are directed to genetically engineered peptide superstructures for production of isoprene, genetically engineered microbes configured to encode such peptide superstructures, and methods of production related thereto.

Peptide superstructure includes a first portion and a second portion. In one or more embodiments, a second portion is covalently linked to the first portion through a linker. In some cases, linker may include a peptide linker.

The first portion includes a first binding site configured to catalyze a first chemical reaction that converts a substrate to an intermediate.

In one or more embodiments, the first portion may include at least a functional fragment of isopentenyl diphosphate (IPP) isomerase. In one or more embodiments, substrate may include IPP. In one or more embodiments, intermediate may include dimethylallyl pyrophosphate (DMAPP).

The second portion includes a second binding site configured to catalyze a second chemical reaction converting the intermediate to isoprene. The second binding site is located in proximity to the first binding site. In one or more embodiments, the second portion may include at least a functional fragment of isoprene synthase (IspS).

In one or more embodiments, peptide superstructure may be produced in a genetically engineered microbe.

In some cases, genetically engineered microbe may include bacteria or fungi. In some cases, genetically engineered microbes may include *Escherichia* including *Escherichia Coli, Lactococcus* including *Lactococcus lactis, Vibrio* including *Vibrio natriegens, Saccharomyces* including *Saccharomyces cerevisiae, Aspergillus* including *Aspergillus niger, Aspergillus nidulans*, and/or *Aspergillus oryzae, Yarrowia* including *Yarrowia lipolytica, Bacillus* including *Bacillus subtilis, Clostridium* including *Clostridium ljungdahlii*, and/or *Pseudomonas* including *Pseudomonas putida*, among others. In some cases, genetically engineered microbes may include a Crabtree-negative microbe. In some cases, genetically engineered microbes may include a diploid strain. In some cases, genetically engineered microbes may include balanced methylerythritol phosphate (MEP) and mevalonate (MVA) pathways.

Genetically engineered microbe includes a heterologous nucleic acid construct encoding at least a portion of peptide superstructure.

The method of producing isoprene using genetically engineered peptide superstructure includes culturing the genetically engineered microbe under suitable conditions and providing substrate to the cultured genetically engineered microbe to produce isoprene.

Aspects of the present disclosure may be used to provide a sustainable means of producing isoprene and similar value-added chemicals. Aspects of the present disclosure may be used to reduce the dependence on fossil fuels and mitigate the negative environmental impacts thereof. Exemplary embodiments illustrating aspects of the present disclosure are described below in the context of several specific examples.

To facilitate the understanding of this invention, a number of terms are defined below and throughout the disclosure. Unless otherwise defined, all technical and scientific terms used herein have the same meaning as commonly understood by one of ordinary skill in the art to which this invention belongs. The terminology herein is used to describe specific embodiments of the invention, but their usage does not limit the invention, except as outlined in the claims.

It is understood that the acts described below are meant as a general overview and demonstration of an exemplary method, and that the method may include different and/or additional acts as described herein or otherwise.

While the present invention will be described as having particular configurations disclosed herein, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

It is to be understood that any aspect and/or element of any embodiment of the method(s) described herein or otherwise may be combined in any way to form additional embodiments of the method(s) all of which are within the scope of the method(s).

Where a process is described herein, those of ordinary skill in the art will appreciate that the process may operate without any user intervention. In another embodiment, the process includes some human intervention (for example, a step is performed by or with the assistance of a human).

For the purposes of this disclosure, including the claims, the phrase "at least some" means "one or more" and includes the case of only one. Thus, for example, the phrase "at least some ABCs" means "one or more ABCs" and includes the case of only one ABC.

For the purposes of this disclosure, including the claims, the term "at least one" should be understood as meaning "one or more" and therefore includes both embodiments that include one or multiple components. Furthermore, dependent claims that refer to independent claims that describe features with "at least one" have the same meaning, both when the feature is referred to as "the" and "the at least one".

For the purposes of this disclosure, the term "portion" means some or all. Therefore, for example, "A portion of X" may include some of "X" or all of "X". In the context of a conversation, the term "portion" means some or all of the conversation.

For the purposes of this disclosure, including the claims, the phrase "using" means "using at least" and is not exclusive. Thus, for example, the phrase "using X" means "using at least X". Unless specifically stated by use of the word "only", the phrase "using X" does not mean "using only X".

For the purposes of this disclosure, including the claims, the phrase "based on" means "based in part on" or "based, at least in part, on" and is not exclusive. Thus, for example, the phrase "based on factor X" means "based in part on factor X" or "based, at least in part, on factor X". Unless specifically stated by use of the word "only", the phrase "based on X" does not mean "based only on X".

In general, for the purposes of this disclosure, including the claims, unless the word "only" is specifically used in a phrase, it should not be read into that phrase.

For the purposes of this disclosure, including the claims, the phrase "distinct" means "at least partially distinct". Unless specifically stated, distinct does not mean fully distinct. Thus, for example, the phrase "X is distinct from Y" means that "X is at least partially distinct from Y" and does not mean that "X is fully distinct from Y". Thus, for the purposes of this disclosure, including the claims, the phrase "X is distinct from Y" means that X differs from Y in at least some way.

It should be appreciated that the words "first", "second", and so on, in the description and claims, are used to distinguish or identify, and not to show a serial or numerical limitation.

Similarly, letter labels (for example, "(A)", "(B)", "(C)", and so on, or "(a)", "(b)", and so on) and/or numbers (for example, "(i)", "(ii)", and so on) are used to assist in readability and to help distinguish or identify, and are not intended to be otherwise limiting or to impose or imply any serial or numerical limitations or orderings. Similarly, words such as "particular", "specific", "certain", and "given", in the description and claims, if used, are to distinguish or identify, and are not intended to be otherwise limiting.

For the purposes of this disclosure, including the claims, the terms "multiple" and "plurality" mean "two or more," and include the case of "two". Thus, for example, the phrase "multiple ABCs" means "two or more ABCs" and includes "two ABCs". Similarly, for example, the phrase "multiple PQRs" means "two or more PQRs" and includes "two PQRs".

The present invention also covers the exact terms, features, values, and ranges, etc., in case these terms, features, values, and ranges, etc., are used in conjunction with terms such as "about", "around", "generally", "substantially", "essentially", "at least", etc. Thus, for example, "about 3" or "approximately 3" shall also cover exactly 3, and "substantially constant" shall also cover exactly constant.

For the purposes of this disclosure, unless stated otherwise, the terms "about" or "approximately" refer to a value that is within 10% above or below the value being described.

For the purposes of this disclosure, including the claims, singular forms of terms are to be construed as also including the plural form and vice versa, unless the context indicates otherwise. Thus, it should be noted that for the purposes of this disclosure, the singular forms "a", "an", and "the" include plural references unless the context clearly dictates otherwise. In other words, terms such as "a", "an", and "the" are not intended to refer to only a singular entity but include the general class of which a specific example may be used for illustration.

Throughout the description and claims, the terms "comprise", "including", "having", "contain", and their variations should be understood as meaning "including but not limited to" and are not intended to exclude other components unless specifically so stated.

For the purposes of this disclosure, the terms "administration" or "administering" refer to a method of giving a dosage of a compound or pharmaceutical composition to a subject.

For the purposes of this disclosure, the terms "treat", "treating", or "treatment" refer to administration of a compound or pharmaceutical composition for a therapeutic purpose. To "treat a disorder" or use for "therapeutic treatment" refers to administering treatment to a patient already suffering from a disease to ameliorate the disease or one or more symptoms thereof to improve the patient's condition (for example, by reducing one or more symptoms of a neurological disorder). The term "therapeutic" includes the effect of mitigating deleterious clinical effects of certain processes (i.e., consequences of the process, rather than the symptoms of processes).

It will be appreciated that variations to the embodiments of the invention can be made while still falling within the scope of the invention. Alternative features serving the same, equivalent, or similar purpose can replace features disclosed in the specification, unless stated otherwise. Thus, unless stated otherwise, each feature disclosed represents one example of a generic series of equivalent or similar features.

Use of exemplary language, such as "for instance", "such as", "for example" ("for example,"), and the like, is merely intended to better illustrate the invention and does not indicate a limitation on the scope of the invention unless specifically so claimed.

While the invention has been described in connection with what is presently considered to be the most practical, and embodiments thereof are further described in the examples below, it is to be understood that the invention is not to be limited to the disclosed embodiment, but on the contrary, is intended to cover various modifications and equivalent arrangements included within the spirit and scope of the appended claims.

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, and/or components have not been described in detail in order to avoid unnecessarily obscuring claimed subject matter. The illustrative embodiments described in the detailed description and claims are not meant to be limiting. Other embodiments may be utilized, and other changes may be made, without departing from the spirit or scope of the subject matter presented here. It will be readily understood that the aspects of the present disclosure, as generally described herein, can be arranged, substituted, combined, and designed in a wide variety of different configurations, all of which are explicitly contemplated and make part of this disclosure.

Referring now to FIG. 1, an exemplary embodiment of a genetically engineered peptide superstructure for production of isoprene and its working principle is illustrated as scheme 100. For the purposes of this disclosure, a "peptide superstructure" is a peptide, or a group of peptides assembled together, that contains multiple active sites for performing one or more biological functions. In some cases, biological function may include a catalytic function. For the purposes of this disclosure, a "catalytic function" is the ability of a chemical to accelerate a chemical reaction by functioning as a catalyst. Specifically, a catalyst performs its catalytic function by lowering at least an activation barrier along a reaction coordinate and increasing at least a rate constant associated with the at least an activation barrier. In some cases, to perform a catalytic function, a catalyst may first be consumed by one or more reactants to form one or more intermediates, then be regenerated as the one or more intermediates are converted to one or more products. In some cases, one or more reactants may bind to a catalyst, participate in a chemical reaction, then dissociate from the catalyst as one or more products.

With continued reference to FIG. 1, in one or more embodiments, peptide superstructure may include an enzyme. For the purposes of this disclosure, an "enzyme" is a biological catalyst, often a protein, having a three-dimensional structure specifically tailored for fitting a substrate or reactant and catalyzing a chemical reaction therefrom. Enzymes are often characterized by their high catalytic activity, high specificity toward substrates, and sensitivity to environmental factors such as temperature and pH. A substrate may interact with an enzyme (and its active/binding site) via a lock-and-key mechanism or an induced fit. The catalytic function of a catalyst or enzyme may be described using mathematical tools such as Arrhenius equation, Eyring equation, Michaelis-Menten equation, Lineweaver-Burk equation, among others, as deemed suitable by a person of ordinary skill in the art upon reviewing the entirety of this disclosure.

With continued reference to FIG. 1, peptide superstructure includes a first portion and a second portion. For the purposes of this disclosure, a "portion" of a peptide, peptide superstructure, or enzyme is a unitary structure or substructure containing one or more active sites to which a chemical may bind to initiate, terminate, enhance, inhibit, or otherwise modulate one or more biological functions. In some cases, active site may include a catalytically active site where a reactant or substrate may be converted to a product or metabolite at an accelerated rate, as described above. In one or more embodiments, first portion may include at least a functional fragment of a first enzyme, whereas second portion may include at least a functional fragment of a second enzyme distinct from the first enzyme. For the purposes of this disclosure, a "functional fragment" of an enzyme is a part of the enzyme that includes at least a catalytically active site and therefore preserves at least a catalytic function of the enzyme. In some cases, such functional fragments may be created by truncating or simplifying an enzyme to eliminate peripheral, nonessential structures to improve one or more aspects of its properties, such as without limitation solubility. In some cases, first portion and second portion may be fused into a single enzyme that contains multiple active sites.

With continued reference to FIG. 1, in one or more embodiments, second portion may be covalently linked to first portion through a linker. For the purposes of this disclosure, a "linker" is an extended chemical structure that provides a connection between two or more chemical structures using chemical bonds, thereby bringing the two or more chemical structures in proximity with one another. A linker may perform its linking function using any type of intra- and/or intermolecular interaction deemed suitable by a person of ordinary skill in the art, upon reviewing the entirety of this disclosure, such as without limitation covalent bonds including coordinate covalent bonds, electrostatic interactions, van der Waals/hydrophobic contact, hydrogen bonds, among others. In some cases, linker may include a peptide linker. In some cases, first and second portion may be linked together by transcribing two adjacent genes encoding two enzymes in a continuous DNA sequence, consistent with details described in this disclosure, wherein the two adjacent genes are separated by a spacer gene that encodes a peptide linker, such as a GGGS linker (SEQ ID NO: 27), a GSGGGGS linker (SEQ ID NO: 28), a GSGEAAAKEAAAK linker (SEQ ID NO: 29), or the like, depending on the exact length and/or confirmation needed. In some cases, linker may include a linker of an angular or branched geometry to bring first portion and second portion within proximity of one another. In some cases, first and second portion may be linked via post-translational and/or post-synthetic modifications to yield peptide superstructure. A "linker," as used in this disclosure, is a nucleotide sequence that encodes a peptide sequence that is inserted between two polynucleotide sequences encoding protein domains or enzymes, such that upon expression the resulting polypeptide contains both domains separated by the linker sequence. A "flexible linker," as used in this disclosure, is a linker that permits high conformational freedom and allow the fused domains to move relative to one another with minimal steric hindrance. A flexible linker May include amino acid residues such as glycine and serine. For example and without limitation, a glycine-serine (GS) dipeptide sequence may function as a flexible linker in a fusion enzyme construct. A "rigid linker," as used in this disclosure, is a linker that may include amino acid residues that favor ordered secondary structure and resist random coil conformations, thereby maintaining a more fixed distance and orientation between fused domains. For example and without limitation, an alanine-glutamate-lysine (AEK) tripeptide sequence, or related repeats such as EAAAK, may function as a rigid linker that stabilizes an α-helical conformation and limits conformational flexibility. In one or more embodiments, flexible linkers may be used where independent folding or conformational mobility of enzyme domains is desirable, whereas rigid linkers may be used to preserve spatial separation or to orient active sites in a defined geometry, thereby reducing steric interference or promoting desired catalytic efficiency.

With continued reference to FIG. 1, first portion includes a first binding site configured to catalyze a first chemical reaction that converts a substrate to an intermediate. For the purposes of this disclosure, an "intermediate" is a chemical that forms as a product in a first reaction step and is consumed as a reactant in a second reaction step, with no net accumulation. In one or more embodiments, first portion may include at least a functional fragment of isopentenyl diphosphate (IPP) isomerase (idi). Accordingly, in one or more embodiments, substrate may include IPP. In one or more embodiments, intermediate may include dimethylallyl pyrophosphate (DMAPP). IPP and DMAPP may be produced via the methylerythritol phosphate (MEP) and/or the mevalonate (MVA) pathways, as described in detail below in this disclosure.

With continued reference to FIG. 1, second portion includes a second binding site configured to catalyze a second chemical reaction converting intermediate to isoprene. In one or more embodiments, second portion may include at least a functional fragment of isoprene synthase (IspS). IspS is capable of catalyzing a conversion from DMAPP to isoprene. Additional details will be provided below in this disclosure.

With continued reference to FIG. 1, second binding site is located in proximity to first binding site. In some cases, second binding site may be 1 nanometer-1 micrometer away from first binding site. As nonlimiting examples, second binding site may be separated from first binding site by 1 nanometer to 2 nanometers, 2 nanometers to 3 nanometers, 3 nanometers to 4 nanometers, 4 nanometers to 5 nanometers, 5 nanometers to 6 nanometers, 6 nanometers to 7 nanometers, 7 nanometers to 8 nanometers, 8 nanometers to 9 nanometers, 9 nanometers to 10 nanometers, 10 nanometers to 20 nanometers, 20 nanometers to 50 nanometers, 50 nanometers to 100 nanometers, 100 nanometers to 200 nanometers, 200 nanometers to 300 nanometers, 300 nanometers to 400 nanometers, 400 nanometers to 500 nanometers, 500 nanometers to 600 nanometers, 600 nanometers to 700 nanometers, 700 nanometers to 800 nanometers, 800 nanometers to 900 nanometers, or 900 nanometers to 1 micrometer. Such proximity may facilitate an immediate transformation of intermediate to isoprene that bypasses potential side reactions, thereby improving the yield of isoprene. Additional details will be provided below in this disclosure.

With continued reference to FIG. 1, for the purposes of this disclosure, "isoprene", also known as 2-methyl-1,3-butadiene, is a volatile organic compound with the chemical formula $C_5H_8$, a structural formula of $CH_2{=}CHC(CH_3){=}CH_2$, and a normal boiling point of 34° C. Isoprene may be considered a "hemiterpene" (i.e., half of a terpene), and the details of terpenes will be described below in this disclosure. Isoprene is a key building block for synthesizing natural rubber and various other polymers. Additionally, isoprene may be used in the manufacture of synthetic rubber, adhesives, and elastomers, as well as in the production of pharmaceuticals and other specialty chemicals. Isoprene may be produced naturally by plants and trees, particularly in large amounts by the rubber tree (i.e., *Hevea brasiliensis*). It may also be produced industrially through the thermal cracking of petroleum-derived naphtha or, in some cases, through biotechnological methods using genetically engineered microbes, as described in this disclosure. In some cases, isoprene may be synthesized using industrial organic chemistry, via synthetic routes such as an acetone/acetylene route, a propylene dimer route, an isoamylene route, an isopentane route, or an isobutylene/formaldehyde route, among others.

With continued reference to FIG. 1, for the purposes of this disclosure, a "terpene" is an organic compound with the general molecular formula $(C_5H_8)_n$, often characterized by a structure that contains repeating isoprene units. Terpenes are produced predominantly by plants, particularly conifers, and certain insects, and may be involved in various biological functions, including defense mechanisms and communication. Terpenes may be classified as monoterpenes (n=2), sesquiterpenes (n=3), diterpenes (n=4), and higher terpenes (n>4), based on the number of isoprene units they contain. Monoterpenes ($C_{10}H_{16}$) may include without limitation limonene found in citrus peels, myrcene in hops and lemongrass, pinene in pine resin, linalool in lavender, and geraniol in rose oil, among others. Sesquiterpenes ($C_{15}H_{24}$) may include without limitation farnesene in apple coatings, humulene in hops, bisabolol in chamomile, caryophyllene in black pepper, and nerolidol in ginger and tea tree oil. Diterpenes ($C_{20}H_{32}$) may include without limitation taxadiene from yew trees, gibberellins as plant hormones, phytol in chlorophyll, steviol in *Stevia* leaves, and retinol (Vitamin A1) derived from β-carotene. Higher terpenes may include without limitation squalene ($C_{30}H_{50}$) in shark liver oil, lanosterol ($C_{30}H_{500}$) in wool grease, tetraterpenes or tetraterpenoids including carotenoids ($C_{40}H_{56}$) such as beta-carotene in carrots, and rubber (polyterpene) from latex. Terpenes may serve as a biochemical precursor for a wide array of natural products, including essential oils, resins, and various pharmacologically active compounds, making them valuable in industries such as pharmaceuticals, perfumery, and agriculture. Isoprene belongs to a broader class of molecules called isoprenoids, and similarly, terpenes belong to a broader class of molecules called terpenoids, though it is worth noting that these terminologies may often be used interchangeably. An isoprenoid may include a molecule that is derived from isoprene, and similarly, a "terpenoid" may include a molecule that is derived from a terpene, consistent with details described above. Isoprenoids and terpenoids include a large and diverse class of naturally occurring organic compounds. Isoprenoids/terpenoids may also be synthesized through either the MEP pathway or the MVA pathway, as described in detail above. Isoprenoids/terpenoids may play essential roles in various biological processes, including without limitation cellular membrane structure (as cholesterol), photosynthesis (as carotenoids), and growth regulation (as gibberellins). Isoprenoids/terpenoids may also be used in pharmaceuticals, fragrances, and biofuels due to their diverse chemical properties and biological activities.

With continued reference to FIG. 1, it is worth noting that the invention described in this disclosure is not limited to production of isoprene only. As a nonlimiting example, the precursor for producing isoprene, such as without limitation IPP and/or DMAPP, may also be a building block for other isoprenoids, terpenes, or terpenoids; therefore, an accelerated biosynthesis of isoprene may contribute to an increase in yield for producing these isoprenoids, terpenes, or terpenoids. Specifically, in some cases, products of the MVA pathway such as DMAPP and IPP may be converted to geranyl diphosphate (GPP), which may be further converted to monoterpenes, etc. In some cases, products of the MVA pathway such as DMAPP and IPP may be converted to farnesyl diphosphate (FPP), which may be further converted to sesquiterpenes, triterpenes, and/or carotenoids, among others. A person of ordinary skill in the art, upon reviewing the entirety of this disclosure, will be able to recognize how the invention described herein may be extended to other related applications beyond isoprene synthesis.

With continued reference to FIG. 1, at least part of peptide superstructure may be produced by a genetically engineered microbe. For the purposes of this disclosure, a "genetically engineered microbe" is a microbe whose genetic material has been manipulated to alter one or more of its hereditary traits. Such manipulation may include without limitation inserting, deleting, or otherwise modifying one or more specific DNA sequences; as a result of such manipulation, a genetically modified microbe may exhibit one or more different traits in its structure, function, or the like, compared to its naturally occurring (i.e., wild-type) counterparts. For the purposes of this disclosure, a "microbe" is a microscopic organism, including bacteria, archaea, fungi, protozoa, viruses, and/or the like, that is capable of being utilized in one or more aspects of a biotechnological application. A microbe may be characterized by its ability to perform certain biological processes, such as without limitation fermentation, gene expression, and metabolite production, among others. A microbe may be harnessed for purposes such as without limitation recombinant protein production, bioremediation, synthesis of pharmaceuticals, and development of biofuels, among others, due to their diverse metabolic capabilities and ease of genetic manipulation. For the purposes of this disclosure, a "suitable condition" is an environmental condition or factor suitable for the growth and/or replication of a microbe. In some cases, a suitable condition may vary from one type of microbe to another. A suitable condition may include without limitation a suitable temperature/temperature range, a suitable pressure/pressure range, a suitable pH or pH range, a suitable ionic strength/range of ionic strength, a suitable osmolarity/range of osmolarity, a suitable osmotic pressure/range of osmotic pressure, a suitable concentration/concentration range of one or more nutrients, and/or a suitable level of metabolic waste/metabolites, among others. A person of ordinary skill in the art, upon reviewing the entirety of this disclosure, will be able to identify suitable conditions specific to one or more microbes described herein.

With continued reference to FIG. 1, in one or more embodiments, genetically engineered microbe may include bacteria or fungi. In one or more embodiments, genetically engineered microbe may include *Escherichia* including *Escherichia Coli* (or *E. coli*), *Lactococcus* including *Lactococcus lactis, Vibrio* including *Vibrio natriegens* (or *V. natriegens*), *Saccharomyces* including *Saccharomyces cerevisiae* (or *S. cerevisiae*), *Aspergillus* including *Aspergillus niger, Aspergillus nidulans*, and/or *Aspergillus oryzae, Yarrowia* including *Yarrowia lipolytica* (*Y. lipolytica*), *Bacillus* including *Bacillus subtilis* (*B. subtilis*), *Clostridium* including *Clostridium ljungdahlii* (*C. ljungdahlii*), and/or *Pseudomonas* including *Pseudomonas putida* (*P. putida*), among others. In one or more embodiments, different *E. coli* may be used in cloning and expression. For example and without limitation, *E. coli* may include BL21 (DE3), $C_{41}$ (DE3), C43 (DE3), BL21-AI, Origami (DE3), Rosetta-gami (DE3), SHuffle T7, Tuner strains (lacY mutants), Mutant56 (DE3), DH5a, JM109, XL1-Blue, TOP10, HB101, MG1655, W3110, DH1, RV308, HMS174, LS5218.

With continued reference to FIG. 1, for the purposes of this disclosure, *Escherichia coli* (*E. coli*) is a widely studied bacterium that serves as a crucial model organism in biotechnology and molecular biology. *E. coli* is a gram-negative, rod-shaped bacterium naturally found in the intestines of humans and other warm-blooded animals. The simplicity, well-characterized genetics, and rapid growth of *E. coli*, among other traits, make it a suitable host for genetic engineering applications. It is commonly used for producing recombinant proteins, plasmid cloning, and various metabolic engineering processes.

With continued reference to FIG. 1, for the purposes of this disclosure, *Lactococcus* is a genus of Gram-positive, facultatively anaerobic bacteria that belongs to the family Streptococcaceae. *Lactococcus* bacteria are non-spore-forming, usually non-motile, and commonly occur as spherical or ovoid cells that often form chains or pairs. *Lactococcus* species are lactic acid bacteria (LAB), i.e., they are capable of fermenting sugars to produce lactic acid, a process that may be useful in various food fermentation systems. *Lactococcus* species such as without limitation *Lactococcus lactis* are widely used in the dairy industry, particularly in the production of fermented dairy products like cheese and buttermilk, wherein the lactose in milk is converted into lactic acid, which lowers the pH, inhibits the growth of harmful microorganisms, and contributes to the texture and flavor of the final product. Beyond food fermentation, *Lactococcus* may be used in biotechnology for producing recombinant proteins, such as without limitation enzymes and therapeutic proteins, due to its relatively simple genetic system. Additionally, some *Lactococcus* strains may have probiotic potential and/or an ability to produce bioactive compounds, offering applications in food preservation and health supplements.

With continued reference to FIG. 1, for the purposes of this disclosure, *Vibrio natriegens* (*V. natriegens*) is a fast-growing, gram-negative marine bacterium. *V. natriegens* has recently gained prominence in biotechnology due to its exceptionally rapid doubling time of less than 10 minutes under suitable conditions. The fast growth, genetic tractability, high transformation efficiency, and ability to thrive in simple media of *V. natriegens*, among other traits, make it a suitable organism for various applications, including synthetic biology, recombinant protein production, metabolic engineering, and high-throughput screening, among others.

With continued reference to FIG. 1, for the purposes of this disclosure, *Saccharomyces cerevisiae* (*S. cerevisiae*) is a unicellular eukaryote, commonly known as brewer's yeast or baker's yeast, that plays a pivotal role in biotechnology due to its well-characterized genetics and ease of manipulation. *S. cerevisiae* has been instrumental in winemaking, baking, and brewing since ancient times and is a model system extensively used for recombinant DNA technology, metabolic engineering, and synthetic biology applications. Its ability to perform post-translational modifications similar to higher eukaryotes makes it suitable for producing complex proteins and biopharmaceuticals. Additionally, *S. cerevisiae* may be employed in biofuel production, fermentation processes, and various industrial biotechnology applications.

With continued reference to FIG. 1, for the purposes of this disclosure, *Aspergillus* is a genus of filamentous fungi. *Aspergillus* is characterized by its ability to produce a wide array of enzymes, organic acids, and secondary metabolites, making it a suitable host for production of biofuels, pharmaceuticals, and food products. Several genetic manipulation techniques have been established for *Aspergillus*. Certain *Aspergillus* species, such as *Aspergillus niger, Aspergillus nidulans*, and *Aspergillus oryzae*, may be used for recombinant protein production and metabolic engineering due to their efficient protein secretion systems and robust metabolic capabilities. Additionally, and/or alternatively, other filamentous fungi such as without limitation *Fusarium* and/or *Neurospora* may be used.

With continued reference to FIG. 1, for the purposes of this disclosure, *Yarrowia lipolytica* (*Y. lipolytica*) is a species of yeast belonging to genus *Yarrowia* and the family *Dipodascaceae*. It is known for its ability to utilize a wide range of carbon sources, particularly lipids, which makes it a useful organism in biotechnological applications. *Yarrowia lipolytica* may be used in the production of various bioproducts, including single-cell oils, enzymes, and organic acids. *Yarrowia lipolytica* is also notable for its potential use in bioremediation, as it May degrade environmental pollutants such as hydrocarbons and fatty acids. *Yarrowia lipolytica* has a well-studied genetic system, allowing for genetic modifications and metabolic engineering to enhance its production capabilities. Additionally, *Yarrowia lipolytica* is recognized for its lack of toxicity in food and industrial applications, making it an attractive candidate for use in various biotechnological processes.

With continued reference to FIG. 1, for the purposes of this disclosure, *Bacillus subtilis* (*B. subtilis*), is a Gram-positive, rod-shaped bacterium commonly found in soil and the gastrointestinal tracts of ruminants and humans. *Bacillus subtilis* is known for its ability to form endospores, which allow it to survive in harsh environmental conditions. *Bacillus subtilis* is widely studied for its role in various applications, including biotechnology, agriculture, and food production. *Bacillus subtilis* serves as a model organism for laboratory studies due to its genetic tractability and well-characterized physiology. Additionally, *Bacillus subtilis* may be utilized as a probiotic in animal feed and/or as a biocontrol agent in agriculture, promoting plant growth and/or protecting crops from pathogens. Its capability of producing enzymes, antibiotics, and/or other bioactive compounds further underscores its significance in various industrial processes.

With continued reference to FIG. 1, for the purposes of this disclosure, *Clostridium ljungdahlii* (*C. ljungdahlii*) is a gram-positive, anaerobic, rod-shaped bacterium that is part of the genus *Clostridium*. It is notable for its ability to perform autotrophic growth by utilizing a mixture of carbon monoxide (CO), carbon dioxide ($CO_2$), and hydrogen ($H_2$) (i.e., syngas) as sole carbon and energy sources, through a process known as the Wood-Ljungdahl pathway (acetyl-CoA pathway). *Clostridium ljungdahlii* is capable of converting syngas into value-added products, such as without limitation acetone, butanol, ethanol (ABE), and acetic acid, making it an important organism for industrial biotechnology applications, particularly in gas fermentation (for example, syngas fermentation) and biofuel production. *Clostridium ljungdahlii* holds promise for producing renewable fuels and chemicals from waste gases, such as those generated by industrial processes or gasified biomass. Specifically, an advantage of Clostridia as a host organism may derive from their ability to employ diverse carbon sources, including mono-, oligo- and polysaccharides that would be found in waste products, making the fermentation of industrial, agricultural, and waste products conceivable.

With continued reference to FIG. 1, for the purposes of this disclosure, *Pseudomonas putida* (*P. putida*) is a gram-negative, rod-shaped, aerobic bacterium belonging to the genus *Pseudomonas. Pseudomonas putida* is commonly found in soil, water, and various environments where organic compounds are present. *Pseudomonas putida* is notable for its metabolic versatility, which allows it to degrade a wide range of organic compounds including without limitation hydrocarbons, aromatic compounds, and/or environmental pollutants such as without limitation toluene and naphthalene, making it an important organism for environmental bioremediation. Additionally, *Pseudomonas putida* may be used in various industrial and biotechnological applications due to its ability to produce valuable compounds and its resilience under harsh conditions. *Pseudomonas putida* may also be used to produce chemicals, such as biofuels, bioplastics, and other value-added compounds, through microbial fermentation and/or genetic engineering.

With continued reference to FIG. 1, in some cases, creating a genetically engineered microbe may involve using recombinant DNA technology, CRISPR-Cas9, gene cloning, and/or other molecular biology techniques to achieve desired phenotypic changes. For the purposes of this disclosure, "recombinant DNA technology" is a type of technology that involves a manipulation of DNA sequences to create new genetic combinations not found in nature. Recombinant DNA technology may include techniques such as gene cloning, insertion of DNA fragments from one organism into another, and/or use of vectors such as plasmids to transfer a genetic material. Recombinant DNA technology may be used to express new traits or produce biological products such as proteins, enzymes, and hormones and may play a pivotal role in fields such as genetic engineering, biotechnology, and pharmaceutical development.

With continued reference to FIG. 1, for the purposes of this disclosure, a "plasmid" is a circular, double-stranded DNA molecule distinct from a cell's chromosomal DNA and capable of autonomous replication. A plasmid may be used as a vector for insertion, expression, and propagation of foreign genes within a host organism. Such vectors may include specific sequences for an origin of replication, selectable markers, and cloning sites, enabling manipulation and study of genetic material for applications in research, biotechnology, and therapeutic development.

With continued reference to FIG. 1, for the purposes of this disclosure, "CRISPR-Cas9" is a genetic engineering tool, derived from a bacterial immune defense mechanism, that includes Clustered Regularly Interspaced Short Palindromic Repeats (CRISPR) sequences and the CRISPR-associated protein 9 (Cas9) enzyme and allows for precise, targeted modification of DNA within an organism. CRISPR-Cas9 may be programmed with a guide RNA to target a specific DNA sequence, enabling Cas9 enzyme to create double-strand breaks at one or more precise locations, thereby facilitating insertion, deletion, or modification of genetic material.

With continued reference to FIG. 1, genetically engineered microbe includes a heterologous nucleic acid construct. For the purposes of this disclosure, a "heterologous" nucleic acid construct is a nucleic acid construct that originates from a different species or is artificially synthesized and introduced into a host organism. A heterologous nucleic acid construct may be inserted into a host genome or expressed in a host cell to produce proteins, confer new traits, and/or study gene functions. A heterologous nucleic acid may include genes, regulatory elements, or other sequences that are not naturally found in the host organism's genome. For the purposes of this disclosure, a "nucleic acid construct" is a nucleic acid sequence that encodes a peptide and is capable of being expressed to synthesize the peptide. In other words, a nucleic acid construct includes a coding sequence that encodes a peptide and one or more regulatory elements that regulate the expression of the coding sequence. Exemplary embodiments of a regulatory element may include a promoter, an enhancer, a silencer, an insulator, an operator, and a response element, among others. For the purposes of this disclosure, a "promoter" is a DNA sequence where an RNA polymerase binds to initiate transcription. For the purposes of this disclosure, an "enhancer" is a distant element of DNA sequence that increases transcription rates by interacting with a promoter via DNA looping. For the purposes of this disclosure, a "silencer" is a DNA sequence that represses transcription when bound by specific proteins. For the purposes of this disclosure, an "insulator" is a DNA sequence that prevents the interaction between one or more enhancers and one or more promoters of neighboring genes. For the purposes of this disclosure, an "operator" is a DNA segment that regulates the transcription of adjacent genes. For the purposes of this disclosure, a response element is a DNA sequence that responds to external signals, allowing genes to be turned on or off in response to environmental changes. These regulatory elements may work together to ensure precise gene expression necessary for proper cellular function.

With continued reference to FIG. 1, in one or more embodiments, nucleic acid construct may include one or more operons. For the purposes of this disclosure, an "operon" is a functioning unit of DNA containing a cluster of genes under the control of a single promoter. It is commonly found in prokaryotes such as bacteria. These genes are transcribed together into a single messenger RNA strand and typically encode proteins that work together in a specific biological pathway. An operon may include a regulatory element, such as an operator as described above, where an activator or repressor protein may bind to increase or inhibit transcription. An operon may include one or more regulatory genes that encode one or more such activator or repressor proteins. A nonlimiting example of operon may include the lac operon, which regulates lactose metabolism in *E. coli*. In one or more embodiments, lac operon may provide a regulatory framework widely adopted for recombinant expression in *E. coli*. By placing a heterologous gene under the control of a lac promoter or hybrid promoter (trc, tac, lacUV5), expression may be repressed by LacI protein until induction with IPTG. In engineered strains such as BL21 (DE3), induction with IPTG may trigger production of T7 RNA polymerase from a lac-regulated cassette, which in turn drives high-level expression of a target gene cloned under a T7 promoter.

With continued reference to FIG. 1, in one or more embodiments, a vector may be used to genetically engineer a microbe. a "vector" may be any of a number of nucleic acid molecules, viruses, or portions thereof that are capable of mediating entry of, for example, transferring, transporting, or otherwise delivering, a nucleic acid of interest between different genetic environments or into a cell. A nucleic acid of interest may be linked to, or inserted into, the vector using, for example, restriction and ligation. Vectors include, for example, DNA or RNA plasmids, cosmids, naturally occurring or modified viral genomes or portions thereof, nucleic acids that can be packaged into viral capsids, mini-chromosomes, artificial chromosomes, or transposons (for example, the Sleeping Beauty transposon). Plasmid vectors typically include an origin of replication, for example, replication in prokaryotic cells. A plasmid may include part or all of a viral genome, for example, a viral promoter, enhancer, processing or packaging signals, or sequences sufficient to give rise to a nucleic acid that can be integrated into the host cell genome and/or to give rise to infectious virus. Viruses or portions thereof that can be used to introduce nucleic acids into cells may be referred to as viral vectors. Viral vectors include, for example, adenoviruses, adeno-associated viruses, retroviruses (such as lentiviruses or gamma retroviruses), vaccinia virus and other poxviruses, herpesviruses (such as herpes simplex virus), and others. Viral vectors may or may not contain sufficient viral genetic information for production of infectious virus when introduced into host cells, i.e., viral vectors may be replication-competent or replication-defective. In one or more embodiments, for example where sufficient information for production of infectious virus is lacking, it may be supplied by a host cell or by another vector introduced into the cell if production of virus is desired. In one or more embodiments, such information is not supplied if production of virus is not desired. A nucleic acid to be transferred may be incorporated into a naturally occurring or modified viral genome or a portion thereof or may be present within a viral capsid as a separate nucleic acid molecule. A vector may contain one or more nucleic acids encoding a marker suitable for identifying and/or selecting cells that have taken up the vector. Markers include, for example, proteins that increase or decrease resistance or sensitivity to antibiotics or other agents (such as a protein conferring resistance to puromycin, hygromycin, or blasticidin), enzymes whose activities are detectable by assays known in the art (for example, β-galactosidase or alkaline phosphatase), and proteins or RNAs that detectably affect the phenotype of cells that express them (for example, fluorescent proteins). Vectors often include one or more appropriately positioned sites for restriction enzymes, which may be used to facilitate insertion into the vector of a nucleic acid, for example a nucleic acid to be expressed. An expression vector is a vector into which a desired nucleic acid has been inserted or may be inserted such that it is operably linked to regulatory elements (also termed "regulatory sequences," "expression control elements," or "expression control sequences") and may be expressed as an RNA transcript, for example an mRNA that can be translated into protein or a noncoding RNA such as an shRNA or miRNA precursor. Expression vectors include regulatory sequence(s), for example expression control sequences, sufficient to direct transcription of an operably linked nucleic acid under at least some conditions; other elements required or helpful for expression may be supplied by, for example, the host cell or by an in vitro expression system. Such regulatory sequences typically include a promoter and may include enhancer sequences or upstream activator sequences. In some embodiments, a vector may include sequences that encode a 5' untranslated region and/or a 3' untranslated region, which may comprise a cleavage and/or polyadenylation signal. In general, regulatory elements may be contained in a vector prior to insertion of a nucleic acid whose expression is desired, may be contained in an inserted nucleic acid, or may be inserted into a vector following insertion of a nucleic acid whose expression is desired. As used herein, a nucleic acid and regulatory element(s) are said to be "operably linked" when they are covalently linked so as to place the expression or transcription of the nucleic acid under the influence or control of the regulatory element(s). For example, a promoter region would be operably linked to a nucleic acid if the promoter region were capable of effecting transcription of that nucleic acid. One of ordinary skill in the art will be aware that the precise nature of the regulatory sequences useful for gene expression may vary between species or cell types, but may in general include, as appropriate, sequences involved with the initiation of transcription, RNA processing, or initiation of translation. The choice and design of an appropriate vector and regulatory element(s) is within the ability and discretion of one of ordinary skill in the art. For example, one of skill in the art will select an appropriate promoter (or other expression control sequences) for expression in a desired species, for example a mammalian species, or in a desired cell type. A vector may contain a promoter capable of directing expression in mammalian cells, such as a suitable viral promoter, for example from cytomegalovirus (CMV), retrovirus, simian virus (for example SV40), papillomavirus, herpesvirus or other virus that infects mammalian cells, or a mammalian promoter from, for example, a gene such as EF1alpha, ubiquitin (such as ubiquitin B or C), globin, actin, phosphoglycerate kinase (PGK), or a composite promoter such as a CAG promoter (combination of the CMV early enhancer element and chicken beta-actin promoter). In some embodiments a human promoter may be used. In some embodiments, a promoter that ordinarily directs transcription by a eukaryotic RNA polymerase I (a "pol I promoter"), for example a promoter for transcription of ribosomal RNA (other than 5S rRNA) may be used. In some embodiments, a promoter that ordinarily directs transcription by a eukaryotic RNA polymerase II (a "pol II promoter") or a functional variant thereof is used. In some embodiments, a promoter that ordinarily directs transcription by a eukaryotic RNA polymerase III (a "pol III promoter"), for example a promoter for transcription of U6, H1, 7SK or tRNA or a functional variant thereof, is used. One of ordinary skill in the art will select an appropriate promoter for directing transcription of a sequence of interest. Examples of expression vectors that may be used in mammalian cells include, for example, the pcDNA vector series, pSV2 vector series, pCMV vector series, pRSV vector series, pEF1 vector series, and Gateway® vectors. Examples of virus vectors that may be used in mammalian cells include, for example, adenoviruses, adeno-associated viruses, poxviruses such as vaccinia viruses and attenuated poxviruses, retroviruses (for example lentiviruses), Semliki Forest virus, Sindbis virus, and others. In some embodiments, regulatable (for example, inducible or repressible) expression control element(s), for example a regulatable promoter, is/are used so that expression can be regulated, for example turned on or increased or turned off or decreased. For example, the tetracycline-regulatable gene expression system (Gossen & Bujard, Proc. Natl. Acad. Sci. 89:5547-5551, 1992) or variants thereof (see, for example, Urlinger, S, et al. (2000), Zhou, X., et al (2006)) can be employed to provide inducible or repressible expression. Other inducible/repressible systems may be used in various embodiments. For example, expression control elements that can be regulated by small molecules such as artificial or naturally occurring hormone receptor ligands (for example steroid receptor ligands such as naturally occurring or synthetic estrogen receptor or glucocorticoid receptor ligands), tetracycline or analogs thereof, or metal-regulated systems (for example the metallothionein promoter) may be used in certain embodiments. In some embodiments, tissue-specific or cell type-specific regulatory element(s) may be used, for example to direct expression in one or more selected tissues or cell types.

With continued reference to FIG. 1, in one or more embodiments, golden gate assembly may be used as a molecular cloning method to join multiple DNA fragment. "Golden Gate Assembly," as used in this disclosure, is a molecular cloning technique in which multiple DNA fragments may be directionally joined in a single reaction. For example and without limitation, DNA fragment may be joined using a Type IIS restriction enzyme and a DNA ligase. A Type IIS restriction enzyme may include, without limitation, BsaI, BsmBI, or BbsI, which recognizes a specific nucleotide sequence but cleaves the DNA at a defined distance outside of the recognition site. As a result, cleavage may generate a set of user-defined single-stranded overhangs that may be designed to anneal only in a predetermined order, allowing directional assembly of multiple DNA fragments into a vector. A simultaneous action of digestion and ligation in a one-pot reaction may permit repeated cleavage of incorrectly ligated intermediates, while correctly ligated products may accumulate since the recognition sites are removed from the final construct. Thus, Golden Gate Assembly may provide scarless assembly without unwanted sequences remaining at the ligation junction.

With continued reference to FIG. 1, "domesticated Golden Gate Assembly," as used in this disclosure, refers to a Golden Gate Assembly process in which all internal recognition sites for the Type IIS restriction enzyme are removed from the DNA fragments and vector backbone prior to assembly. Domestication may include introducing silent mutations within coding regions or other sequence modifications that do not alter the encoded protein or functional regulatory element, thereby preventing undesired cleavage during the assembly process and enabling efficient and accurate construction of recombinant DNA.

With continued reference to FIG. 1 restriction enzymes, which may be used to facilitate insertion into the vector of a nucleic acid. For example and without limitation, restriction enzymes may include Type IIP (sticky 5' overhangs): EcoRI, BamHI, HindIII, XhoI, SalI, NheI, XbaI, SpeI, BglII, NcoI, NdeI, AgeI, NotI, AvrII, ClaI, MluI; Type IIP (sticky 3' overhangs): PstI, KpnI, SacI, SphI, ApaI, NsiI; Type IIP (blunt): EcoRV, SmaI, PvuII, StuI, DraI, ScaI; Type IIS/IIG: BsaI, BsmBI (Esp3I), BbsI, SapI (BspQI), AarI, FokI, BtgZI; and Homing endonucleases: I-SceI, I-CeuI, PI-SceI, PI-PspI.

With continued reference to FIG. 1, nucleic acid construct encodes at least a portion of peptide superstructure, consistent with details described above.

With continued reference to FIG. 1, in one or more embodiments, genetically engineered microbe may include a Crabtree-negative microbe. For the purposes of this disclosure, a "Crabtree-negative" microbe is a microbe that that does not exhibit the Crabtree effect. A Crabtree-negative microbe may maintain aerobic respiration and efficient ATP production via the tricarboxylic acid cycle and oxidative phosphorylation under high glucose conditions. Such characteristic makes Crabtree-negative microbes potentially valuable for biotechnological applications that require efficient biomass yield and metabolic productivity without the inhibitory effects of fermentation byproducts. Common Crabtree-negative microbes include without limitation *E. coli, Pseudomonas aeruginosa* (*P. aeruginosa*), *Bacillus subtilis* (*B. subtilis*), *Corynebacterium glutamicum* (*C. glutamicum*), and *Saccharomyces kluyveri* (*S. kluyveri*), among others. In contrast, a "Crabtree-positive" microbe is a microbe that exhibits the Crabtree effect. Common Crabtree-positive microbes include without limitation *S. cerevisiae, Saccharomyces pastorianus* (lager yeast), and/or *Schizosaccharomyces pombe* (fission yeast).

With continued reference to FIG. 1, for the purposes of this disclosure, the "Crabtree effect", named after the English biochemist Herbert Grace Crabtree, is a phenomenon where high glucose concentrations inhibit cellular respiration, leading to fermentation even in the presence of oxygen. The Crabtree effect may offer a microbe certain evolutionary advantage, as the Crabtree effect may allow a microbe to quickly generate ATP and outcompete other microbes in glucose-rich environments. The production of ethanol may also inhibit the growth of competing microbes to provide an additional competitive edge.

With continued reference to FIG. 1, in some cases, genetically engineered microbe may include a diploid strain. For the purposes of this disclosure, a "diploid strain" is a type of organism or cell line that contains two complete sets of chromosomes, one from each parent. In genetic and metabolic engineering, diploid strains may be used to study gene function and regulation, create hybrid organisms, and/or enhance desirable traits. A diploid strain may provide a robust system for complementation tests, enabling researchers to determine the function of specific genes. Additionally, a diploid strain may exhibit increased genetic stability and adaptability, making them valuable for industrial applications such as fermentation and the production of biofuels and pharmaceuticals.

With continued reference to FIG. 1, in some cases, genetically engineered microbe may include balanced MEP and MVA pathways. Additional details will be provided below in this disclosure.

Figure 2:
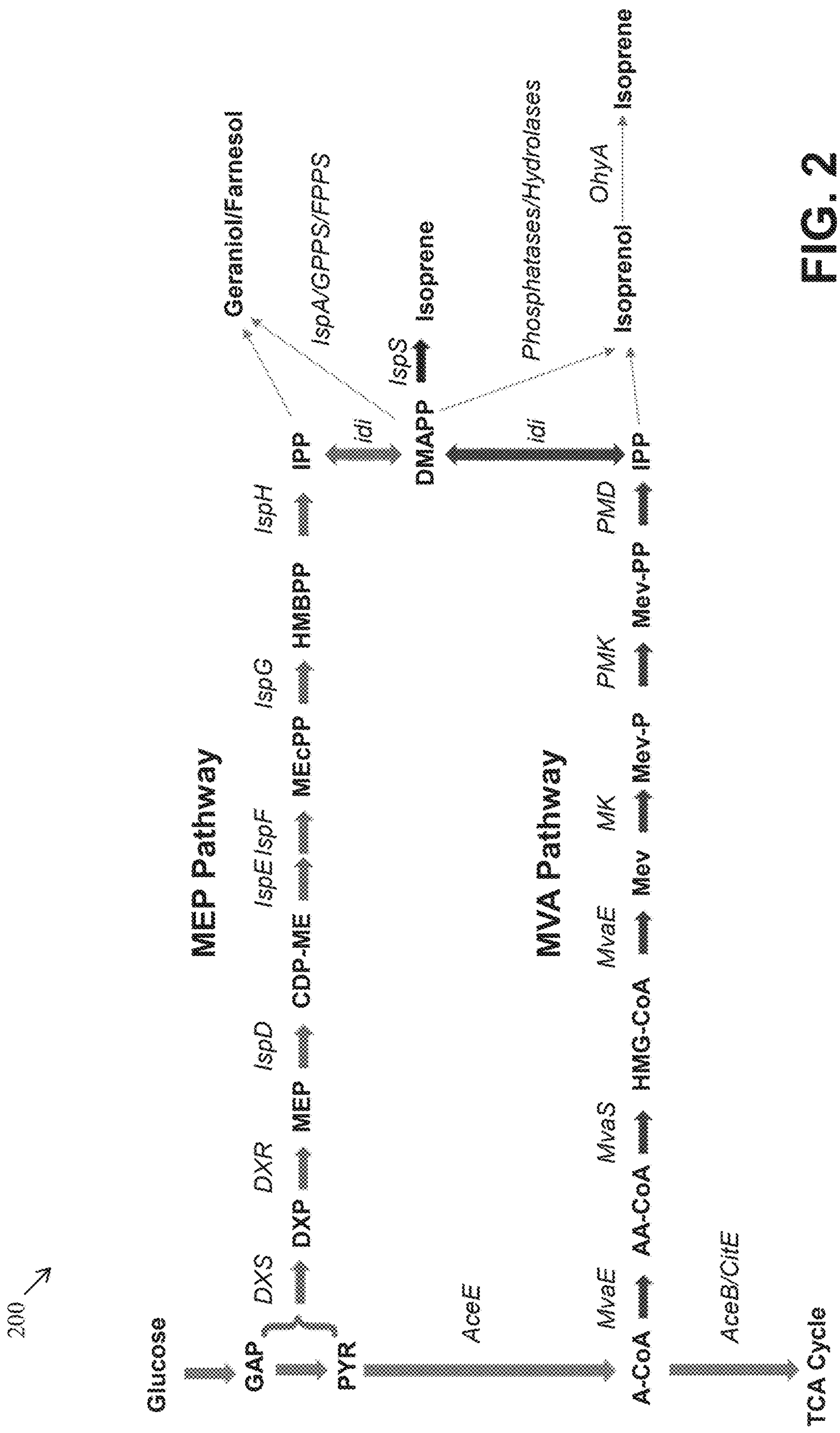
FIG. 2 is an exemplary scheme of the methylerythritol phosphate (MEP) pathway, the mevalonate (MVA) pathway, and additional metabolic pathways associated thereto that are relevant for biosynthesis of isoprene.

Referring now to FIG. 2, scheme 200 illustrates several metabolic pathways pertaining to biosynthesis of isoprene, highlighting the substrate, product, and/or enzyme (catalyst) associated with each step. Scheme 200 includes part of the central metabolic pathway, i.e., the cellular respiration pathway, wherein glucose is broken down to feed the tricarboxylic acid (TCA) cycle. Conversion of glucose involves several key steps. Initially, glucose ($C_6H_{12}O_6$) undergoes glycolysis by converting to two molecules of glyceraldehyde 3-phosphate (GAP). Such conversion is catalyzed by enzymes including hexokinase, phosphofructokinase, and aldolase. GAP is then further processed to form pyruvate ($C_3H_3O_3^-$), producing a net gain of 2 ATP and 1 NADH. Such conversion is catalyzed by enzymes such as glyceraldehyde 3-phosphate dehydrogenase and pyruvate kinase. Pyruvate is further converted to acetyl coenzyme A (A-CoA), releasing NADH and $CO_2$. Such conversion is catalyzed by pyruvate dehydrogenase (PDH), which may include pyruvate dehydrogenase E1 component (encoded by gene AceE). A-CoA then enters the TCA cycle (not shown) and participates in reactions catalyzed by enzymes such as without limitation malate synthase (AceB) or ATP citrate lyase (CitE). It is worth noting that glucose is not the only viable carbon source for the invention described in this disclosure; alternatives such as sucrose, biomass, glycerol, ethanol, plant oils, or the like, may be used instead upon strategic engineering of metabolic pathways.

With continued reference to FIG. 2, scheme 200 includes methylerythritol phosphate (MEP) and mevalonate (MVA) pathways for isoprene production. Both the MEP and the MVA pathways are connected to the central metabolic pathway and may lead to production of isoprene, consistent with details described above. For the purposes of this disclosure, the methylerythritol phosphate (MEP) pathway, also known as the non-mevalonate pathway, is a metabolic route for isoprenoid biosynthesis in bacteria, algae, and/or plant plastids. It begins with the formation of 1-deoxy-D-xylulose-5-phosphate (DXP) from pyruvate and glyceraldehyde-3-phosphate (GAP), which is catalyzed by 1-deoxy-D-xylulose-5-phosphate synthase (DXS). This step is one of the rate-determining steps of the MEP pathway. DXP is then converted to 2-C-methyl-D-erythritol-4-phosphate (MEP), which is catalyzed by 1-deoxy-D-xylulose 5-phosphate reductase (DXR). MEP is then converted to 4-diphosphocytidyl-2-C-methyl-D-erythritol (CDP-ME), which is catalyzed by 4-diphosphocytidyl-2-C-methyl-D-erythritol synthase (IspD). CDP-ME is further converted via two steps to 2-C-methyl-D-erythritol-2,4-cyclodiphosphate (MEcPP), which is catalyzed by 4-diphosphocytidyl-2-C-methyl-Derythritol kinase (IspE) and 2-C-methyl-D-erythritol 2,4-cyclodiphosphate synthase (IspF). MEcPP is then reduced to 4-hydroxy-3-methylbut-2-enyl diphosphate (HMBPP), which is catalyzed by (E)-4-Hydroxy-3-methylbut-2-enyl pyrophosphate synthase (IspG). HMBPP is then converted to isopentenyl diphosphate (IPP) and dimethylallyl diphosphate (DMAPP), which is catalyzed by (E)-4-Hydroxy-3-methylbut-2-enyl pyrophosphate reductase (IspH or HMBPP reductase). IPP and DMAPP may establish a chemical equilibrium and interconvert with one another, which is catalyzed by isopentenyl diphosphate isomerase (idi). DMAPP may be converted to isoprene, which is catalyzed by isoprene synthase (IspS). IspS may be derived from plants, as many plants such as kudzu (the Asian vine, *Pueraria montana*), aspen (*Populus tremuloides*), and poplar (*Populus alba*), among others, may naturally produce isoprene by the catalytic elimination of pyrophosphate from DMAPP. Chemical structures of each reactant, intermediate, and product of the MEP pathway are illustrated in Scheme 1 below:

Scheme 1: The Methylerythritol Phosphate (MEP) Pathway

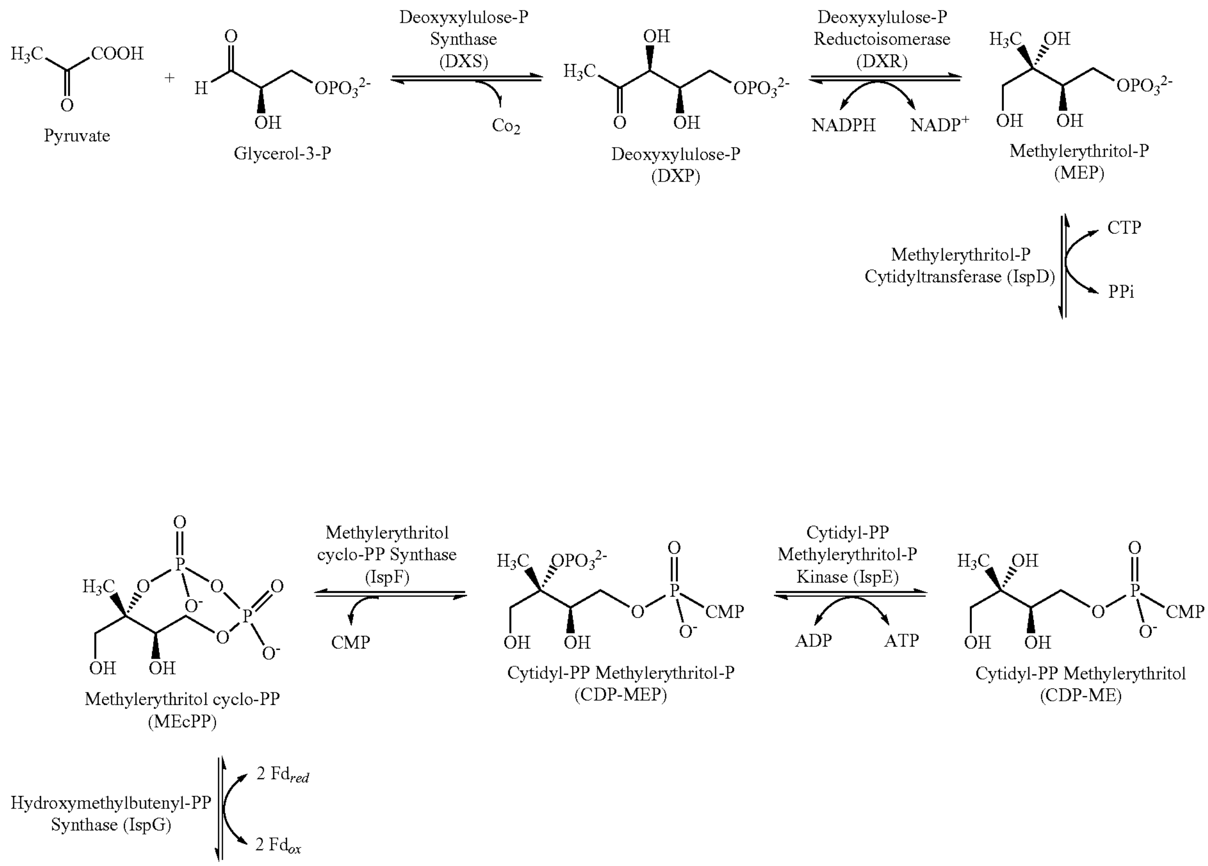

-continued

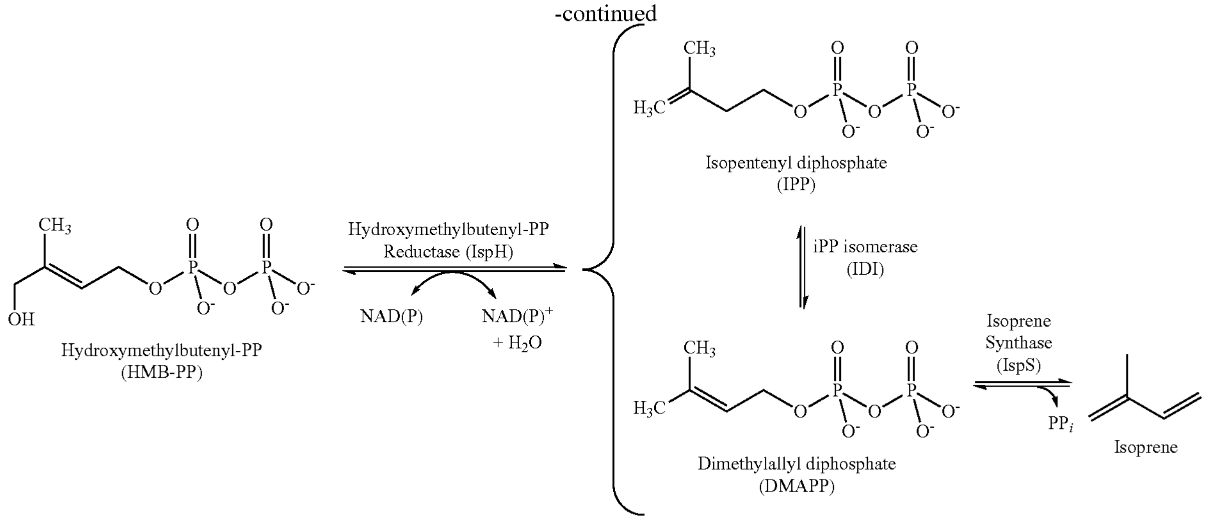

Hydroxymethylbutenyl-PP (HMB-PP)

Isopentenyl diphosphate (IPP)

Dimethylallyl diphosphate (DMAPP)

Isoprene

With continued reference to FIG. 2, for the purposes of this disclosure, the mevalonate (MVA) pathway is another metabolic route for isoprenoid biosynthesis, found in archaea, fungi, animals, and some bacteria. The MVA pathway starts with the conversion of A-CoA to acetoacetyl-coenzyme A (AA-CoA), which is catalyzed by acetoacetyl-coenzyme A thiolase or 3-hydroxy-3-methylglutaryl-coenzyme A reductase (MvaE, which may be encoded by gene ERG10). AA-CoA is then converted to 3-hydroxy-3-methylglutaryl-CoA (HMG-COA), which is catalyzed by HMG-COA synthase (MvaS, which may be encoded by gene ERG13). HMG-COA is then reduced to mevalonate (Mev). This step is catalyzed by MvaE, which may be encoded by gene HMG1, HMG2, or HMG-COA reductase (HMGR). This step is the rate-determining step of the MVA pathway. Mev is phosphorylated to mevalonate-5-phosphate (Mev-P), which is catalyzed by mevalonate kinase (MK), which could be encoded by ERG12. Mev-P is phosphorylated to form mevalonate-5-diphosphate (Mev-PP), which is catalyzed by phosphomevalonate kinase (PMK), which could be encoded by ERG8. Mev-PP is subsequently decarboxylated to produce IPP, which is catalyzed by mevalonate-5-diphosphate decarboxylase or diphosphomevalonate decarboxylase (PMD), which could be encoded by MVD1. IPP and DMAPP may establish a chemical equilibrium and interconvert with one another, which is catalyzed by idi, consistent with details described above. The idi enzyme could be encoded by IDI1. DMAPP may be converted to isoprene, which is catalyzed by IspS, consistent with details described above. In some cases, the MVA pathway may be further categorized into the "upper pathway", which converts A-CoA to MVA, and the "lower pathway", which produces DMAPP from MVA. In some cases, the MVA pathway may be introduced (i.e., cloned) into bacteria such as *E. coli* (which only has a native MEP pathway) as two synthetic operons, using a combination of bacterial and yeast enzymes. As a nonlimiting example, the lower pathway operon may be integrated into the chromosome while the upper pathway operon may be expressed on one or more plasmids, optionally alongside an IspS-encoding gene or the like. Chemical structures of each reactant, intermediate, and product of the MVP pathway are illustrated in Scheme 2 below:

Scheme 2: The Mevalonate (MVA) Pathway

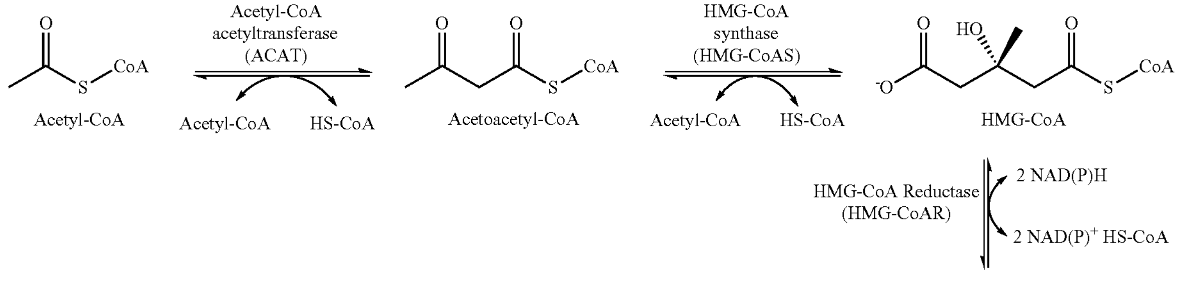

Acetyl-CoA

Acetoacetyl-CoA

HMG-CoA

-continued

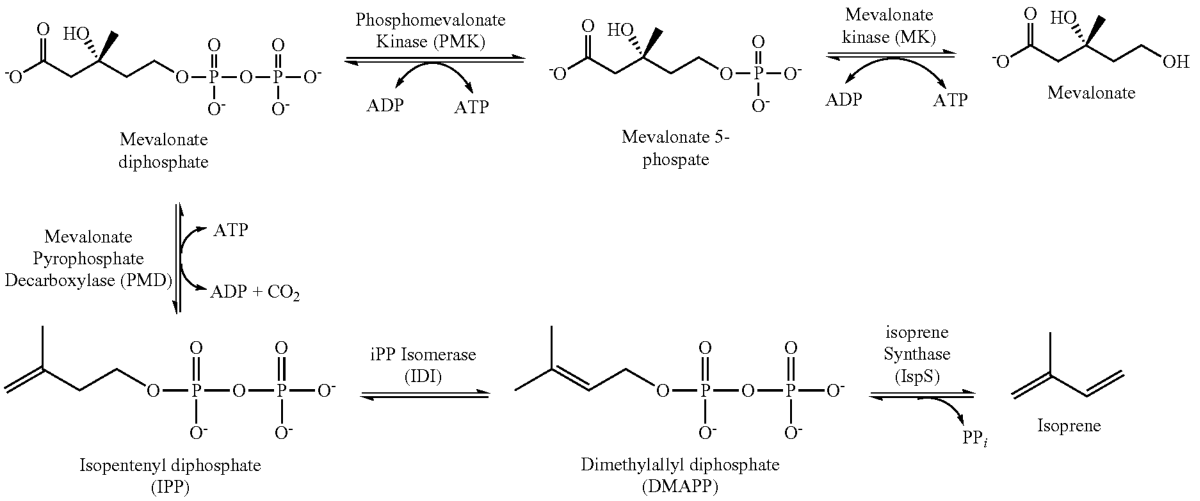

Mevalonate diphosphate

Mevalonate 5-phospate

Mevalonate

Isopentenyl diphosphate (IPP)

Dimethylallyl diphosphate (DMAPP)

Isoprene

With continued reference to FIG. 2, scheme 200 includes a plurality of competing pathways that may limit the yield of isoprene production. IPP and/or DMAPP may be converted to geraniol and/or farnesol, which is catalyzed by enzymes such as without limitation geranyl diphosphate synthase (IspA), geranyl diphosphate synthase (GPPS), and/or farnesyl diphosphate synthase (FPPS). IPP and/or DMAPP may be converted to isoprenol, which is catalyzed by enzymes such as phosphatases and/or hydrolases including the Nudix hydrolase encoded by the NudB gene. As part of the central metabolic pathway, A-CoA may be converted to citrate to enter the tricarboxylic acid cycle, which is catalyzed by enzymes such as ATP citrate lyase (CitE) including AclY, AclB, and/or AclA. These pathways compete with the formation of isoprene. In some cases, to improve the yield of isoprene, byproduct isoprenol may be converted back to isoprene, which may be catalyzed by enzymes such as 3-methyl-3-buten-1-ol dehydroxylase (OhyA) or the like.

With continued reference to FIG. 2, isoprene is derived from intermediates in central metabolism. As described above, the first enzymes in both the MEP and MVA pathways use intermediates in central metabolism as substrates, namely, glyceraldehyde-3-phosphate+pyruvate or acetyl-CoA, respectively. These pathways have differing requirements for reducing power and energy. Thus, in addition to optimizing carbon flux through the MEP and/or MVA pathways, the levels of the central metabolism intermediates may also be maximized, and the reducing power/energy balance may be optimized by metabolic engineering. Additional details will be provided below in this disclosure.

With continued reference to FIG. 2, in one or more embodiments, to create a genetically engineered peptide superstructure for production of isoprene, a gene that encodes an idi may be isolated from *E. coli*. The resulting idi may accordingly be termed Ec-idi (SEQ ID NO: 30). Alternatively, in one or more embodiments, to create a genetically engineered peptide superstructure for production of isoprene, a gene that encodes an idi may be isolated from *S. cerevisiae*. The resulting idi may accordingly be termed Sc_idi (SEQ ID NO: 31). Similarly, in one or more embodiments, to create a genetically engineered peptide superstructure for production of isoprene, a gene that encodes an IspS may be sourced from *Populus alba* (*P. alba*). The resulting IspS may accordingly be termed Pa-IspS (SEQ ID NO: 25). Alternatively, in one or more embodiments, to create a genetically engineered peptide superstructure for production of isoprene, a gene that encodes an IspS may be sourced from *Pueraria montana* (*P. montana*). Specifically, in some cases, an IspS-encoding gene from *P. montana* may be further truncated to improve the solubility and/or activity of the IspS it encodes. As a nonlimiting example, this gene may be truncated at its 5' end to produce a truncated IspS. The resulting truncated IspS may accordingly be termed tPm-IspS (SEQ ID NO: 26). In some cases, the sequence that encodes an idi may be located either upstream or downstream with respect to the sequence that encodes an IspS, with a sequence encoding a peptide linker (SEQ ID NO: 27-29) in between, consistent with details described above. As a nonlimiting example, a permutation between 2 types of idi (SEQ ID NO: 30-31), 2 types of IspS (SEQ ID NO: 25-26), 3 types of peptide linkers (SEQ ID NO: 27-29), and 2 types of arrangements (IspS-linker-idi or idi-linker-IspS) may create a library of 24 candidate gene sequences that encode a peptide superstructure (SEQ ID NO: 1-24). It is worth noting that the designation of first portion, second portion, first binding site, and second binding site, among others, is arbitrary. As a nonlimiting example, a nucleic acid sequence encoding first portion of peptide superstructure may be located either upstream or downstream, from the 5' end to the 3' end of heterologous nucleic acid construct, with respect to a nucleic acid sequence encoding second portion of the peptide superstructure.

Figure 3A:
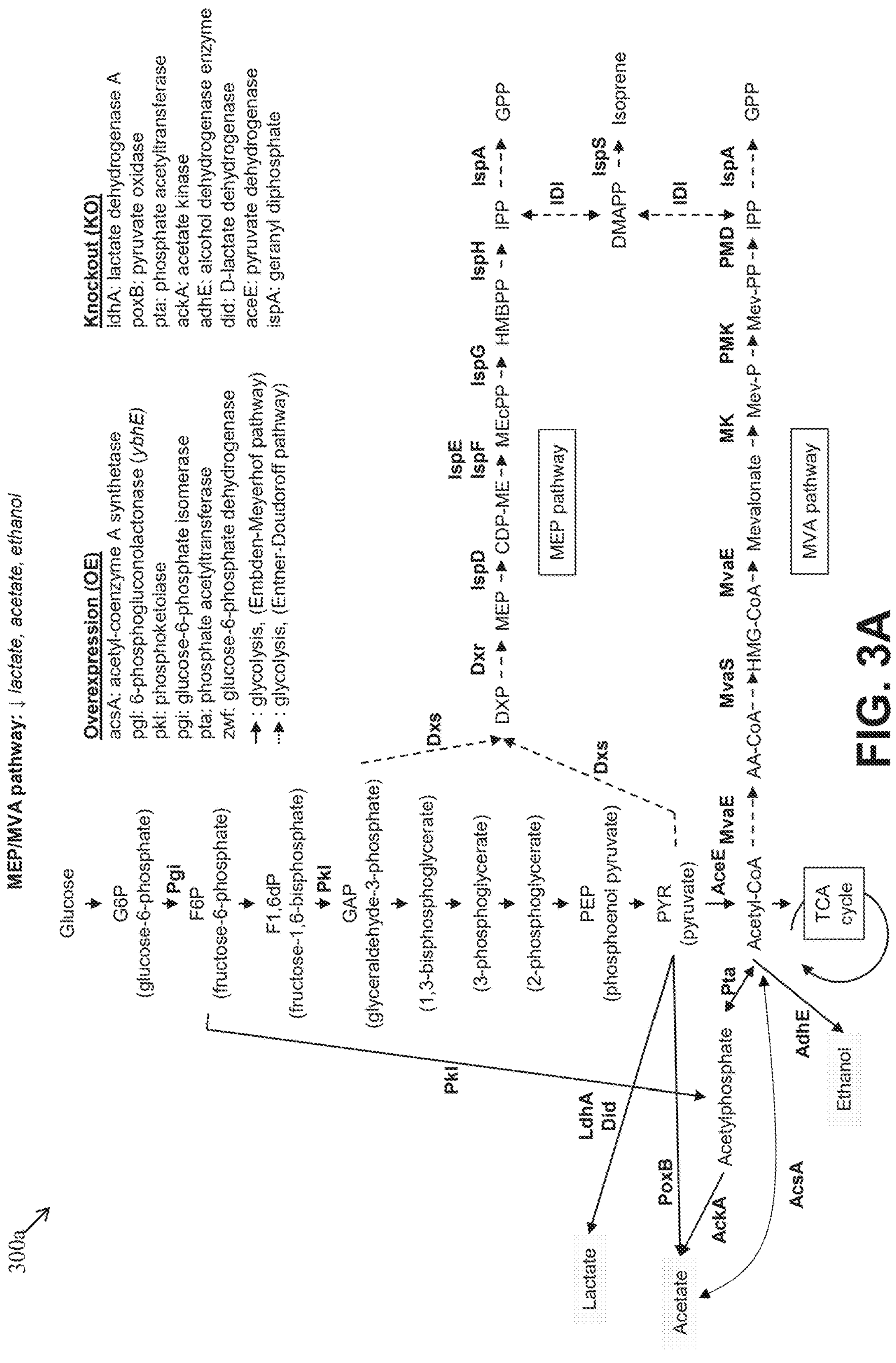
FIGS. 3A-B are additional exemplary schemes of expanded metabolic pathways that are relevant for biosynthesis of isoprene; potential gene targets are also included, wherein the gene targets may be overexpressed or knocked down/knocked out to improve the yield of isoprene.
Figure 3B:
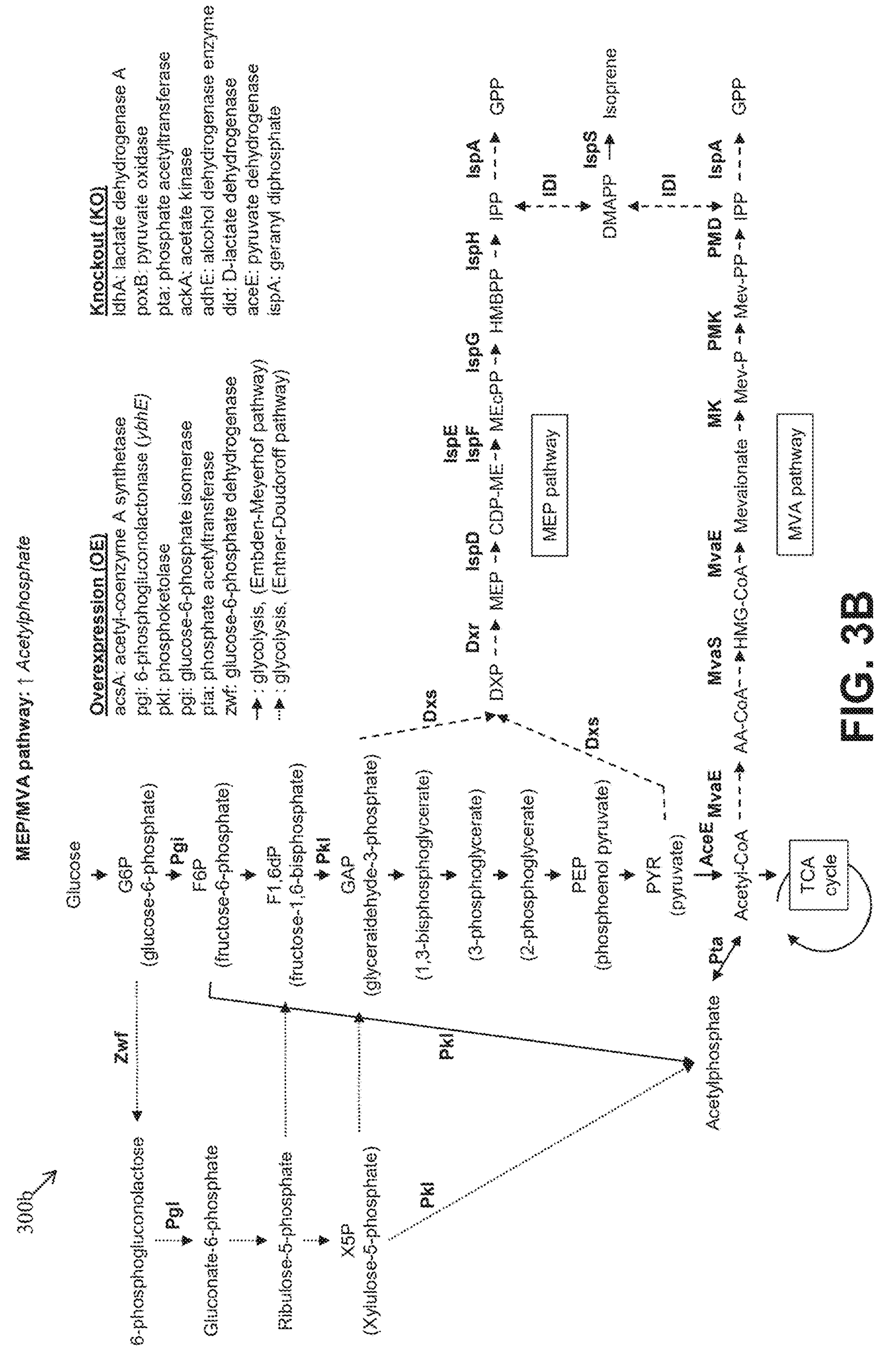

Referring now to FIGS. 3A-B, exemplary embodiments 300a-b of expanded metabolic pathways pertaining to isoprene biosynthesis are illustrated. FIGS. 3A-B include a plurality of potential gene targets. These gene targets and the activity thereof may be upregulated (for example, overexpressed), downregulated (for example, knocked down (KD)/knocked out (KO)), or otherwise modified, either individually or in combination, to increase the yield of isoprene.

With continued reference to FIGS. 3A-B, in one or more embodiments, the inherent activity of an enzyme may be improved by modifying the nucleic acid sequence that encodes the enzyme. Various techniques may be used to improve the inherent activity of an enzyme. As a nonlimiting example, directed evolution may be used to mimic natural selection in the lab by creating a large library of enzyme variants and selecting those with improved traits. As another nonlimiting example, site-directed mutagenesis may be used to introduce one or more specific mutations to enhance enzyme activity or stability. As another nonlimiting example, gene shuffling may be used to recombine segments of related genes to create new variants with enhanced properties. As another nonlimiting example, fusion proteins may be created by combining enzymes with other proteins to improve their function and/or stability. As another nonlimiting example, an enzyme such as DXS may be modified to lift one or more feedback regulations/inhibitions caused by an accumulation of its downstream products such as DMAPP, thereby improving the efficiency of isoprene synthesis. As a nonlimiting example, an enzyme such as OhyA or the like may be engineered to increase its inherent activity, thereby facilitating accumulation of isoprene while lifting the potentially toxic impact of isoprenol. As another nonlimiting example, an enzyme such MvaE or HMGR may be truncated from its naturally existing counterpart to improve its catalytic activity. As another nonlimiting example, one or more cofactors for one or more enzymes may be switched in order to improve the catalytic activity of an enzyme or enable fermentation conditions to be utilized that are more cost effective (e.g., with a lower oxygen requirement).

With continued reference to FIGS. 3A-B, in one or more embodiments, genes encoding enzymes such as 1-deoxy-D-xylulose-5-phosphate synthase (DXS), isoprene synthase (IspS), 3-hydroxy-3-methylglutaryl-coenzyme A reductase (HMG-COA reductase or HMGR), 3-methyl-3-buten-1-ol dehydroxylase (OhyA) or OhyA-like enzymes, (E)-4-hydroxy-3-methylbut-2-enyl diphosphate synthase (IspG), 1-deoxy-D-xylulose 5-phosphate reductase (DXR), (E)-4-hydroxy-3-methylbut-2-enyl diphosphate reductase (IspH or HMBPP reductase), acetyl-CoA C-acetyltransferase/acetoacetyl-coenzyme A thiolase (MvaE, encoded by gene ERG10), HMG-CoA Synthase (MvaS, encoded by gene ERG13), acylating acetaldehyde dehydrogenase (A-ALD), among others, may be modified to increase the inherent activity of the enzyme, consistent with details described in the rest of this disclosure.

With continued reference to FIGS. 3A-B, in one or more embodiments, the activity of an enzyme may be modulated by increasing or upregulating an expression of a nucleic acid construct that encodes the enzyme. In some cases, a coding sequence may be configured to upregulate one or more genes encoding enzymes such as 3-methyl-3-buten-1-ol dehydroxylase (OhyA), transcription factor (encoded by UPC2), acetyl-CoA C-acetyltransferase/acetoacetyl-coenzyme A thiolase (MvaE, encoded by gene ERG10), mevalonate kinase (MK, encoded by ERG12), HMG-COA synthase (MvaS, encoded by gene ERG13), aldehyde dehydrogenase (encoded by ALD5), acetyl-CoA synthetase (encoded by ACSA, ACS1, and/or ACS2, depending on the exact chassis used), pantothenate kinase (encoded by CAB1), dihydrolipoamide acetyltransferase component of the pyruvate dehydrogenase complex (encoded by LAT1), glucose-6-phosphate dehydrogenase (encoded by zwf), 6-phosphogluconolactonase (ybhE, encoded by pgl), phosphoketolase (encoded by pkl), glucose-6-phosphate isomerase (encoded by pgi), and phosphate acetyltransferase (encoded by pta), among others, as these genes encode enzymes that may contribute to the production and/or accumulation of isoprene. In some cases, regulation of a single gene may result in a regulation of multiple enzymes. As a nonlimiting example, when UPC2 is upregulated, ERG12 and ERG13 may also be overexpressed.

With continued reference to FIG. 3A-B, in one or more embodiments, the activity of an enzyme may be modulated by decreasing, attenuating, downregulating, or deleting the expression of a nucleic acid construct that encodes the enzyme. In some cases, a gene encoding an enzyme may be knocked down or knocked out. As nonlimiting examples, one or more genes encoding enzymes such as geranyl diphosphate synthase (IspA), farnesyl pyrophosphate synthetase (Erg 20), geranyl diphosphate synthase (GPPS), geranylgeranyl diphosphate synthase (BTS1), farnesyl diphosphate synthase (FPPS), pyruvate dehydrogenase (encoded by PDH) including pyruvate dehydrogenase E1 component (encoded by AceE), pyruvate oxidase (encoded by poxB), pyruvate decarboxylase (encoded by PDC), malate synthase (encoded by AceB or MLS1), citrate synthase (encoded by CIT1), ATP-citrate lyase (CitE) including AclY, AclB, and AclA, glycerol-producing enzymes including cGPDH and G3PP [41], ethanol-producing enzymes including invertase and zymase, alcohol dehydrogenase (encoded by ADH1), alcohol dehydrogenase enzyme (encoded by adhE), lactate-producing enzymes including lactate dehydrogenase such as lactate dehydrogenase A (encoded by IdhA) and D-lactate dehydrogenase (encoded by did), acetate-producing enzymes including acetyl coenzyme A (acetyl-CoA) hydrolases, acetate kinase (encoded by ackA), phosphatase, and/or hydrolase (for example, a hydrolase encoded by the NudB gene), among others, may be downregulated. However, it is worth noting that, in some cases, an enzyme may perform an essential function of a chassis and should not be completely knocked out or suppressed. As a nonlimiting example, FPPS encoded by ERG20 is essential to *S. cerevisiae*, and accordingly, specific sites within FPPS may be mutated in order to downregulate (not eliminate) its function. As another nonlimiting example, a diploid strain may be used to knockout one copy of ERG20 gene in order to downregulate the activity of the enzyme it encodes. In some cases, an enzyme may not be essential to a chassis and may be knocked out without causing adverse effects. As a nonlimiting example, genes such as MLS1 and CIT1 may be knocked out in such manner.

With continued reference to FIG. 3A-B, in some cases, multiple upregulations and downregulations may be implemented simultaneously to achieve a synergic effect. As a nonlimiting example, gene targets such as zwf, pgl, and/or pkl may be upregulated simultaneously to utilize the Entner-Doudoroff pathway in addition to the Embden-Meyerhof pathway regulated by pgi and pkl, thereby increasing the carbon flux of biosynthesis and increasing the yield of acetylphosphate (see FIG. 3A, embodiment 300a). As another nonlimiting example, gene targets such as ackA-pta, poxB, and/or ldhA may be knocked down or knocked out simultaneously to suppress competing reactions that form acetate, lactate, and/or ethanol (see FIG. 3B, embodiment 300b). As another nonlimiting example, simultaneous upregulation of ALD5 and downregulation of ADHI may be combined to prevent acetyl-CoA from converting to ethanol via fermentation. Table 1 summarizes exemplary gene targets for upregulation and downregulation for *S. cerevisiae* and *E. coli.*

TABLE 1

Gene Targets for Improving Isoprene Production in *S. cerevisiae* and *E. coli*.

| Organism | Gene | Type of Genetic Modification Note: Knockout (KO) Knockdown (KD) Overexpress (OE) | Rationale |
|---|---|---|---|
| *S. cerevisiae* | ERG20: farnesyl pyrophosphate synthetase | KD or mutate specific sites | Essential Gene; increase DMAPP |
| *S. cerevisiae* | BTS1: geranylgeranyl diphosphate synthase | KO | Increase DMAPP |
| *S. cerevisiae* | UPC2: transcription factor | OE | Increase products of MVA pathway |
| *S. cerevisiae* | ERG10: acetyl-CoA C-acetyltransferase | OE | Increase products of MVA pathway |
| *S. cerevisiae* | ERG12: Mevalonate kinase | OE | Increase products of MVA pathway |
| *S. cerevisiae* | ERG13: HMG-CoA synthase | OE | |
| *S. cerevisiae* | ALD5: aldehyde dehydrogenases | OE | Increase flux from acetaldehyde to acetyl-CoA instead of ethanol production. Could also work with fed ethanol to push towards acety-CoA |
| *S. cerevisiae* | ADH1: alcohol dehydrogenase | KO | Increase flux from acetaldehyde to acetyl-CoA instead of ethanol production. Could also work with fed ethanol to push towards acety-CoA |
| *S. cerevisiae* | ACS1 and ACS2: acetyl-CoA synthetase | OE | Increase flux from acetaldehyde to acetyl-CoA instead of ethanol production. Could also work wih fed ethanol to push towards acety-CoA |
| *S. cerevisiae* | MLS1: Malate synthase | KO | Increase acetyl CoA pool |
| *S. cerevisiae* | CIT1: Citrate synthase | KO | Increase acetyl CoA pool |
| *S. cerevisiae* | CAB1: Pantothenate kinase | OE | Increase acetyl CoA pool |
| *S. cerevisiae* | LAT1: dihydrolipoamide acetyltransferase component of the pyruvate dehydrogenase complex | OE | Increase acetyl CoA pool |
| *E. coli* | zwf: glucose-6-phosphate dehydrogenase | OE | Increase carbon flux to acetylphosphate (overexpression of the Entner-Doudoroff pathway) |
| *E. coli* | acsA: acetyl-coenzyme A synthetase | OE | Increase carbon flux from acetate to acetyl-CoA |
| *E. coli* | pgl: 6-phosphogluconolactonase (ybhE) | OE | Increase carbon flux to acetylphosphate (overexpression of the Entner-Doudoroff pathway) |
| *E. coli* | pkl: phosphoketolase | OE | Increase carbon flux to acetylphosphate (overexpression of the Entner-Doudoroff pathway) |
| *E. coli* | pgi: glucose-6-phosphate isomerase | OE | Increase carbon flux from G6P to F6P |
| *E. coli* | pta: phosphate acetyltransferase | OE | Increase acetyl-CoA from acetylphosphate |
| *E. coli* | ldhA: lactate dehydrogenase A | KO/KD | Reduce lactate production from pyruvate |
| *E. coli* | poxB: pyruvate oxidase | KO/KD | Reduce acetate production from pyruvate |
| *E. coli* | ackA: acetate kinase | KO/KD | Reduce acetate production from acetylphosphate |

TABLE 1-continued

Gene Targets for Improving Isoprene Production in *S. cerevisiae* and *E. coli*.

| Organism | Gene | Type of Genetic Modification Note: Knockout (KO) Knockdown (KD) Overexpress (OE) | Rationale |
|---|---|---|---|
| *E. coli* | adhE: alcohol dehydrogenase enzyme | KO/KD | Reduce ethanol production from acetyl-CoA |
| *E. coli* | did: D-lactate dehydrogenase | KO/KD | Reduce lactate production from pyruvate |
| *E. coli* | aceE: pyruvate dehydrogenase | KD | Increase carbon flux to MEP pathway from pyruvate |
| *E. coli* | ispA: geranyl diphosphate | KD | Increase carbon flux to DMAPP from IPP and reduce it to GPP from IPP |

With continued reference to FIGS. 3A-B, in one or more embodiments, promoter engineering may be used to improve the transcriptional level of a gene. Promoter engineering modifies the promoter region to increase gene expression levels, thereby improving enzyme production and activity. In one or more embodiments, codon optimization may be used to improve the translational efficiency of a gene. For the purposes of this disclosure, "codon optimization" is a technique used in genetic engineering to improve the expression of a gene in a particular host organism. Codon optimization involves altering the DNA sequence of a gene to use codons that are more frequently preferred by the host organism's translational machinery. A codon optimization process may take into account a codon bias of the host, ensuring that a synthetic gene sequence is translated more efficiently into the desired protein. Codon optimization may enhance the yield and function of a protein, which may be crucial for various applications in biotechnology and synthetic biology. It is worth noting that promoter engineering and codon optimization are distinct yet complementary techniques in genetic engineering. Promoter engineering involves modifying the promoter region of a gene to enhance its expression by improving the binding efficiency of transcriptional machinery. Codon optimization, on the other hand, focuses on altering the coding sequence of a gene to use preferred codons of the host organism, thereby improving translation efficiency. While both aim to increase protein production, promoter engineering targets transcriptional levels, and codon optimization targets translational efficiency. Combining both techniques may in some cases synergistically enhance an overall gene expression.

With continued reference to FIGS. 3A-B, in some cases, a gene encoding an enzyme may be silenced using Hfq-mediated RNA silencing. For the purposes of this disclosure, "Hfq-mediated RNA silencing" is a process wherein the Hfq protein facilitates a regulation of gene expression through RNA interactions, by binding to small regulatory RNAs (sRNAs) and messenger RNAs (mRNAs) to promote a formation of RNA duplexes. This interaction may enhance or inhibit a translation of target mRNAs, leading to gene silencing. In some cases, this process may be useful for post-transcriptional regulation and may be harnessed for genetic engineering, therapeutic interventions, and synthetic biology applications. As nonlimiting examples, to facilitate accumulation of isoprene, Hfq-mediated RNA silencing may be used against geranyl diphosphate synthase (IspA), farnesyl pyrophosphate synthetase (Erg 20), geranyl diphosphate synthase (GPPS), geranylgeranyl diphosphate synthase (BTS1), farnesyl diphosphate synthase (FPPS), malate synthase (encoded by AceB or MLS1), ATP-citrate lyase (CitE) including AclY, AclB, and AclA, and/or pyruvate dehydrogenase (encoded by PDH) including pyruvate dehydrogenase E1 component (encoded by AceE), among others, to downregulate its activity, consistent with details described above.

With continued reference to FIGS. 3A-B, in some cases, one or more pathways within schemes of embodiments 300a or 300b may be condensed, inhibited, rearranged, or otherwise modified. As a nonlimiting example, one or more genes encoding one or more enzymes may be modified to provide a phosphoketolase workaround, such as by upregulating glycolysis, the pentose phosphate pathway, or the Entner-Doudoroff pathway. As another nonlimiting example, one or more enzymes may be co-localized to create multiple reaction centers in tandem, thereby bypassing one or more competing side reactions, consistent with details described above. As another nonlimiting example, one or more genes encoding one or more enzymes may be modified to inhibit the phosphotransacetylase-acetate kinase (Pta-AckA) pathway to facilitate acetate reuptake in a Crabtree-positive enzyme. The Pta-AckA pathway is a key metabolic route in many bacteria and may be particularly significant under anaerobic conditions or when there is an excess of carbon sources, as it allows a cell to dispose of excess A-CoA and generate additional ATP. Inhibition of the Pta-AckA pathway may facilitate an acetate reuptake and improve the overall carbon efficiency of isoprene production. The Pta-AckA pathway involves two main enzymes: Pta catalyzes the conversion of A-CoA to acetyl phosphate, whereas AckA catalyzes the conversion of acetyl phosphate to acetate to generate ATP. By inhibiting these enzymes, the production of acetate may be reduced. Such reduction may be beneficial in preventing acetate accumulation that can be detrimental to cellular growth and productivity. Genetically engineered microbe may be configured to produce a Pta-AckA inhibitor. For the purposes of this disclosure, a "phosphotransacetylase-acetate kinase inhibitor" is a chemical compound that interferes with the activity of the phosphotransacetylase (Pta) and/or acetate kinase (AckA). Nonlimiting examples of Pta-AckA inhibitors may include deacetylase inhibitors such as tricostatin A and nicotinamide. Specifically, such inhibitors may function by regulating acetyl phosphate-dependent protein acetylation. As another nonlimiting example, the MEP and the MVA pathways may be balanced with each other. Specifically, leveraging the MEP and MVA pathways may enhance the yield and production efficiency of isoprene by optimizing the flux of metabolites, providing metabolic redundancy, and improving the robustness of the production strain under varying conditions. In some cases, such balanced pathways may be implemented using a shunt. Such balanced pathways may offer several benefits. As a nonlimiting example, such balanced pathways may lead to a more efficient utilization of substrates, thereby reducing waste and improving the carbon economy of a genetically engineered microbe. Additionally, as a further nonlimiting example, such balanced pathways may allow for finer control over metabolic fluxes through genetic and regulatory modifications, facilitating the tuning of pathway activities to match specific production needs. Overall, such balanced pathways may enhance the efficiency, robustness, and flexibility of isoprene production, making it more economically viable and sustainable for industrial applications. As another nonlimiting example, the MEP and the MVA pathways may be balanced by increasing a flux through the MEP pathway to reduce carbon loss to the TCA cycle; this strategy may lead to an increase in isoprene production. A theoretical calculation of isoprene yield based upon flux ratios through the MEP and MVA pathways suggests that isoprene yield may increase with an increasing flux along the MEP pathway, with a maximum yield of approximately 0.31 g of isoprene per gram of glucose when the flux ratio is approximately 60:40.

Figure 4:
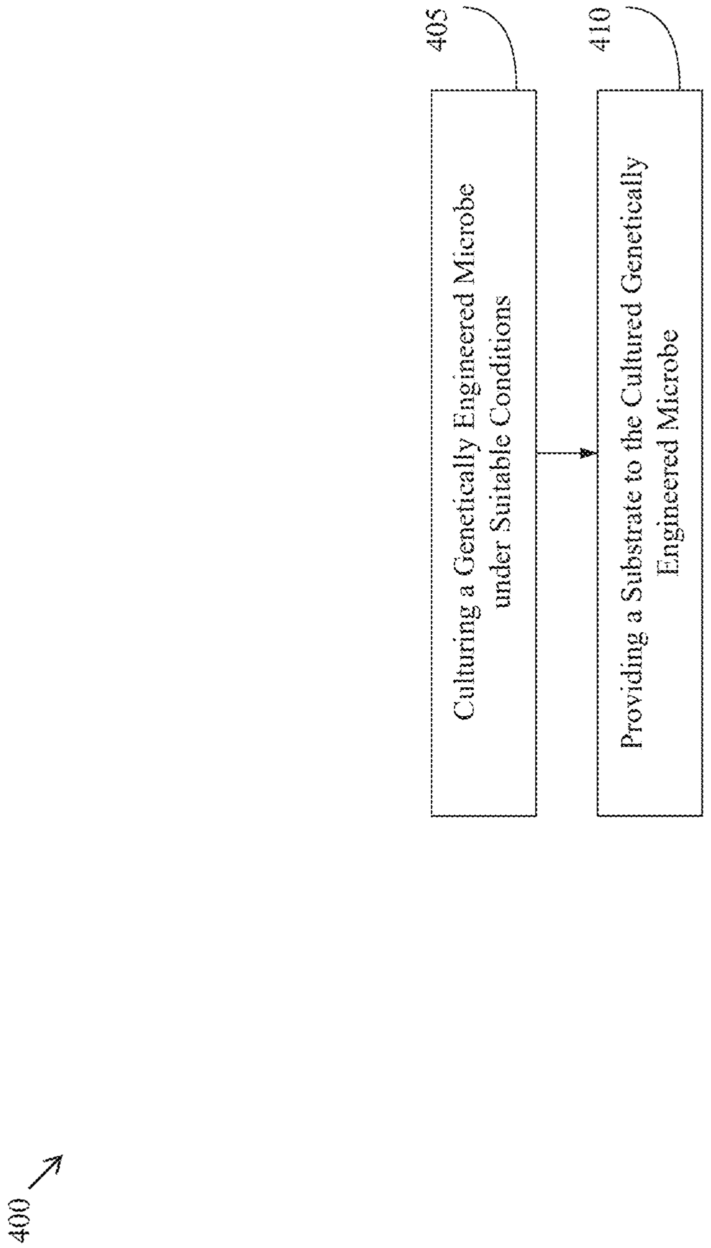
FIG. 4 is a schematic illustration of an exemplary embodiment of a method for producing isoprene using a genetically engineered peptide superstructure.

Referring now to FIG. 4, a method 400 for producing isoprene using genetically engineered peptide superstructure is illustrated. At step 405, method 400 includes culturing a genetically engineered microbe under suitable conditions, consistent with details described above without limitation. For the purposes of this disclosure, a "suitable condition" is an environmental condition or factor suitable for the growth and/or replication of a microbe. In some cases, a suitable condition may vary from one type of microbe to another. A suitable condition may include without limitation a suitable temperature/temperature range, a suitable pressure/pressure range, a suitable pH or pH range, a suitable ionic strength/range of ionic strength, a suitable osmotic pressure/range of osmotic pressure, a suitable concentration/concentration range of one or more nutrients, a suitable level of metabolic waste/metabolites, among others. A person of ordinary skill in the art, upon reviewing the entirety of this disclosure, will be able to identify suitable conditions specific to one or more microbes described herein.

Figure 5:
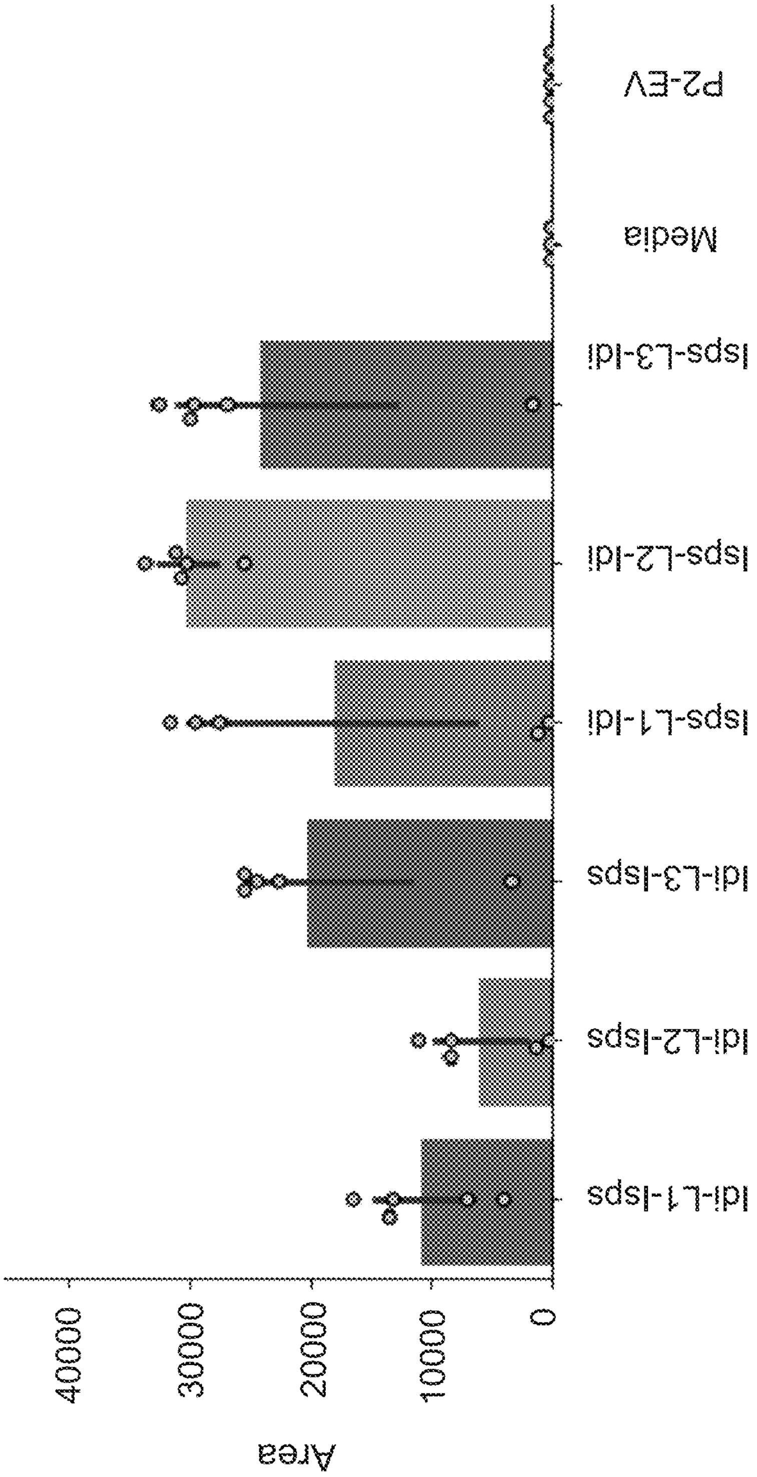
FIG. 5 is an exemplary experimental result of isoprene production for IDI and IspS fusion, media only, and empty vector (P1+P2 system without IspS) control.

With continued reference to FIG. 4, at step 410, method further includes providing substrate to genetically engineered microbe to produce isoprene, consistent with details described above without limitation. Specifically, first binding site is configured to bind to substrate and catalyze first chemical reaction that converts the substrate to intermediate. Similarly, second binding site is configured to catalyze second chemical reaction that converts intermediate to isoprene. In some cases, produced isoprene may be isolated and/or purified using an absorbing/stripping apparatus, consistent with details disclosed in U.S. patent application Ser. No. 18/928,691, filed on Oct. 28, 2024, entitled "SYSTEMS AND METHODS FOR PRODUCING A DIMETHYLCYCLOOCTANE-BASED AVIATION FUEL FROM ISOPRENE", the entirety of which is incorporated herein by reference With continued reference to FIG. 5, exemplary experimental result of isoprene production for IDI and IspS fusion, media only, empty vector (P1+P2 system without IspS) control is illustrated. The x-axis represents six IDI and IspS fusion construct design along with media only control, and empty vector control (P1+P2 system without IspS). The y-axis represents isoprene production detected by area using gas chromatography. All fusion constructs produced isoprene. Each IspS_IDI construct produced more isoprene than its reversed counterpart, IDI_IspS. In the IDI_IspS orientation (IDI_Linker1_IspS, SEQ: 1; IDI_Linker2_IspS, SEQ: 3; IDI_Linker3_IspS, SEQ: 5) the linker 2 (SEQ: 28) construct (flexible linker) produced most isoprene. In the IspS_IDI orientation (IspS_Linker1_IDI, SEQ: 13; IspS_Linker2_IDI, SEQ: 15; IspS_Linker3_IDI, SEQ: 17), the linker 3 (SEQ: 29) construct (rigid linker) produced the most isoprene.

Figure 6:
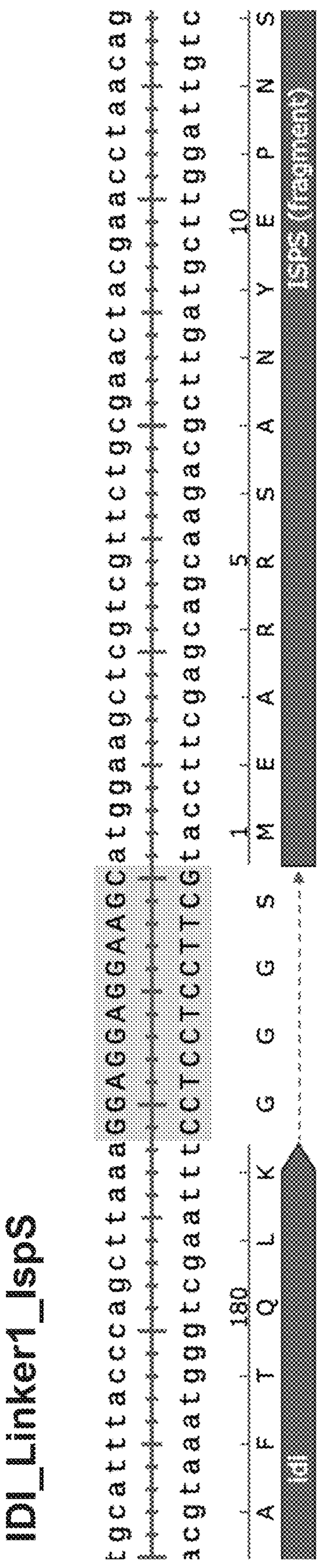
FIG. 6 is an exemplary result of the fusion construct containing the IDI_Linker2_IspS sequence

With continued reference to FIG. 6, exemplary result of the fusion construct containing the IDI_Linker1_IspS sequence is illustrated. Linker 1 (Ec-Idi Linker-1 Pa-IspS, SEQ: 1; Linker 1, SEQ: 27) has an amino acid sequence of "GGGS," wherein G is glycine and S is serine. In the construct, the IDI sequence begins at the N-terminal, and the IspS sequence terminates at the C-terminal. Linker 1 (SEQ: 27) provides flexibility between the two enzyme domains.

Figure 7:
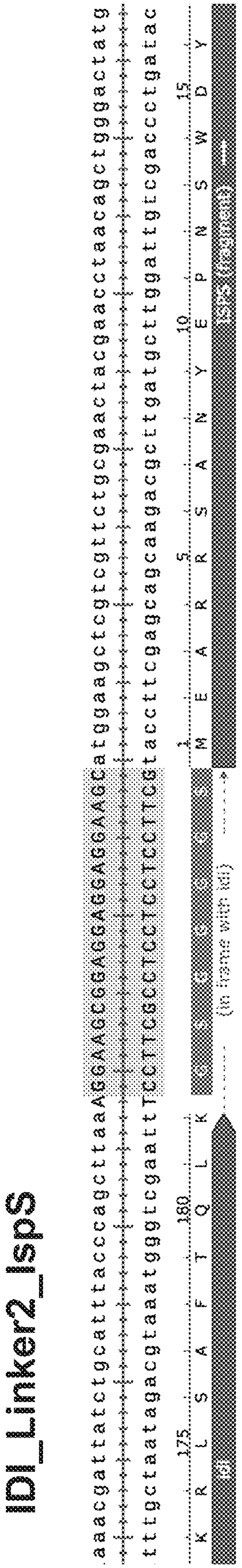
FIG. 7 is an exemplary result of the fusion construct containing the IDI_Linker2_IspS sequence.

With continued reference to FIG. 7, exemplary result of the fusion construct containing the IDI_Linker2_IspS sequence is illustrated. Linker 2 (Ec-Idi Linker-2 Pa-IspS, SEQ: 3; Linker 2, SEQ: 28) has an amino acid sequence of "GSGGGGS," wherein G is glycine and S is serine. In the construct, the IDI sequence begins at the N-terminal, and the IspS sequence terminates at the C-terminal. Linker 2 (SEQ: 28) provides flexibility between the two enzyme domains.

Figure 8:
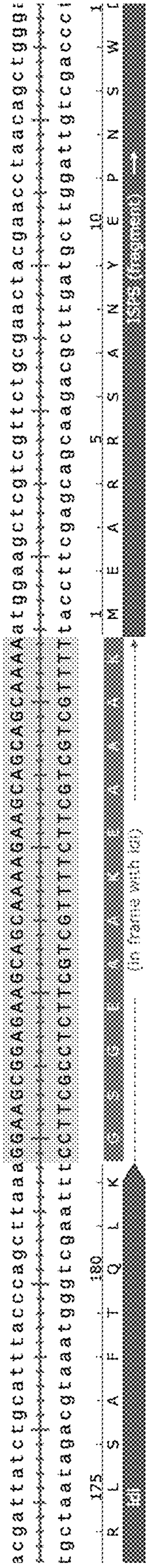
FIG. 8 is an exemplary result of the fusion construct containing the IDI_Linker3_IspS sequence.

With continued reference to FIG. 8, exemplary result of the fusion construct containing the IDI_Linker3_IspS sequence is illustrated. Linker 3 (Ec-Idi Linker-3 Pa-IspS, SEQ: 5; Linker 3, SEQ: 29) has an amino acid sequence of "GSGEAAKEAAAK," wherein G is glycine, S is serine, E is glutamic acid, A is alanine, and K is lysine. In the construct, the IDI sequence begins at the N-terminal, and the IspS sequence terminates at the C-terminal. Linker 3 (SEQ: 29) imparts rigidity between the two enzyme domains, as the residues glutamic acid, alanine, and lysine promote alpha-helical geometry in the linker region, thereby limiting domain flexibility.

Figure 9:
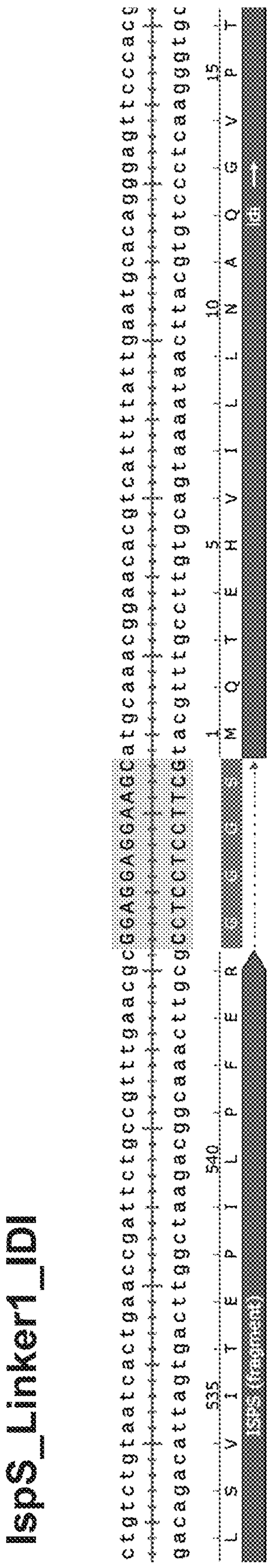
FIG. 9 is an exemplary result of the fusion construct containing the IspS_Linker1_IDI sequence.

With continued reference to FIG. 9, exemplary result of the fusion construct containing the IspS_Linker1_IDI sequence is illustrated. Linker 1 (Pa-IspS Linker-1 Ec-Idi, SEQ: 13; Linker 1, SEQ: 27) has an amino acid sequence of "GGGS," wherein G is glycine and S is serine. In the construct, the IspS sequence begins at the N-terminal, and the IDI sequence terminates at the C-terminal. Linker 1 (SEQ: 27) provides flexibility between the two enzyme domains.

Figure 10:
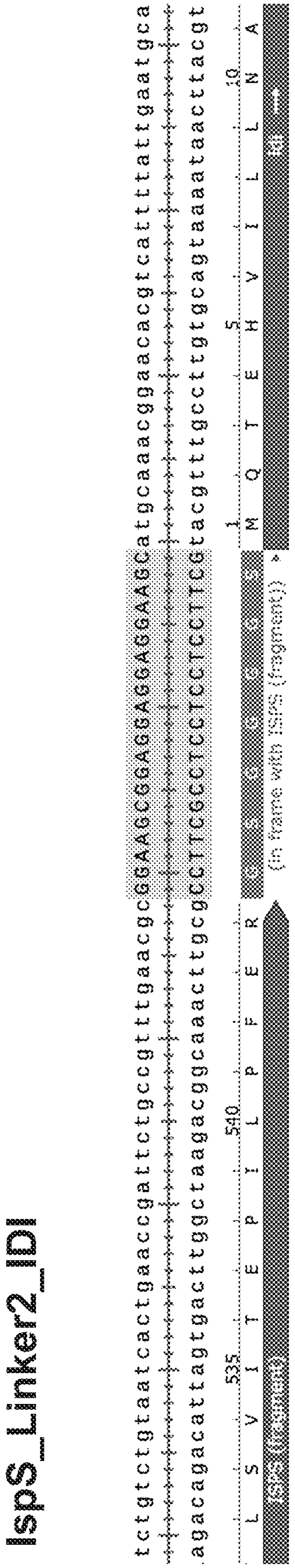
FIG. 10 is an exemplary result of the fusion construct containing the IspS_Linker2_ID sequence.

With continued reference to FIG. 10, exemplary result of the fusion construct containing the IspS_Linker2_IDI sequence is illustrated. Linker 2 (Pa-IspS Linker-2 Ec-Idi, SEQ: 15; Linker 2, SEQ: 28) has an amino acid sequence of "GSGGGGS," wherein G is glycine and S is serine. In the construct, the IspS sequence begins at the N-terminal, and the IDI sequence terminates at the C-terminal. Linker 2 (SEQ: 28) provides flexibility between the two enzyme domains.

Figure 11:
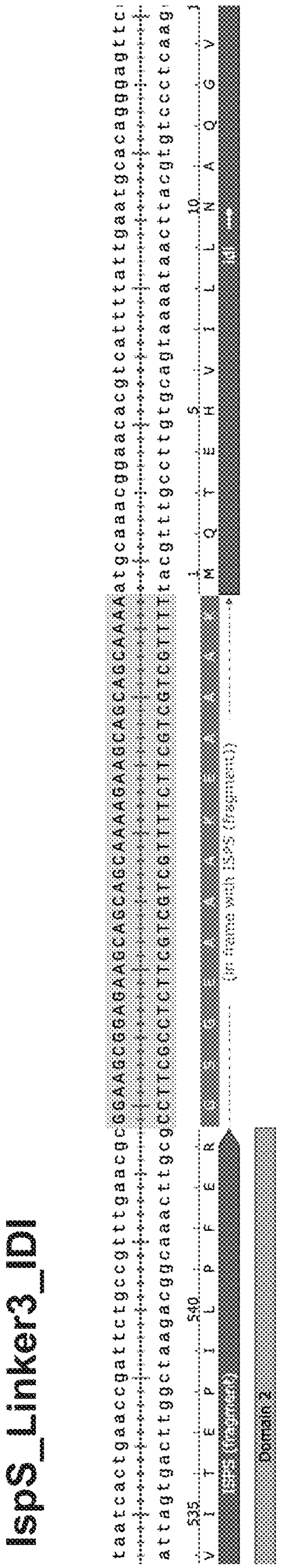
FIG. 11 is exemplary result of the fusion construct containing the IspS_Linker3_ID sequence.

With continued reference to FIG. 11, exemplary result of the fusion construct containing the IspS_Linker3_IDI sequence is illustrated. Linker 3 (Pa-IspS Linker-3 Ec-Idi, SEQ: 17; Linker 3, SEQ: 29) has an amino acid sequence of "GSGEAAKEAAAK," wherein G is glycine, S is serine, E is glutamic acid, A is alanine, and K is lysine. In the construct, the IspS sequence begins at the N-terminal, and the IDI sequence terminates at the C-terminal. Linker 3 (SEQ: 29) imparts rigidity between the two enzyme domains, as the residues glutamic acid, alanine, and lysine promote alpha-helical geometry in the linker region, thereby limiting domain flexibility.

Figure 12A:
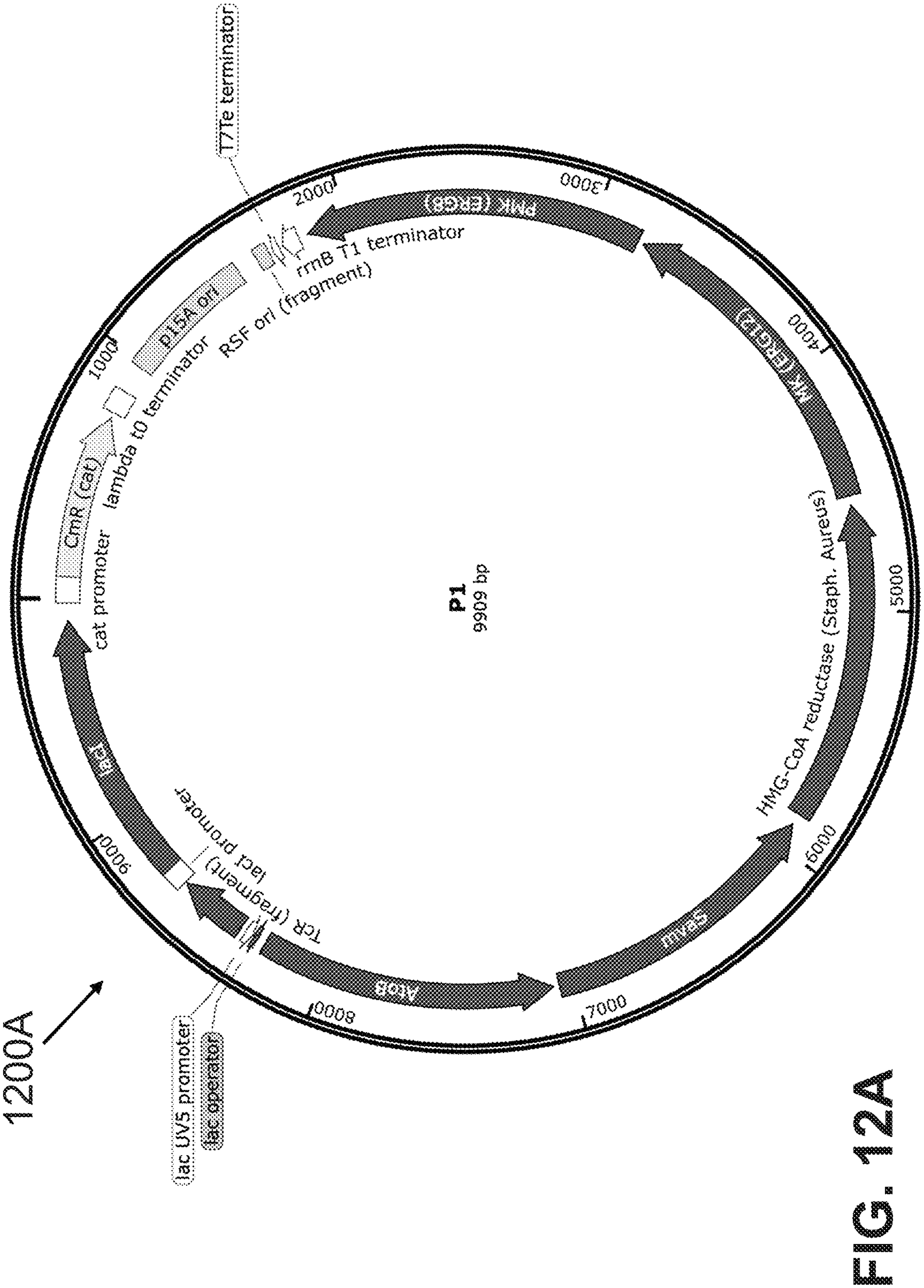
FIGS. 12A-B are exemplary embodiments of plasmid vector maps used for P1+P2 systems. The drawings are not necessarily to scale and may be illustrated by phantom lines, diagrammatic representations and fragmentary views. In certain instances, details that are not necessary for an understanding of the embodiments or that render other details difficult to perceive may have been omitted.
Figure 12B:
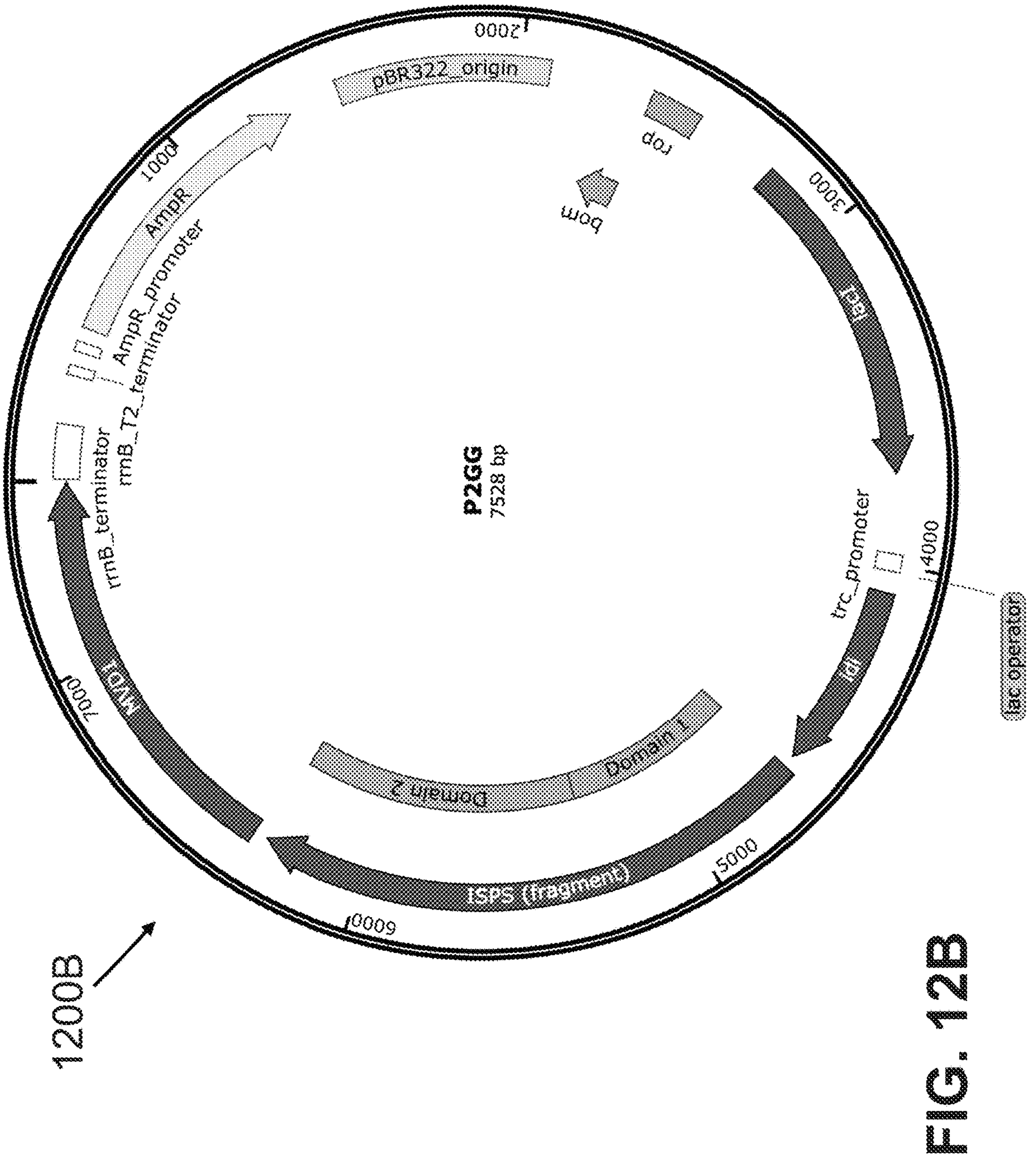

With continued reference to FIGS. 12A-B, exemplary embodiments of plasmid vector maps used for P1+P2 systems are illustrated. P1+P2 system includes two plasmids: P1 system (1200A) (P1 System, SEQ: 32) and P2 system (1200B) (P2 system, SEQ: 33) that contain genes to encode all the enzymes in the MVA pathway. P1 plasmid (1200B) encode enzymes to be heterologously expressed in upper mevalonate pathway in *E. coli*. The genes AtoB, MvaS, HMGR, MK (ERG12), and PMK (ERG8) are encoded on the plasmid P1 (1200A), and translate the proteins acetyl-coA acetyltransferase, HMG-COA synthase, HMG-COA reductase, mevalonate kinase, and phosphomevalonate kinase respectively. The genes encoded by P1 are under control of the lacUV5 promoter. The P1 plasmid (1200A) as a p15A origin of replication and a chloramphenicol resistance marker. The P2 plasmid (1200B) includes of the genes idi, IspS and MVD1, when encode isopentenyl diphosphate isomerase, isoprene synthase and mevalonate decarboxylase respectively. P2 plasmid (1200B) and P2GG plasmid (P2GG system, SEQ: 34) encod the enzymes to be heterologoulsly expressed in the lower mevalonate pathway in *E. coli*. The P2 plasmid (1200B) was modified to simplify downstream cloning by removal of BsaI restriction sites to yield the P2GG plasmid. The P2GG plasmid encodes the same genes as P2, which in both cases are under control of the Trc promoter. Both P2 and P2GG have a pBR332 origin of replication and an ampicillin resistance marker.

EXAMPLES

Example 1: Identify Chassis for Production of Isoprene and Improve Productivity and Yield of Isoprene in *E. coli*

Purpose of the Study

This study investigates the amount of isoprene produced by the IspS_IDI fusion construct using recombinant DNA techniques, and examines how different linkers and orientations of the fusion construct impact isoprene production.

INTRODUCTION

Isopentyl diphosphate isomerase (IDI) and Isoprene synthase (IspS) are the two final enzymes in the mevalonate (MVA) pathway for isoprene synthesis and in the pathway contained in the P1+P2 plasmid system used by CLEANJOULE to investigate pathway improvement at this time. The P1+P2 system includes two plasmids (P1 and P2 respectively) that contain genes to encode all the enzymes in the MVA pathway. The genes AtoB, MvaS, HMGR, MK (ERG12), and PMK (ERG8) are encoded on the plasmid P1, and translate the proteins acetyl-coA acetyltransferase, HMG-COA synthase, HMG-COA reductase, mevalonate kinase, and phosphomevalonate kinase respectively. The genes encoded by P1 are under control of the lacUV5 promoter. The P1 plasmid as a p15A origin of replication and a chloramphenicol resistance marker. The P2 plasmid includes of the genes idi, IspS and MVD1, when encode isopentenyl diphosphate isomerase, isoprene synthase and mevalonate decarboxylase respectively. The P2 plasmid was modified to simplify downstream cloning by removal of BsaI restriction sites to yield the P2GG plasmid. The P2GG plasmid encodes the same genes as P2, which in both cases are under control of the Trc promoter. Both P2 and P2GG have a pBR332 origin of replication and an ampicillin resistance marker. We hypothesize that fusions of IspS and IDI will improve pathway flux at their respective steps because they are involved in sequential steps in the pathway, and that could allow the fusion protein to be more closely associate with its sequential substrates.

SUMMARY OF STUDY

Six enzyme-linker constructs were designed and produced detectable levels of isoprene. Each IspS_IDI construct generated more isoprene than its reversed counterpart, IDI_IspS.

Strategies

For our case, three linker sequences were chosen: the first two are short and long GS linkers (flexible) and the third is an EAAAK linker (rigid). The sequences for Linker 1, Linker 2, and Linker 3 are GGGS, GSGGGGS, and GSGEAAAKEAAAK, respectively.

The fusions of IDI and IspS are detailed in Table 2. Fusion proteins were created using the P2 plasmid as a template, where IDI and IspS nucleotide sequences were replaced by the fusion protein sequence and appropriate ribosome binding site (RBS) with the stop codon at the end of the first protein omitted while preserving the start codon at the start of the second protein in the sequence.

TABLE 2

Fusion Constructs & Construction Details

| Fusion | Order (N to C) | SnapGene File | Sequencing Verification# | Glycerol Stock # |
|---|---|---|---|---|
| L0[4] | IDI_Linker1_IspS | P2_Fusion.dna | 2272821 (Eurofins) | s56.1 (P2 Fusion) |
| L1[5] | IDI_Linker2_IspS | AZ821_L1_Assembly.dna | 52FZ9Q (Plasmidsaurus) | A7.8 |
| L2[5] | IDI_Linker3_IspS | AZ821-L2-Assembly.dna | 2FVJ3W (Plasmidsaurus) | A8.16 |
| L3[6] | IspS_Linker1_IDI | P2_IspS-Linker_1-Idi.dna | 373BFW (Plasmidsaurus) | A9.1, A9.2 |
| L4[6] | IspS_Linker2_IDI | P2_IspS-Linker_2-Idi.dna | 373BFW (Plasmidsaurus) | A10.1, A10.2 |
| L5[6] | IspS_Linker3_IDI | P2_IspS-Linker_3-Idi.dna | 373BFW (Plasmidsaurus) | A11.2 |

All fusion constructs produced isoprene. Each IspS_IDI construct produced more isoprene than its reversed counterpart, IDI_IspS. In the IDI_IspS orientation, the Linker 2 construct (flexible) produced most isoprene. In the IspS_IDI orientation, the Linker 3 construct (rigid) produced the most isoprene.

CONCLUSION

All IspS_IDI fusion constructs produced isoprene.

Materials & Methods

Cloning

P2GG was amplified at IDI using primers designed for domesticated golden gate assembly. Each pair of primers contains a BsaI restriction site, a complimentary overhang to the adjacent segment, the appropriate linker sequence, and a complimentary annealing region. L0 was previously constructed. L3-5 were assembled by amplifying the whole backbone from P2GG with primers that contained the linker sequences and performing a Golden-Gate mediated self-ligation. Self-ligation failed for the construction of L1 and L2, and primers were redesigned to construct L1 and L2 through golden-gate mediated 2-fragment assembly. The assembled products were transformed into DH5-alpha competent cells and colonies were screened by colony PCR. Successful colonies were sequence verified. Glycerol stocks are available for all constructs (see Table 2 for strain codes).

Expression

Plasmids containing each of the fusion combinations mentioned above were transformed into BL21 (DE3) competent cells along with P1. Colonies were then selected and grown in liquid culture (2 mL LB+100 μg/mL Carbenicillin+35 g/mL Chloramphenicol+10 g/L glucose) at 37° C. until the OD was approximately 0.6. At this point, 790 μL of the cells were transferred to autosampler vials and induced by addition of 7.9 μL of 100 mM IPTG. The tubes were then sealed and incubated at 30° C. for roughly 48 hours, at which point the headspace from the tubes was sampled and analyzed by GC-FID with the autosampler program H-Isoprene-1 Method. A single expression experiment was performed with 5 biological replicates for each sample. Expression data is in Table 3.

TABLE 3

| Expression Details | | | | | | | |
|---|---|---|---|---|---|---|---|
| Sample # | Sample Label | RT | Width | Area | Height | Area % | Induction O.D. |
| 1 | P2-EV | 1.02 | 0.051 | 128 | 41 | 100 | 0.6 |
| 2 | P2-EV | 1.02 | 0.054 | 116 | 36 | 100 | 0.5 |
| 3 | P2-EV | 1.02 | 0.054 | 137 | 43 | 100 | 0.8 |
| 4 | P2-EV | 1.02 | 0.052 | 154 | 49 | 100 | 0.6 |
| 5 | P2-EV | 1.02 | 0.054 | 169 | 51 | 100 | 0.6 |
| 6 | Idi-L1-IspS | 1.03 | 0.051 | 16378 | 5381 | 100 | 0.9 |
| 7 | Idi-L1-IspS | 1.03 | 0.051 | 13218 | 4339 | 100 | 0.7 |
| 8 | Idi-L1-IspS | 1.03 | 0.051 | 13467 | 4425 | 100 | 0.7 |
| 9 | Idi-L1-IspS | 1.03 | 0.051 | 7013 | 2307 | 100 | 0.6 |
| 10 | Idi-L1-IspS | 1.03 | 0.05 | 3986 | 1316 | 100 | 0.7 |
| 11 | Idi-L2-IspS | 1.02 | 0.051 | 260 | 81 | 100 | 0.6 |
| 12 | Idi-L2-IspS | 1.03 | 0.051 | 1384 | 451 | 100 | 0.7 |
| 13 | Idi-L2-IspS | 1.03 | 0.051 | 8416 | 2759 | 100 | 0.6 |
| 14 | Idi-L2-IspS | 1.03 | 0.051 | 11066 | 3637 | 100 | 0.6 |
| 15 | Idi-L2-IspS | 1.03 | 0.051 | 8482 | 2785 | 100 | 0.5 |

TABLE 3-continued

| Expression Details | | | | | | | |
|---|---|---|---|---|---|---|---|
| Sample # | Sample Label | RT | Width | Area | Height | Area % | Induction O.D. |
| 16 | Idi-L3-IspS | 1.03 | 0.051 | 25576 | 8414 | 100 | 0.7 |
| 17 | Idi-L3-IspS | 1.03 | 0.051 | 3305 | 1080 | 100 | 0.6 |
| 18 | Idi-L3-IspS | 1.03 | 0.051 | 24381 | 8010 | 100 | 1 |
| 19 | Idi-L3-IspS | 1.03 | 0.051 | 22584 | 7432 | 100 | 0.6 |
| 20 | Idi-L3-IspS | 1.03 | 0.051 | 25467 | 8376 | 100 | 0.6 |
| 21 | IspS-L1-Idi | 1.02 | 0.052 | 308 | 97 | 100 | 0.6 |
| 22 | IspS-L1-Idi | 1.03 | 0.051 | 31702 | 10394 | 100 | 0.6 |
| 23 | IspS-L1-Idi | 1.03 | 0.051 | 27533 | 9032 | 100 | 0.6 |
| 24 | IspS-L1-Idi | 1.03 | 0.051 | 1164 | 378 | 100 | 0.5 |
| 25 | IspS-L1-Idi | 1.03 | 0.051 | 29508 | 9700 | 100 | 0.7 |
| 26 | IspS-L2-Idi | 1.03 | 0.051 | 25509 | 8354 | 100 | 0.6 |
| 27 | IspS-L2-Idi | 1.03 | 0.05 | 31208 | 10283 | 100 | 0.5 |
| 28 | IspS-L2-Idi | 1.03 | 0.051 | 30778 | 10127 | 100 | 0.5 |
| 29 | IspS-L2-Idi | 1.03 | 0.051 | 30309 | 9959 | 100 | 0.6 |
| 30 | IspS-L2-Idi | 1.03 | 0.051 | 33686 | 11061 | 100 | 0.5 |
| 31 | IspS-L3-Idi | 1.03 | 0.051 | 26869 | 8827 | 100 | 1 |
| 32 | IspS-L3-Idi | 1.03 | 0.051 | 29611 | 9719 | 100 | 0.9 |
| 33 | IspS-L3-Idi | 1.03 | 0.051 | 1746 | 569 | 100 | 0.8 |
| 34 | IspS-L3-Idi | 1.03 | 0.051 | 29958 | 9835 | 100 | 1.1 |
| 35 | IspS-L3-Idi | 1.03 | 0.051 | 32668 | 10741 | 100 | 0.9 |
| M1 | Media | 1.02 | 0.052 | 145 | 46 | 100 | 0.1 |
| M2 | Media | 1.02 | 0.052 | 139 | 44 | 100 | 0.2 |
| M3 | Media | 1.02 | 0.053 | 141 | 44 | 100 | 0.2 |
| AIR | Air | 0 | 0 | 0 | 0 | 0 | — |

Fusion Construct Construction

All fusion constructs utilize the Trc promoter. The rrnB and rrnB_T2 terminators were used, terminating transcription after MVD1. The genes IDI, IspS, and MVD1 are arranged in a polycistronic configuration and are all transcribed under the control of the Trc promoter located upstream of IDI.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A genetically engineered microbe capable of producing isoprene, the genetically engineered microbe comprises:

a heterologous nucleic acid construct encoding at least a portion of a peptide superstructure, wherein the superstructure comprises:

a first portion comprising a first binding site configured to catalyze a first chemical reaction, wherein the first reaction converts a substrate to an intermediate; and a second portion comprising a second binding site configured to catalyze a second chemical reaction, wherein:

the second portion is covalently linked to the first portion through a linker; and the second chemical reaction converts the intermediate to isoprene; and wherein:

the first portion comprises isopentenyl diphosphate (IPP) isomerase comprising a sequence of SEQ ID NO: 30 or SEQ ID NO: 31 or enzymatically active fragment thereof; and the second portion comprises isoprene synthase (IspS) comprising a sequence of SEQ ID NO: 25 or SEQ ID NO: 26, or enzymatically active fragment thereof.

2. The genetically engineered microbe of claim 1, wherein:

the substrate comprises IPP; and the intermediate comprises dimethylallyl pyrophosphate (DMAPP).

3. The genetically engineered microbe of claim 1, wherein the genetically engineered microbe comprises bacteria or fungi, wherein the bacteria or fungi includes one or more members selected from a group consisting of *Escherichia Coli, Lactococcus, Vibrio natriegens, Saccharomyces cerevisiae, Aspergillus, Yarrowia lipolytica, Bacillus subtilis, Clostridium ljungdahlii*, and *Pseudomonas putid.*

4. The genetically engineered microbe of claim 1, wherein the genetically engineered microbe comprises a Crabtree-negative microbe.

5. The genetically engineered microbe of claim 1, wherein the genetically engineered microbe comprises a diploid strain.

* * * * *

SEQUENCE LISTING

```
Sequence total quantity: 34
SEQ ID NO: 1            moltype = DNA  length = 2191
FEATURE                 Location/Qualifiers
source                  1..2191
                        mol_type = other DNA
                        organism = synthetic construct
```

-continued

```
SEQUENCE: 1
atgcaaacgg aacacgtcat tttattgaat gcacagggag ttcccacggg tacgctggaa  60
aagtatgccg cacacacggc agacacccgc ttacatctcg cgttctccag ttggctgttt  120
aatgccaaag gacaattatt agttacccgc cgcgcactga gcaaaaaagc atggcctggc  180
gtgtggacta actcggtttg tgggcaccca caactgggag aaagcaacga agacgcagtg  240
atccgccgtt gccgttatga gcttggcgtg gaaattacgc ctcctgaatc tatctatcct  300
gactttcgct accgcgccac cgatccgagt ggcattgtgg aaaatgaagt gtgtccggta  360
tttgccgcac gcaccactag tgcgttacag atcaatgatg atgaagtgat ggattatcaa  420
tggtgtgatt tagcagatgt attacacggt attgatgcca cgccgtgggc gttcagtccg  480
tggatggtga tgcaggcgac aaatcgcgaa gccagaaaac gattatctgc atttacccag  540
cttaaaggag gaggaagcat ggaagctcgt cgttctgcga actacgaacc taacagctgg  600
gactatgatt acctgctgtc ctccgacacg gacgagtcca tcgaagtata caaagacaaa  660
gcgaaaaagc tggaagccga agttcgtcgc gagattaata acgaaaaagc agaatttctg  720
accctgctgg aactgattga caacgtccag cgcctgggcc tgggttaccg tttcgagtct  780
gatatccgtg gtgcgctgga tcgcttcgtt tcctccggcg gcttcgatgc ggtaaccaag  840
acttccctgc acggtacggc actgtctttc cgtctgctgc gtcaacacgg ttttgaggtt  900
tctcaggaag cgttcagcgg cttcaaagac caaaacggca acttcctgga gaacctgaag  960
gaagatatca aagctatcct gagcctgtac gaggccagct tcctggctct ggaaggcgaa  1020
aacatcctgg acgaggcgaa ggttttcgca atctctcatc tgaaagaact gtctgaagaa  1080
aagatcggta aagagctggc agaacaggtg aaccatgcac tggaactgcc actgcatcgc  1140
cgtactcagc gtctggaagc agtatggtct atcgaggcct accgtaaaaa ggaggacgcg  1200
aatcaggttc tgctggagct ggcaattctg gattacaaca tgatccagtc tgtataccag  1260
cgtgatctgc gtgaaacgtc ccgttggtgg cgtcgtgtgg gtctggcgac caaactgcac  1320
tttgctcgtg accgcctgat tgagagcttc tactgggccg tgggtgtagc attcgaaccg  1380
caatactccg actgccgtaa ctccgtcgca aaaatgtttt gtttcgtaac cattatcgac  1440
gatatctacg atgtatacgg caccctggac gaactggagc tgtttactga tgcagttgag  1500
cgttgggacg taaacgccat caacgacctg ccggattaca tgaaactgtg ctttctggct  1560
ctgtataaca ctattaacga aatcgcctac gacaacctga aagataaagg tgagaacatc  1620
ctgccgtatc tgaccaaagc ctgggctgac ctgtgcaacg ctttcctgca agaagccaag  1680
tggctgtaca acaaatctac tccgaccttt gacgactact tcggcaacgc atggaaatcc  1740
tcttctggcc cgctgcaact ggtgttcgct tacttcgctg tcgtgcagaa cattaaaaag  1800
gaagagatcg aaaacctgca aaaataccat gacaccatct ctcgtccttc ccatatcttc  1860
cgtctgtgca atgacctggc tagcgcgtct gcggaaattg cgcgtggtga aaccgcaaat  1920
agcgtttctt gttacatgcg cactaaaggt atctccgaag aactggctac cgaaagcgtg  1980
atgaatctga tcgatgaaac ctggaaaaag atgaacaagg aaaaactgag tggtagcctg  2040
ttcgcgaaac cgttcgtgga aaccgcgatc aacctggcac gtcaatctca ctgcacttat  2100
cataacggcg acgcgcatac ctctccggat gagctgaccc gcaaacgcgt tctgtctgta  2160
atcactgaac cgattctgcc gtttgaacgc t                                 2191

SEQ ID NO: 2            moltype = DNA  length = 2211
FEATURE                 Location/Qualifiers
source                  1..2211
                        mol_type = other DNA
                        organism = synthetic construct
SEQUENCE: 2
atgcaaacgg aacacgtcat tttattgaat gcacagggag ttcccacggg tacgctggaa  60
aagtatgccg cacacacggc agacacccgc ttacatctcg cgttctccag ttggctgttt  120
aatgccaaag gacaattatt agttacccgc cgcgcactga gcaaaaaagc atggcctggc  180
gtgtggacta actcggtttg tgggcaccca caactgggag aaagcaacga agacgcagtg  240
atccgccgtt gccgttatga gcttggcgtg gaaattacgc ctcctgaatc tatctatcct  300
gactttcgct accgcgccac cgatccgagt ggcattgtgg aaaatgaagt gtgtccggta  360
tttgccgcac gcaccactag tgcgttacag atcaatgatg atgaagtgat ggattatcaa  420
tggtgtgatt tagcagatgt attacacggt attgatgcca cgccgtgggc gttcagtccg  480
tggatggtga tgcaggcgac aaatcgcgaa gccagaaaac gattatctgc atttacccag  540
cttaaaggag gaggaagcat gaactcacgt cgttcagcta attatcaacc aaacctctgg  600
aattttgagt ttctgcagag tttggaaaac gaccttaagg ttgagaaact tgaggagaag  660
gcgacgaaac tggaagagga agttcgctgc atgatcaatc gtgtggatac acaacctctg  720
agtttgcttg aactgattga tgacgtgcag agactcggac tgacgtacaa gttcgaaaaa  780
gatatcatca aagctctgga gaatatcgtc cttctggatg agaacaagaa aaataagtca  840
gacttgcacg cgacagcgct gagctttcgt ttattaagac aacacggctt tgaagtgtca  900
caagacgttt ttgagcggtt caaggataag gaggggggtt tcagtgggga actcaagggt  960
gacgtgcaag gactcctcag tctgtacgag gcgagttatc tcgggttcga gggtgagaat  1020
ttattagaag aggcacggac tttttctata acacacttaa aaaataactt gaaagaaggt  1080
ataaacacta aagtcgccga acaggtttca catgctctgg agctccctta tcaccagaga  1140
ctccaccgtc tggaggctcg ttggttcctg gataaatatg aaccgaagga gccacatcat  1200
caacttctgc ttgaattggc taagttagac tttaacatgg ttcagacact gcaccagaag  1260
gaactgcagg acctgtcacg ctggtggact gagatgggtt tagcttccaa gcttgacttc  1320
gttcgtgaca gactcatgga ggtttatttt tgggccttgg gaatggcgcc tgatccgcaa  1380
tttggtgagt gtcggaaagc ggttacgaaa atgttcgggc tggtgaccat tatcgacgac  1440
gtgtatgatg tttatgggac actggatgaa cttcaactct ttacggatgc agtcgaacgc  1500
tgggatgtga atgcgataaa caccctccct gattacatga aattgtgctt tttagcgctc  1560
tataatactg ttaacgatac atcctactca atcctcaaag aaaaaggaca caataacctt  1620
agttatctta ctaaatcttg gcgcgagctg tgcaaggcct tcctgcagga agctaaatgg  1680
agtaataaca agataattcc tgcatttagc aagtacttgg aaaatgcaag tgtaagttct  1740
tccggtgtag ctttgctcgc cccaagctac ttctcagtat gtcaacagca ggaggatatt  1800
agtgaccatg cgcttcgcag tttgacggac ttccacggac tcgtccgctc ttcatgcgta  1860
attttccgtt tgtgcaacga tctggccacc agcgcggccg agttggagcg tggagaaacg  1920
actaatagca tcataagcta tatgcatgaa aatgacggaa catccgaaga gcaagcacgt  1980
gaagagctcc ggaagcttat agacgcagaa tggaagaaga tgaaccggga gcgcgtatca  2040
```

```
gatagtaccc tcttaccaaa ggcttttatg gaaattgcgg tgaatatggc gcgcgtatcc  2100
cattgtactt accaatatgg ggacggcttg ggacgtcctg attatgcgac agagaatcgg  2160
attaaattat tgttaatcga cccattccca atcaatcaac tgatgtacgt a           2211

SEQ ID NO: 3            moltype = DNA  length = 2200
FEATURE                 Location/Qualifiers
source                  1..2200
                        mol_type = other DNA
                        organism = synthetic construct
SEQUENCE: 3
atgcaaacgg aacacgtcat tttattgaat gcacagggag ttcccacggg tacgctggaa  60
aagtatgccg cacacacggc agacacccgc ttacatctcg cgttctccag ttggctgttt  120
aatgccaaag gacaattatt agttacccgc cgcgcactga gcaaaaaagc atggcctggc  180
gtgtggacta actcggtttg tggcacccca caactgggag aaagcaacga agacgcagtg  240
atccgccgtt gccgttatga gcttggcgtg gaaattacgc ctcctgaatc tatctatcct  300
gactttcgct accgcgccac cgatccgagt ggcattgtgg aaaatgaagt gtgtccggta  360
tttgccgcac gcaccactag tgcgttacag atcaatgatg atgaagtgat ggattatcaa  420
tggtgtgatt tagcagatgt attacacggt attgatgcca cgccgtgggc gttcagtccg  480
tggatggtga tgcaggcgac aaatcgcgaa gccagaaaac gattatctgc atttacccag  540
cttaaaggaa gcggaggagg aggaagcatg gaagctcgtc gttctgcgaa ctacgaacct  600
aacagctggg actatgatta cctgctgtcc tccgacacgg acgagtccat cgaagtatac  660
aaagacaaag cgaaaaagct ggaagccgaa gttcgtcgcg agattaataa cgaaaaagca  720
gaatttctga ccctgctgga actgattgac aacgtccagc gcctgggcct gggttaccgt  780
ttcgagtctg atatccgtgg tgcgctggat cgcttcgttt cctccggcgg cttcgatgcg  840
gtaaccaaga cttccctgca cggtacggca ctgtctttcc gtctgctgcg tcaacacggt  900
tttgaggttt ctcaggaagc gttcagcggc ttcaaagacc aaaacggcaa cttcctggag  960
aacctgaagg aagatatcaa agctatcctg agcctgtacg aggccagctt cctggctctg  1020
gaaggcgaaa acatcctgga cgaggcgaag gttttcgcaa tctctcatct gaaagaactg  1080
tctgaagaaa agatcggtaa agagctggca gaacaggtga accatgcact ggaactgcca  1140
ctgcatcgcc gtactcagcg tctggaagca gtatggtcta tcgaggccta ccgtaaaaag  1200
gaggacgcga atcaggttct gctggagctg gcaattctgg attacaacat gatccagtct  1260
gtataccagc gtgatctgcg tgaaacgtcc cgttggtggc gtcgtgtggg tctggcgacc  1320
aaactgcact ttgctcgtga ccgcctgatt gagagcttct actgggccgt gggtgtagca  1380
ttcgaaccgc aatactccga ctgccgtaac tccgtcgcaa aaatgttttg tttcgtaacc  1440
attatcgacg atatctacga tgtatacggc accctggacg aactggagct gtttactgat  1500
gcagttgagc gttgggacgt aaacgccatc aacgacctgc cggattacat gaaactgtgc  1560
tttctggctc tgtataacac tattaacgaa atcgcctacg acaacctgaa agataaaggt  1620
gagaacatcc tgccgtatct gaccaaagcc tgggctgacc tgtgcaacgc tttcctgcaa  1680
gaagccaagt ggctgtacaa caaatctact ccgacctttg acgactactt cggcaacgca  1740
tggaaatcct cttctggccc gctgcaactg gtgttcgctt acttcgctgt cgtgcagaac  1800
attaaaaagg aagagatcga aaacctgcaa aaataccatg acaccatctc tcgtccttcc  1860
catatcttcc gtctgtgcaa tgacctggct agcgcgtctg cggaaattgc gcgtggtgaa  1920
accgcaaata gcgtttcttg ttacatgcgc actaaaggta tctccgaaga actggctacc  1980
gaaagcgtga tgaatctgat cgatgaaacc tggaaaaaga tgaacaagga aaaactgagt  2040
ggtagcctgt tcgcgaaacc gttcgtggaa accgcgatca acctggcacg tcaatctcac  2100
tgcacttatc ataacggcga cgcgcatacc tctccggatg agctgacccg caaacgcgtt  2160
ctgtctgtaa tcactgaacc gattctgccg tttgaacgct                        2200

SEQ ID NO: 4            moltype = DNA  length = 2220
FEATURE                 Location/Qualifiers
source                  1..2220
                        mol_type = other DNA
                        organism = synthetic construct
SEQUENCE: 4
atgcaaacgg aacacgtcat tttattgaat gcacagggag ttcccacggg tacgctggaa  60
aagtatgccg cacacacggc agacacccgc ttacatctcg cgttctccag ttggctgttt  120
aatgccaaag gacaattatt agttacccgc cgcgcactga gcaaaaaagc atggcctggc  180
gtgtggacta actcggtttg tggcacccca caactgggag aaagcaacga agacgcagtg  240
atccgccgtt gccgttatga gcttggcgtg gaaattacgc ctcctgaatc tatctatcct  300
gactttcgct accgcgccac cgatccgagt ggcattgtgg aaaatgaagt gtgtccggta  360
tttgccgcac gcaccactag tgcgttacag atcaatgatg atgaagtgat ggattatcaa  420
tggtgtgatt tagcagatgt attacacggt attgatgcca cgccgtgggc gttcagtccg  480
tggatggtga tgcaggcgac aaatcgcgaa gccagaaaac gattatctgc atttacccag  540
cttaaaggaa gcggaggagg aggaagcatg aactcacgtc gttcagctaa ttatcaacca  600
aacctctgga attttgagtt tctgcagagt ttggaaaacg accttaaggt tgagaaactt  660
gaggagaagg cgacgaaact ggaagaggaa gttcgctgca tgatcaatcg tgtggataca  720
caacctctga gtttgcttga actgattgat gacgtgcaga gactcggact gacgtacaag  780
ttcgaaaaag atatcatcaa agctctggag aatatcgtcc ttctggatga gaacaagaaa  840
aataagtcag acttgcacgc gacagcgctg agctttcgtt tattaagaca acacggcttt  900
gaagtgtcac aagacgtttt tgagcggttc aaggataagg aggggggttt cagtggggaa  960
ctcaagggtg acgtgcaagg actcctcagt ctgtacgagg cgagttatct cgggttcgag  1020
ggtgagaatt tattagaaga ggcacggact ttttctataa cacacttaaa aaataacttg  1080
aaagaaggta taaacactaa agtcgccgaa caggtttcac atgctctgga gctcccttat  1140
caccagagac tccaccgtct ggaggctcgt tggttcctgg ataaatatga accgaaggag  1200
ccacatcatc aacttctgct tgaattggct aagttagact ttaacatggt tcagacactg  1260
caccagaagg aactgcagga cctgtcacgc tggtggactg agatgggttt agcttccaag  1320
cttgacttcg ttcgtgacag actcatggag gtttattttt gggccttggg aatggcgcct  1380
gatccgcaat ttggtgagtg tcggaaagcg gttacgaaaa tgttcgggct ggtgaccatt  1440
atcgacgacg tgtatgatgt ttatgggaca ctggatgaac ttcaactctt tacggatgca  1500
```

-continued

```
gtcgaacgct gggatgtgaa tgcgataaac accctccctg attacatgaa attgtgcttt  1560
ttagcgctct ataatactgt taacgataca tcctactcaa tcctcaaaga aaaaggacac  1620
aataacctta gttatcttac taaatcttgg cgcgagctgt gcaaggcctt cctgcaggaa  1680
gctaaatgga gtaataacaa gataattcct gcatttagca agtacttgga aaatgcaagt  1740
gtaagttctt ccggtgtagc tttgctcgcc ccaagctact tctcagtatg tcaacagcag  1800
gaggatatta gtgaccatgc gcttcgcagt ttgacggact tccacggact cgtccgctct  1860
tcatgcgtaa ttttccgttt gtgcaacgat ctggccacca gcgcggccga gttggagcgt  1920
ggagaaacga ctaatagcat cataagctat atgcatgaaa atgacggaac atccgaagag  1980
caagcacgtg aagagctccg gaagcttata gacgcagaat ggaagaagat gaaccgggag  2040
cgcgtatcag atagtaccct cttaccaaag gcttttatgg aaattgcggt gaatatggcg  2100
cgcgtatccc attgtactta ccaatatggg gacggcttgg gacgtcctga ttatgcgaca  2160
gagaatcgga ttaaattatt gttaatcgac ccattcccaa tcaatcaact gatgtacgta  2220

SEQ ID NO: 5           moltype = DNA  length = 2218
FEATURE                Location/Qualifiers
source                 1..2218
                       mol_type = other DNA
                       organism = synthetic construct
SEQUENCE: 5
atgcaaacgg aacacgtcat tttattgaat gcacagggag ttcccacggg tacgctggaa  60
aagtatgccg cacacacggc agacacccgc ttacatctcg cgttctccag ttggctgttt  120
aatgccaaag gacaattatt agttacccgc cgcgcactga gcaaaaaagc atggcctggc  180
gtgtggacta actcggtttg tgggcaccca caactgggag aaagcaacga agacgcagtg  240
atccgccgtt gccgttatga gcttggcgtg gaaattacgc ctcctgaatc tatctatcct  300
gactttcgct accgcgccac cgatccgagt ggcattgtgg aaaatgaagt gtgtccggta  360
tttgccgcac gcaccactag tgcgttacag atcaatgatg atgaagtgat ggattatcaa  420
tggtgtgatt tagcagatgt attacacggt attgatgcca cgccgtgggc gttcagtccg  480
tggatggtga tgcaggcgac aaatcgcgaa gccagaaaac gattatctgc atttacccag  540
cttaaaggaa gcggagaagc agcagcaaaa gaagcagcag caaaaatgga agctcgtcgt  600
tctgcgaact acgaacctaa cagctgggac tatgattacc tgctgtcctc cgacacggac  660
gagtccatcg aagtatacaa agacaaagcg aaaaagctgg aagccgaagt tcgtcgcgag  720
attaataacg aaaaagcaga atttctgacc ctgctggaac tgattgacaa cgtccagcgc  780
ctgggcctgg gttaccgttt cgagtctgat atccgtggtg cgctggatcg cttcgtttcc  840
tccggcggct tcgatgcggt aaccaagact tccctgcacg gtacggcact gtctttccgt  900
ctgctgcgtc aacacggttt tgaggtttct caggaagcgt tcagcggctt caaagaccaa  960
aacggcaact tcctggagaa cctgaaggaa gatatcaaag ctatcctgag cctgtacgag  1020
gccagcttcc tggctctgga aggcgaaaac atcctggacg aggcgaaggt tttcgcaatc  1080
tctcatctga aagaactgtc tgaagaaaag atcggtaaag agctggcaga acaggtgaac  1140
catgcactgg aactgccact gcatcgccgt actcagcgtc tggaagcagt atggtctatc  1200
gaggcctacc gtaaaaagga ggacgcgaat caggttctgc tggagctggc aattctggat  1260
tacaacatga tccagtctgt ataccagcgt gatctgcgtg aaacgtcccg ttggtggcgt  1320
cgtgtgggtc tggcgaccaa actgcacttt gctcgtgacc gcctgattga gagcttctac  1380
tgggccgtgg gtgtagcatt cgaaccgcaa tactccgact gccgtaactc cgtcgcaaaa  1440
atgttttgtt tcgtaaccat tatcgacgat atctacgatg tatacggcac cctggacgaa  1500
ctggagctgt ttactgatgc agttgagcgt tgggacgtaa acgccatcaa cgacctgccg  1560
gattacatga aactgtgctt tctggctctg tataacacta ttaacgaaat cgcctacgac  1620
aacctgaaag ataaaggtga gaacatcctg ccgtatctga ccaaagcctg ggctgacctg  1680
tgcaacgctt tcctgcaaga agccaagtgg ctgtacaaca aatctactcc gacctttgac  1740
gactacttcg gcaacgcatg gaaatcctct tctggcccgc tgcaactggt gttcgcttac  1800
ttcgctgtcg tgcagaacat taaaaaggaa gagatcgaaa acctgcaaaa ataccatgac  1860
accatctctc gtccttccca tatcttccgt ctgtgcaatg acctggctag cgcgtctgcg  1920
gaaattgcgc gtggtgaaac cgcaaatagc gtttcttgtt acatgcgcac taaaggtatc  1980
tccgaagaac tggctaccga aagcgtgatg aatctgatcg atgaaacctg gaaaaagatg  2040
aacaaggaaa aactgagtgg tagcctgttc gcgaaaccgt tcgtggaaac cgcgatcaac  2100
ctggcacgtc aatctcactg cacttatcat aacggcgacg cgcatacctc tccggatgag  2160
ctgacccgca aacgcgttct gtctgtaatc actgaaccga ttctgccgtt tgaacgct    2218

SEQ ID NO: 6           moltype = DNA  length = 2238
FEATURE                Location/Qualifiers
source                 1..2238
                       mol_type = other DNA
                       organism = synthetic construct
SEQUENCE: 6
atgcaaacgg aacacgtcat tttattgaat gcacagggag ttcccacggg tacgctggaa  60
aagtatgccg cacacacggc agacacccgc ttacatctcg cgttctccag ttggctgttt  120
aatgccaaag gacaattatt agttacccgc cgcgcactga gcaaaaaagc atggcctggc  180
gtgtggacta actcggtttg tgggcaccca caactgggag aaagcaacga agacgcagtg  240
atccgccgtt gccgttatga gcttggcgtg gaaattacgc ctcctgaatc tatctatcct  300
gactttcgct accgcgccac cgatccgagt ggcattgtgg aaaatgaagt gtgtccggta  360
tttgccgcac gcaccactag tgcgttacag atcaatgatg atgaagtgat ggattatcaa  420
tggtgtgatt tagcagatgt attacacggt attgatgcca cgccgtgggc gttcagtccg  480
tggatggtga tgcaggcgac aaatcgcgaa gccagaaaac gattatctgc atttacccag  540
cttaaaggaa gcggagaagc agcagcaaaa gaagcagcag caaaaatgaa ctcacgtcgt  600
tcagctaatt atcaaccaaa cctctggaat tttgagtttc tgcagagttt ggaaaacgac  660
cttaaggttg agaaacttga ggagaaggcg acgaaactgg aagaggaagt tcgctgcatg  720
atcaatcgtg tggatacaca acctctgagt ttgcttgaac tgattgatga cgtgcagaga  780
ctcggactga cgtacaagtt cgaaaaagat atcatcaaag ctctggagaa tatcgtcctt  840
ctggatgaga acaagaaaaa taagtcagac ttgcacgcga cagcgctgag ctttcgttta  900
ttaagacaac acggctttga agtgtcacaa gacgtttttg agcggttcaa ggataaggag  960
```

-continued

```
gggggtttca gtggggaact caagggtgac gtgcaaggac tcctcagtct gtacgaggcg  1020
agttatctcg ggttcgaggg tgagaattta ttagaagagg cacggacttt ttctataaca  1080
cacttaaaaa ataacttgaa agaaggtata aacactaaag tcgccgaaca ggtttcacat  1140
gctctggagc tcccttatca ccagagactc caccgtctgg aggctcgttg gttcctggat  1200
aaatatgaac cgaaggagcc acatcatcaa cttctgcttg aattggctaa gttagacttt  1260
aacatggttc agacactgca ccagaaggaa ctgcaggacc tgtcacgctg gtggactgag  1320
atgggtttag cttccaagct tgacttcgtt cgtgacagac tcatggaggt ttatttttgg  1380
gccttgggaa tggcgcctga tccgcaattt ggtgagtgtc ggaaagcggt tacgaaaatg  1440
ttcgggctgg tgaccattat cgacgacgtg tatgatgttt atgggacact ggatgaactt  1500
caactcttta cggatgcagt cgaacgctgg gatgtgaatg cgataaacac cctccctgat  1560
tacatgaaat tgtgcttttt agcgctctat aatactgtta acgatacatc ctactcaatc  1620
ctcaaagaaa aaggacacaa taaccttagt tatcttacta aatcttggcg cgagctgtgc  1680
aaggccttcc tgcaggaagc taaatggagt aataacaaga taattcctgc atttagcaag  1740
tacttggaaa atgcaagtgt aagttcttcc ggtgtagctt tgctcgcccc aagctacttc  1800
tcagtatgtc aacagcagga ggatattagt gaccatgcgc ttcgcagttt gacggacttc  1860
cacggactcg tccgctcttc atgcgtaatt ttccgtttgt gcaacgatct ggccaccagc  1920
gcggccgagt tggagcgtgg agaaacgact aatagcatca taagctatat gcatgaaaat  1980
gacggaacat ccgaagagca agcacgtgaa gagctccgga agcttataga cgcagaatgg  2040
aagaagatga accgggagcg cgtatcagat agtaccctct taccaaaggc ttttatggaa  2100
attgcggtga atatggcgcg cgtatcccat tgtacttacc aatatgggga cggcttggga  2160
cgtcctgatt atgcgacaga gaatcggatt aaattattgt taatcgaccc attcccaatc  2220
aatcaactga tgtacgta                                                2238
```

```
SEQ ID NO: 7           moltype = DNA  length = 2509
FEATURE                Location/Qualifiers
source                 1..2509
                       mol_type = other DNA
                       organism = synthetic construct
SEQUENCE: 7
atgaccgccg ataataactc tatgcctcac ggggctgtat ccagctacgc gaaattagta  60
caaaatcaga ccccggaaga catcctggag gaattcccag aaatcatccc tttacagcaa  120
cgtcctaaca cacgtagtag tgagacatct aacgatgaaa gcggggaaac ctgcttttct  180
gggcatgacg aggagcagat taagcttatg aacgagaact gcattgtttt ggattgggac  240
gataatgcta tcggagcggg tactaaaaag gtttgccatt taatggagaa tattgaaaaa  300
ggactgctgc atcgcgcgtt ctccgtattc atcttcaatg agcagggtga acttcttttg  360
caacaacgcg ccaccgaaaa gatcacgttc ccagatcttt ggaccaacac gtgttgctca  420
catcctttgt gtatcgacga tgaactggga ttaaagggta agttggacga caagattaag  480
ggagccatca cggctgccgt gcgtaagctt gaccatgagt tgggaattcc cgaagatgaa  540
accaaaaacgc gtggcaagtt ccatttcctg aatcgtatcc attacatggc accttccaat  600
gaaccatggg gtgagcatga aatcgactat attttatttt acaagatcaa tgcgaaagag  660
aaccttaccg tcaacccgaa tgtgaatgag gtccgcgatt tcaaatgggt tagcccaaac  720
gacctgaaaa cgatgtttgc cgatcccagc tacaagttta caccgtggtt taagattatc  780
tgcgagaatt acttgttcaa ttggtgggag cagcttgacg acttatcgga agtagagaat  840
gaccgtcaga tccatcgcat gttaggagga ggaagcatgg aagctcgtcg ttctgcgaac  900
tacgaaccta acagctggga ctatgattac ctgctgtcct ccgacacgga cgagtccatc  960
gaagtataca aagacaaagc gaaaaagctg gaagccgaag ttcgtcgcga gattaataac  1020
gaaaaagcag aatttctgac cctgctggaa ctgattgaca acgtccagcg cctgggcctg  1080
ggttaccgtt tcgagtctga tatccgtggt gcgctggatc gcttcgtttc ctccggcggc  1140
ttcgatgcgg taaccaagac ttccctgcac ggtacggcac tgtctttccg tctgctgcgt  1200
caacacggtt ttgaggtttc tcaggaagcg ttcagcggct tcaaagacca aaacggcaac  1260
ttcctggaga acctgaagga agatatcaaa gctatcctga gcctgtacga ggccagcttc  1320
ctggctctgg aaggcgaaaa catcctggac gaggcgaagg ttttcgcaat ctctcatctg  1380
aaagaactgt ctgaagaaaa gatcggtaaa gagctggcag aacaggtgaa ccatgcactg  1440
gaactgccac tgcatcgccg tactcagcgt ctggaagcag tatggtctat cgaggcctac  1500
cgtaaaaagg aggacgcgaa tcaggttctg ctggagctgg caattctgga ttacaacatg  1560
atccagtctg tataccagcg tgatctgcgt gaaacgtccc gttggtggcg tcgtgtgggt  1620
ctggcgacca aactgcactt tgctcgtgac cgcctgattg agagcttcta ctgggccgtg  1680
ggtgtagcat tcgaaccgca atactccgac tgccgtaact ccgtcgcaaa aatgttttgt  1740
ttcgtaacca ttatcgacga tatctacgat gtatacggca ccctggacga actggagctg  1800
tttactgatg cagttgagcg ttgggacgta aacgccatca acgacctgcc ggattacatg  1860
aaactgtgct ttctggctct gtataacact attaacgaaa tcgcctacga caacctgaaa  1920
gataaaggtg agaacatcct gccgtatctg accaaagcct gggctgacct gtgcaacgct  1980
ttcctgcaag aagccaagtg gctgtacaac aaatctactc cgacctttga cgactacttc  2040
ggcaacgcat ggaaatcctc ttctggcccg ctgcaactgg tgttcgctta cttcgctgtc  2100
gtgcagaaca ttaaaaagga agagatcgaa aacctgcaaa aataccatga caccatctct  2160
cgtccttccc atatcttccg tctgtgcaat gacctggcta gcgcgtctgc ggaaattgcg  2220
cgtggtgaaa ccgcaaatag cgtttcttgt tacatgcgca ctaaaggtat ctccgaagaa  2280
ctggctaccg aaagcgtgat gaatctgatc gatgaaacct ggaaaaagat gaacaaggaa  2340
aaactgagtg gtagcctgtt cgcgaaaccg ttcgtggaaa ccgcgatcaa cctggcacgt  2400
caatctcact gcacttatca taacggcgac gcgcatacct ctccggatga gctgacccgc  2460
aaacgcgttc tgtctgtaat cactgaaccg attctgccgt ttgaacgct             2509
```

```
SEQ ID NO: 8           moltype = DNA  length = 2529
FEATURE                Location/Qualifiers
source                 1..2529
                       mol_type = other DNA
                       organism = synthetic construct
SEQUENCE: 8
atgaccgccg ataataactc tatgcctcac ggggctgtat ccagctacgc gaaattagta  60
```

-continued

```
caaaatcaga ccccggaaga catcctggag gaattcccag aaatcatccc tttacagcaa  120
cgtcctaaca cacgtagtag tgagacatct aacgatgaaa gcggggaaac ctgcttttct  180
gggcatgacg aggagcagat taagcttatg aacgagaact gcattgtttt ggattgggac  240
gataatgcta tcggagcggg tactaaaaag gtttgccatt taatggagaa tattgaaaaa  300
ggactgctgc atcgcgcgtt ctccgtattc atcttcaatg agcagggtga acttcttttg  360
caacaacgcg ccaccgaaaa gatcacgttc ccagatcttt ggaccaacac gtgttgctca  420
catcctttgt gtatcgacga tgaactggga ttaaagggta agttggacga caagattaag  480
ggagccatca cggctgccgt gcgtaagctt gaccatgagt tgggaattcc cgaagatgaa  540
accaaaacgc gtggcaagtt ccatttcctg aatcgtatcc attacatggc accttccaat  600
gaaccatggg gtgagcatga aatcgactat attttatttt acaagatcaa tgcgaaagag  660
aaccttaccg tcaacccgaa tgtgaatgag gtccgcgatt tcaaatgggt tagcccaaac  720
gacctgaaaa cgatgtttgc cgatcccagc tacaagttta caccgtggtt taagattatc  780
tgcgagaatt acttgttcaa ttggtgggag cagcttgacg acttatcgga agtagagaat  840
gaccgtcaga tccatcgcat gttaggagga ggaagcatga actcacgtcg ttcagctaat  900
tatcaaccaa acctctggaa ttttgagttt ctgcagagtt tggaaaacga ccttaaggtt  960
gagaaacttg aggagaaggc gacgaaactg gaagaggaag ttcgctgcat gatcaatcgt  1020
gtggatacac aacctctgag tttgcttgaa ctgattgatg acgtgcagag actcggactg  1080
acgtacaagt tcgaaaaaga tatcatcaaa gctctggaga atatcgtcct tctggatgag  1140
aacaagaaaa ataagtcaga cttgcacgcg acagcgctga gctttcgttt attaagacaa  1200
cacggctttg aagtgtcaca agacgttttt gagcggttca aggataagga gggggggtttc  1260
agtggggaac tcaagggtga cgtgcaagga ctcctcagtc tgtacgaggc gagttatctc  1320
gggttcgagg gtgagaattt attagaagag gcacggactt tttctataac acacttaaaa  1380
aataacttga aagaaggtat aaacactaaa gtcgccgaac aggtttcaca tgctctggag  1440
ctcccttatc accagagact ccaccgtctg gaggctcgtt ggttcctgga taaatatgaa  1500
ccgaaggagc cacatcatca acttctgctt gaattggcta agttagactt taacatggtt  1560
cagacactgc accagaagga actgcaggac ctgtcacgct ggtggactga gatgggttta  1620
gcttccaagc ttgacttcgt tcgtgacaga ctcatggagg tttatttttg ggccttggga  1680
atggcgcctg atccgcaatt tggtgagtgt cggaaagcgg ttacgaaaat gttcggggctg  1740
gtgaccatta tcgacgacgt gtatgatgtt tatgggacac tggatgaact tcaactcttt  1800
acggatgcag tcgaacgctg ggatgtgaat gcgataaaca ccctccctga ttacatgaaa  1860
ttgtgctttt tagcgctcta taatactgtt aacgatacat cctactcaat cctcaaagaa  1920
aaaggacaca ataaccttag ttatcttact aaatcttggc gcgagctgtg caaggccttc  1980
ctgcaggaag ctaaatggag taataacaag ataattcctg catttagcaa gtacttggaa  2040
aatgcaagtg taagttcttc cggtgtagct ttgctcgccc caagctactt ctcagtatgt  2100
caacagcagg aggatattag tgaccatgcg cttcgcagtt tgacggactt ccacggactc  2160
gtccgctctt catgcgtaat tttccgtttg tgcaacgatc tggccaccag cgcggccgag  2220
ttggagcgtg gagaaacgac taatagcatc ataagctata tgcatgaaaa tgacggaaca  2280
tccgaagagc aagcacgtga agagctccgg aagcttatag acgcagaatg gaagaagatg  2340
aaccgggagc gcgtatcaga tagtaccctc ttaccaaagg cttttatgga aattgcggtg  2400
aatatggcgc gcgtatccca ttgtacttac caatatgggg acggcttggg acgtcctgat  2460
tatgcgacag agaatcggat taaattattg ttaatcgacc cattcccaat caatcaactg  2520
atgtacgta                                                         2529

SEQ ID NO: 9           moltype = DNA  length = 2518
FEATURE                Location/Qualifiers
source                 1..2518
                       mol_type = other DNA
                       organism = synthetic construct
SEQUENCE: 9
atgaccgccg ataataactc tatgcctcac ggggctgtat ccagctacgc gaaattagta  60
caaaatcaga ccccggaaga catcctggag gaattcccag aaatcatccc tttacagcaa  120
cgtcctaaca cacgtagtag tgagacatct aacgatgaaa gcggggaaac ctgcttttct  180
gggcatgacg aggagcagat taagcttatg aacgagaact gcattgtttt ggattgggac  240
gataatgcta tcggagcggg tactaaaaag gtttgccatt taatggagaa tattgaaaaa  300
ggactgctgc atcgcgcgtt ctccgtattc atcttcaatg agcagggtga acttcttttg  360
caacaacgcg ccaccgaaaa gatcacgttc ccagatcttt ggaccaacac gtgttgctca  420
catcctttgt gtatcgacga tgaactggga ttaaagggta agttggacga caagattaag  480
ggagccatca cggctgccgt gcgtaagctt gaccatgagt tgggaattcc cgaagatgaa  540
accaaaacgc gtggcaagtt ccatttcctg aatcgtatcc attacatggc accttccaat  600
gaaccatggg gtgagcatga aatcgactat attttatttt acaagatcaa tgcgaaagag  660
aaccttaccg tcaacccgaa tgtgaatgag gtccgcgatt tcaaatgggt tagcccaaac  720
gacctgaaaa cgatgtttgc cgatcccagc tacaagttta caccgtggtt taagattatc  780
tgcgagaatt acttgttcaa ttggtgggag cagcttgacg acttatcgga agtagagaat  840
gaccgtcaga tccatcgcat gttaggaagc ggaggaggag gaagcatgga agctcgtcgt  900
tctgcgaact acgaacctaa cagctgggac tatgattacc tgctgtcctc cgacacggac  960
gagtccatcg aagtatacaa agacaaagcg aaaaagctgg aagccgaagt tcgtcgcgag  1020
attaataacg aaaaagcaga atttctgacc ctgctggaac tgattgacaa cgtccagcgc  1080
ctgggcctgg gttaccgttt cgagtctgat atccgtggtg cgctggatcg cttcgtttcc  1140
tccggcggct tcgatgcggt aaccaagact tccctgcacg gtacggcact gtctttccgt  1200
ctgctgcgtc aacacggttt tgaggtttct caggaagcgt tcagcggctt caaagaccaa  1260
aacggcaact tcctggagaa cctgaaggaa gatatcaaag ctatcctgag cctgtacgag  1320
gccagcttcc tggctctgga aggcgaaaac atcctggacg aggcgaaggt tttcgcaatc  1380
tctcatctga aagaactgtc tgaagaaaag atcggtaaag agctggcaga acaggtgaac  1440
catgcactgg aactgccact gcatcgccgt actcagcgtc tggaagcagt atggtctatc  1500
gaggcctacc gtaaaaagga ggacgcgaat caggttctgc tggagctggc aattctggat  1560
tacaacatga tccagtctgt ataccagcgt gatctgcgtg aaacgtcccg ttggtggcgt  1620
cgtgtgggtc tggcgaccaa actgcacttt gctcgtgacc gcctgattga gagcttctac  1680
tgggccgtgg gtgtagcatt cgaaccgcaa tactccgact gccgtaactc cgtcgcaaaa  1740
atgttttgtt tcgtaaccat tatcgacgat atctacgatg tatacggcac cctggacgaa  1800
```

-continued

```
ctggagctgt ttactgatgc agttgagcgt tgggacgtaa acgccatcaa cgacctgccg  1860
gattacatga aactgtgctt tctggctctg tataacacta ttaacgaaat cgcctacgac  1920
aacctgaaag ataaaggtga gaacatcctg ccgtatctga ccaaagcctg ggctgacctg  1980
tgcaacgctt tcctgcaaga agccaagtgg ctgtacaaca aatctactcc gacctttgac  2040
gactacttcg gcaacgcatg gaaatcctct tctggcccgc tgcaactggt gttcgcttac  2100
ttcgctgtcg tgcagaacat taaaaaggaa gagatcgaaa acctgcaaaa ataccatgac  2160
accatctctc gtccttccca tatcttccgt ctgtgcaatg acctggctag cgcgtctgcg  2220
gaaattgcgc gtggtgaaac cgcaaatagc gtttcttgtt acatgcgcac taaaggtatc  2280
tccgaagaac tggctaccga aagcgtgatg aatctgatcg atgaaacctg gaaaaagatg  2340
aacaaggaaa aactgagtgg tagcctgttc gcgaaaccgt tcgtggaaac cgcgatcaac  2400
ctggcacgtc aatctcactg cacttatcat aacggcgacg cgcatacctc tccggatgag  2460
ctgacccgca aacgcgttct gtctgtaatc actgaaccga ttctgccgtt tgaacgct    2518

SEQ ID NO: 10          moltype = DNA  length = 2538
FEATURE                Location/Qualifiers
source                 1..2538
                       mol_type = other DNA
                       organism = synthetic construct
SEQUENCE: 10
atgaccgccg ataataactc tatgcctcac ggggctgtat ccagctacgc gaaattagta  60
caaaatcaga ccccggaaga catcctggag gaattcccag aaatcatccc tttacagcaa  120
cgtcctaaca cacgtagtag tgagacatct aacgatgaaa gcggggaaac ctgcttttct  180
gggcatgacg aggagcagat taagcttatg aacgagaact gcattgtttt ggattgggac  240
gataatgcta tcggagcggg tactaaaaag gtttgccatt taatggagaa tattgaaaaa  300
ggactgctgc atcgcgcgtt ctccgtattc atcttcaatg agcagggtga acttcttttg  360
caacaacgcg ccaccgaaaa gatcacgttc ccagatcttt ggaccaacac gtgttgctca  420
catcctttgt gtatcgacga tgaactggga ttaaagggta agttggacga caagattaag  480
ggagccatca cggctgccgt gcgtaagctt gaccatgagt tgggaattcc cgaagatgaa  540
accaaaacgc gtggcaagtt ccatttcctg aatcgtatcc attacatggc accttccaat  600
gaaccatggg gtgagcatga aatcgactat attttatttt acaagatcaa tgcgaaagag  660
aaccttaccg tcaacccgaa tgtgaatgag gtccgcgatt tcaaatgggt tagcccaaac  720
gacctgaaaa cgatgtttgc cgatcccagc tacaagttta caccgtggtt taagattatc  780
tgcgagaatt acttgttcaa ttggtgggag cagcttgacg acttatcgga agtagagaat  840
gaccgtcaga tccatcgcat gttaggaagc ggaggaggag gaagcatgaa ctcacgtcgt  900
tcagctaatt atcaaccaaa cctctggaat tttgagtttc tgcagagttt ggaaaacgac  960
cttaaggttg agaaacttga ggagaaggcg acgaaactgg aagaggaagt tcgctgcatg  1020
atcaatcgtg tggatacaca acctctgagt ttgcttgaac tgattgatga cgtgcagaga  1080
ctcggactga cgtacaagtt cgaaaaagat atcatcaaag ctctggagaa tatcgtcctt  1140
ctggatgaga acaagaaaaa taagtcagac ttgcacgcga cagcgctgag ctttcgttta  1200
ttaagacaac acggctttag agtgtcacaa gacgtttttg agcggttcaa ggataaggag  1260
gggggtttca gtggggaact caagggtgac gtgcaaggac tcctcagtct gtacgaggcg  1320
agttatctcg ggttcgaggg tgagaattta ttagaagagg cacggacttt ttctataaca  1380
cacttaaaaa ataacttgaa agaaggtata aacactaaag tcgccgaaca ggtttcacat  1440
gctctggagc tcccttatca ccagagactc caccgtctgg aggctcgttg gttcctggat  1500
aaatatgaac cgaaggagcc acatcatcaa cttctgcttg aattggctaa gttagacttt  1560
aacatggttc agacactgca ccagaaggaa ctgcaggacc tgtcacgctg gtggactgag  1620
atgggtttag cttccaagct tgacttcgtt cgtgacagac tcatggaggt ttatttttgg  1680
gccttgggaa tggcgcctga tccgcaattt ggtgagtgtc ggaaagcggt tacgaaaatg  1740
ttcgggctgg tgaccattat cgacgacgtg tatgatgttt atgggacact ggatgaactt  1800
caactcttta cggatgcagt cgaacgctgg gatgtgaatg cgataaacac cctccctgat  1860
tacatgaaat tgtgcttttt agcgctctat aatactgtta acgatacatc ctactcaatc  1920
ctcaaagaaa aaggacacaa taaccttagt tatcttacta aatcttggcg cgagctgtgc  1980
aaggccttcc tgcaggaagc taaatggagt aataacaaga taattcctgc atttagcaag  2040
tacttggaaa atgcaagtgt aagttcttcc ggtgtagctt tgctcgcccc aagctacttc  2100
tcagtatgtc aacagcagga ggatattagt gaccatgcgc ttcgcagttt gacggacttc  2160
cacggactcg tccgctcttc atgcgtaatt ttccgtttgt gcaacgatct ggccaccagc  2220
gcggccgagt tggagcgtgg agaaacgact aatagcatca taagctatat gcatgaaaat  2280
gacggaacat ccgaagagca agcacgtgaa gagctccgga agcttataga cgcagaatgg  2340
aagaagatga accgggagcg cgtatcagat agtaccctct taccaaaggc ttttatggaa  2400
attgcggtga atatggcgcg cgtatcccat tgtacttacc aatatgggga cggcttggga  2460
cgtcctgatt atgcgacaga gaatcggatt aaattattgt taatcgaccc attcccaatc  2520
aatcaactga tgtacgta                                                2538

SEQ ID NO: 11          moltype = DNA  length = 2536
FEATURE                Location/Qualifiers
source                 1..2536
                       mol_type = other DNA
                       organism = synthetic construct
SEQUENCE: 11
atgaccgccg ataataactc tatgcctcac ggggctgtat ccagctacgc gaaattagta  60
caaaatcaga ccccggaaga catcctggag gaattcccag aaatcatccc tttacagcaa  120
cgtcctaaca cacgtagtag tgagacatct aacgatgaaa gcggggaaac ctgcttttct  180
gggcatgacg aggagcagat taagcttatg aacgagaact gcattgtttt ggattgggac  240
gataatgcta tcggagcggg tactaaaaag gtttgccatt taatggagaa tattgaaaaa  300
ggactgctgc atcgcgcgtt ctccgtattc atcttcaatg agcagggtga acttcttttg  360
caacaacgcg ccaccgaaaa gatcacgttc ccagatcttt ggaccaacac gtgttgctca  420
catcctttgt gtatcgacga tgaactggga ttaaagggta agttggacga caagattaag  480
ggagccatca cggctgccgt gcgtaagctt gaccatgagt tgggaattcc cgaagatgaa  540
accaaaacgc gtggcaagtt ccatttcctg aatcgtatcc attacatggc accttccaat  600
```

-continued

```
gaaccatggg gtgagcatga aatcgactat attttatttt acaagatcaa tgcgaaagag  660
aaccttaccg tcaacccgaa tgtgaatgag gtccgcgatt tcaaatgggt tagcccaaac  720
gacctgaaaa cgatgtttgc cgatcccagc tacaagttta caccgtggtt taagattatc  780
tgcgagaatt acttgttcaa ttggtgggag cagcttgacg acttatcgga agtagagaat  840
gaccgtcaga tccatcgcat gttaggaagc ggagaagcag cagcaaaaga agcagcagca  900
aaaatggaag ctcgtcgttc tgcgaactac gaacctaaca gctgggacta tgattacctg  960
ctgtcctccg acacggacga gtccatcgaa gtatacaaag acaaagcgaa aaagctggaa  1020
gccgaagttc gtcgcgagat taataacgaa aaagcagaat ttctgaccct gctggaactg  1080
attgacaacg tccagcgcct gggcctgggt taccgtttcg agtctgatat ccgtggtgcg  1140
ctggatcgct tcgtttcctc cggcggcttc gatgcggtaa ccaagacttc cctgcacggt  1200
acggcactgt ctttccgtct gctgcgtcaa cacggttttg aggtttctca ggaagcgttc  1260
agcggcttca aagaccaaaa cggcaacttc ctggagaacc tgaaggaaga tatcaaagct  1320
atcctgagcc tgtacgaggc cagcttcctg gctctggaag gcgaaaacat cctggacgag  1380
gcgaaggttt tcgcaatctc tcatctgaaa gaactgtctg aagaaaagat cggtaaagag  1440
ctggcagaac aggtgaacca tgcactggaa ctgccactgc atcgccgtac tcagcgtctg  1500
gaagcagtat ggtctatcga ggcctaccgt aaaaaggagg acgcgaatca ggttctgctg  1560
gagctggcaa ttctggatta caacatgatc cagtctgtat accagcgtga tctgcgtgaa  1620
acgtcccgtt ggtggcgtcg tgtgggtctg gcgaccaaac tgcactttgc tcgtgaccgc  1680
ctgattgaga gcttctactg ggccgtgggt gtagcattcg aaccgcaata ctccgactgc  1740
cgtaactccg tcgcaaaaat gttttgtttc gtaaccatta tcgacgatat ctacgatgta  1800
tacggcaccc tggacgaact ggagctgttt actgatgcag ttgagcgttg ggacgtaaac  1860
gccatcaacg acctgccgga ttacatgaaa ctgtgctttc tggctctgta taacactatt  1920
aacgaaatcg cctacgacaa cctgaaagat aaaggtgaga acatcctgcc gtatctgacc  1980
aaagcctggg ctgacctgtg caacgctttc ctgcaagaag ccaagtggct gtacaacaaa  2040
tctactccga cctttgacga ctacttcggc aacgcatgga aatcctcttc tggcccgctg  2100
caactggtgt tcgcttactt cgctgtcgtg cagaacatta aaaaggaaga gatcgaaaac  2160
ctgcaaaaat accatgacac catctctcgt ccttcccata tcttccgtct gtgcaatgac  2220
ctggctagcg cgtctgcgga aattgcgcgt ggtgaaaccg caaatagcgt ttcttgttac  2280
atgcgcacta aaggtatctc cgaagaactg gctaccgaaa gcgtgatgaa tctgatcgat  2340
gaaacctgga aaaagatgaa caaggaaaaa ctgagtggta gcctgttcgc gaaaccgttc  2400
gtggaaaccg cgatcaacct ggcacgtcaa tctcactgca cttatcataa cggcgacgcg  2460
catacctctc cggatgagct gacccgcaaa cgcgttctgt ctgtaatcac tgaaccgatt  2520
ctgccgtttg aacgct                                                 2536
```

```
SEQ ID NO: 12          moltype = DNA  length = 2556
FEATURE                Location/Qualifiers
source                 1..2556
                       mol_type = other DNA
                       organism = synthetic construct
SEQUENCE: 12
atgaccgccg ataataactc tatgcctcac ggggctgtat ccagctacgc gaaattagta  60
caaaatcaga ccccggaaga catcctggag gaattcccag aaatcatccc tttacagcaa  120
cgtcctaaca cacgtagtag tgagacatct aacgatgaaa gcggggaaac ctgcttttct  180
gggcatgacg aggagcagat taagcttatg aacgagaact gcattgtttt ggattgggac  240
gataatgcta tcggagcggg tactaaaaag gtttgccatt taatggagaa tattgaaaaa  300
ggactgctgc atcgcgcgtt ctccgtattc atcttcaatg agcagggtga acttcttttg  360
caacaacgcg ccaccgaaaa gatcacgttc ccagatcttt ggaccaacac gtgttgctca  420
catcctttgt gtatcgacga tgaactggga ttaaagggta agttggacga caagattaag  480
ggagccatca cggctgccgt gcgtaagctt gaccatgagt tgggaattcc cgaagatgaa  540
accaaaacgc gtggcaagtt ccatttcctg aatcgtatcc attacatggc accttccaat  600
gaaccatggg gtgagcatga aatcgactat attttatttt acaagatcaa tgcgaaagag  660
aaccttaccg tcaacccgaa tgtgaatgag gtccgcgatt tcaaatgggt tagcccaaac  720
gacctgaaaa cgatgtttgc cgatcccagc tacaagttta caccgtggtt taagattatc  780
tgcgagaatt acttgttcaa ttggtgggag cagcttgacg acttatcgga agtagagaat  840
gaccgtcaga tccatcgcat gttaggaagc ggagaagcag cagcaaaaga agcagcagca  900
aaaatgaact cacgtcgttc agctaattat caaccaaacc tctggaattt tgagtttctg  960
cagagtttgg aaaacgacct taaggttgag aaacttgagg agaaggcgac gaaactggaa  1020
gaggaagttc gctgcatgat caatcgtgtg gatacacaac ctctgagttt gcttgaactg  1080
attgatgacg tgcagagact cggactgacg tacaagttcg aaaaagatat catcaaagct  1140
ctggagaata tcgtccttct ggatgagaac aagaaaaata agtcagactt gcacgcgaca  1200
gcgctgagct ttcgtttatt aagacaacac ggctttgaag tgtcacaaga cgtttttgag  1260
cggttcaagg ataaggaggg gggtttcagt ggggaactca agggtgacgt gcaaggactc  1320
ctcagtctgt acgaggcgag ttatctcggg ttcgagggtg agaatttatt agaagaggca  1380
cggacttttt ctataacaca cttaaaaaat aacttgaaag aaggtataaa cactaaagtc  1440
gccgaacagg tttcacatgc tctggagctc ccttatcacc agagactcca ccgtctggag  1500
gctcgttggt tcctggataa atatgaaccg aaggagccac atcatcaact tctgcttgaa  1560
ttggctaagt tagactttaa catggttcag acactgcacc agaaggaact gcaggacctg  1620
tcacgctggt ggactgagat gggtttagct tccaagcttg acttcgttcg tgacagactc  1680
atggaggttt atttttgggc cttgggaatg gcgcctgatc cgcaatttgg tgagtgtcgg  1740
aaagcggtta cgaaaatgtt cgggctggtg accattatcg acgacgtgta tgatgtttat  1800
gggacactgg atgaacttca actctttacg gatgcagtcg aacgctggga tgtgaatgcg  1860
ataaacaccc tccctgatta catgaaattg tgcttttttag cgctctataa tactgttaac  1920
gatacatcct actcaatcct caaagaaaaa ggacacaata accttagtta tcttactaaa  1980
tcttggcgcg agctgtgcaa ggccttcctg caggaagcta aatggagtaa taacaagata  2040
attcctgcat ttagcaagta cttggaaaat gcaagtgtaa gttcttccgg tgtagctttg  2100
ctcgccccaa gctacttctc agtatgtcaa cagcaggagg atattagtga ccatgcgctt  2160
cgcagtttga cggacttcca cggactcgtc cgctcttcat gcgtaatttt ccgtttgtgc  2220
aacgatctgg ccaccagcgc ggccgagttg gagcgtggag aaacgactaa tagcatcata  2280
agctatatgc atgaaaatga cggaacatcc gaagagcaag cacgtgaaga gctccggaag  2340
```

-continued

```
cttatagacg cagaatggaa gaagatgaac cgggagcgcg tatcagatag taccctctta  2400
ccaaaggctt ttatggaaat tgcggtgaat atggcgcgcg tatcccattg tacttaccaa  2460
tatggggacg gcttgggacg tcctgattat gcgacagaga atcggattaa attattgtta  2520
atcgacccat tcccaatcaa tcaactgatg tacgta                            2556

SEQ ID NO: 13          moltype = DNA  length = 2191
FEATURE                Location/Qualifiers
source                 1..2191
                       mol_type = other DNA
                       organism = synthetic construct
SEQUENCE: 13
atggaagctc gtcgttctgc gaactacgaa cctaacagct gggactatga ttacctgctg  60
tcctccgaca cggacgagtc catcgaagta tacaaagaca aagcgaaaaa gctggaagcc  120
gaagttcgtc gcgagattaa taacgaaaaa gcagaatttc tgaccctgct ggaactgatt  180
gacaacgtcc agcgcctggg cctgggttac cgtttcgagt ctgatatccg tggtgcgctg  240
gatcgcttcg tttcctccgg cggcttcgat gcggtaacca agacttccct gcacggtacg  300
gcactgtctt tccgtctgct gcgtcaacac ggttttgagg tttctcagga agcgttcagc  360
ggcttcaaag accaaaacgg caacttcctg gagaacctga aggaagatat caaagctatc  420
ctgagcctgt acgaggccag cttcctggct ctggaaggcg aaaacatcct ggacgaggcg  480
aaggttttcg caatctctca tctgaaagaa ctgtctgaag aaaagatcgg taaagagctg  540
gcagaacagg tgaaccatgc actggaactg ccactgcatc gccgtactca gcgtctggaa  600
gcagtatggt ctatcgaggc ctaccgtaaa aaggaggacg cgaatcaggt tctgctggag  660
ctggcaattc tggattacaa catgatccag tctgtatacc agcgtgatct gcgtgaaacg  720
tcccgttggt ggcgtcgtgt gggtctggcg accaaactgc actttgctcg tgaccgcctg  780
attgagagct tctactgggc cgtgggtgta gcattcgaac cgcaatactc cgactgccgt  840
aactccgtcg caaaaatgtt ttgtttcgta accattatcg acgatatcta cgatgtatac  900
ggcaccctgg acgaactgga gctgtttact gatgcagttg agcgttggga cgtaaacgcc  960
atcaacgacc tgccggatta catgaaactg tgctttctgg ctctgtataa cactattaac  1020
gaaatcgcct acgacaacct gaaagataaa ggtgagaaca tcctgccgta tctgaccaaa  1080
gcctgggctg acctgtgcaa cgctttcctg caagaagcca agtggctgta caacaaatct  1140
actccgacct ttgacgacta cttcggcaac gcatggaaat cctcttctgg cccgctgcaa  1200
ctggtgttcg cttacttcgc tgtcgtgcag aacattaaaa aggaagagat cgaaaacctg  1260
caaaaatacc atgacaccat ctctcgtcct tcccatatct tccgtctgtg caatgacctg  1320
gctagcgcgt ctgcggaaat tgcgcgtggt gaaaccgcaa atagcgtttc ttgttacatg  1380
cgcactaaag gtatctccga agaactggct accgaaagcg tgatgaatct gatcgatgaa  1440
acctggaaaa agatgaacaa ggaaaaactg agtggtagcc tgttcgcgaa accgttcgtg  1500
gaaaccgcga tcaacctggc acgtcaatct cactgcactt atcataacgg cgacgcgcat  1560
acctctccgg atgagctgac ccgcaaacgc gttctgtctg taatcactga accgattctg  1620
ccgtttgaac gctggaggag gaagcatgca aacggaacac gtcattttat tgaatgcaca  1680
gggagttccc acgggtacgc tggaaaagta tgccgcacac acggcagaca cccgcttaca  1740
tctcgcgttc tccagttggc tgtttaatgc caaaggacaa ttattagtta cccgccgcgc  1800
actgagcaaa aaagcatggc ctggcgtgtg gactaactcg gtttgtgggc acccacaact  1860
gggagaaagc aacgaagacg cagtgatccg ccgttgccgt tatgagcttg gcgtggaaat  1920
tacgcctcct gaatctatct atcctgactt tcgctaccgc gccaccgatc cgagtggcat  1980
tgtggaaaat gaagtgtgtc cggtatttgc cgcacgcacc actagtgcgt tacagatcaa  2040
tgatgatgaa gtgatggatt atcaatggtg tgatttagca gatgtattac acggtattga  2100
tgccacgccg tgggcgttca gtccgtggat ggtgatgcag gcgacaaatc gcgaagccag  2160
aaaacgatta tctgcattta cccagcttaa a                                 2191

SEQ ID NO: 14          moltype = DNA  length = 2509
FEATURE                Location/Qualifiers
source                 1..2509
                       mol_type = other DNA
                       organism = synthetic construct
SEQUENCE: 14
atggaagctc gtcgttctgc gaactacgaa cctaacagct gggactatga ttacctgctg  60
tcctccgaca cggacgagtc catcgaagta tacaaagaca aagcgaaaaa gctggaagcc  120
gaagttcgtc gcgagattaa taacgaaaaa gcagaatttc tgaccctgct ggaactgatt  180
gacaacgtcc agcgcctggg cctgggttac cgtttcgagt ctgatatccg tggtgcgctg  240
gatcgcttcg tttcctccgg cggcttcgat gcggtaacca agacttccct gcacggtacg  300
gcactgtctt tccgtctgct gcgtcaacac ggttttgagg tttctcagga agcgttcagc  360
ggcttcaaag accaaaacgg caacttcctg gagaacctga aggaagatat caaagctatc  420
ctgagcctgt acgaggccag cttcctggct ctggaaggcg aaaacatcct ggacgaggcg  480
aaggttttcg caatctctca tctgaaagaa ctgtctgaag aaaagatcgg taaagagctg  540
gcagaacagg tgaaccatgc actggaactg ccactgcatc gccgtactca gcgtctggaa  600
gcagtatggt ctatcgaggc ctaccgtaaa aaggaggacg cgaatcaggt tctgctggag  660
ctggcaattc tggattacaa catgatccag tctgtatacc agcgtgatct gcgtgaaacg  720
tcccgttggt ggcgtcgtgt gggtctggcg accaaactgc actttgctcg tgaccgcctg  780
attgagagct tctactgggc cgtgggtgta gcattcgaac cgcaatactc cgactgccgt  840
aactccgtcg caaaaatgtt ttgtttcgta accattatcg acgatatcta cgatgtatac  900
ggcaccctgg acgaactgga gctgtttact gatgcagttg agcgttggga cgtaaacgcc  960
atcaacgacc tgccggatta catgaaactg tgctttctgg ctctgtataa cactattaac  1020
gaaatcgcct acgacaacct gaaagataaa ggtgagaaca tcctgccgta tctgaccaaa  1080
gcctgggctg acctgtgcaa cgctttcctg caagaagcca agtggctgta caacaaatct  1140
actccgacct ttgacgacta cttcggcaac gcatggaaat cctcttctgg cccgctgcaa  1200
ctggtgttcg cttacttcgc tgtcgtgcag aacattaaaa aggaagagat cgaaaacctg  1260
caaaaatacc atgacaccat ctctcgtcct tcccatatct tccgtctgtg caatgacctg  1320
gctagcgcgt ctgcggaaat tgcgcgtggt gaaaccgcaa atagcgtttc ttgttacatg  1380
cgcactaaag gtatctccga agaactggct accgaaagcg tgatgaatct gatcgatgaa  1440
```

-continued

```
acctggaaaa agatgaacaa ggaaaaactg agtggtagcc tgttcgcgaa accgttcgtg  1500
gaaaccgcga tcaacctggc acgtcaatct cactgcactt atcataacgg cgacgcgcat  1560
acctctccgg atgagctgac ccgcaaacgc gttctgtctg taatcactga accgattctg  1620
ccgtttgaac gctggaggag gaagcatgac cgccgataat aactctatgc ctcacggggc  1680
tgtatccagc tacgcgaaat tagtacaaaa tcagaccccg gaagacatcc tggaggaatt  1740
cccagaaatc atcccttttac agcaacgtcc taacacacgt agtagtgaga catctaacga  1800
tgaaagcggg gaaacctgct tttctgggca tgacgaggag cagattaagc ttatgaacga  1860
gaactgcatt gttttggatt gggacgataa tgctatcgga gcgggtacta aaaaggtttg  1920
ccatttaatg gagaatattg aaaaaggact gctgcatcgc gcgttctccg tattcatctt  1980
caatgagcag ggtgaacttc ttttgcaaca acgcgccacc gaaaagatca cgttcccaga  2040
tctttggacc aacacgtgtt gctcacatcc tttgtgtatc gacgatgaac tgggattaaa  2100
gggtaagttg gacgacaaga ttaagggagc catcacggct gccgtgcgta agcttgacca  2160
tgagttggga attcccgaag atgaaaccaa aacgcgtggc aagttccatt tcctgaatcg  2220
tatccattac atggcacctt ccaatgaacc atggggtgag catgaaatcg actatatttt  2280
attttacaag atcaatgcga aagagaacct taccgtcaac ccgaatgtga atgaggtccg  2340
cgatttcaaa tgggttagcc caaacgacct gaaaacgatg tttgccgatc ccagctacaa  2400
gtttacaccg tggtttaaga ttatctgcga gaattacttg ttcaattggt gggagcagct  2460
tgacgactta tcggaagtag agaatgaccg tcagatccat cgcatgtta              2509

SEQ ID NO: 15          moltype = DNA  length = 2200
FEATURE                Location/Qualifiers
source                 1..2200
                       mol_type = other DNA
                       organism = synthetic construct
SEQUENCE: 15
atggaagctc gtcgttctgc gaactacgaa cctaacagct gggactatga ttacctgctg  60
tcctccgaca cggacgagtc catcgaagta tacaaagaca aagcgaaaaa gctggaagcc  120
gaagttcgtc gcgagattaa taacgaaaaa gcagaatttc tgaccctgct ggaactgatt  180
gacaacgtcc agcgcctggg cctgggttac cgtttcgagt ctgatatccg tggtgcgctg  240
gatcgcttcg tttcctccgg cggcttcgat gcggtaacca agacttccct gcacggtacg  300
gcactgtctt tccgtctgct gcgtcaacac ggttttgagg tttctcagga agcgttcagc  360
ggcttcaaag accaaaacgg caacttcctg gagaacctga aggaagatat caaagctatc  420
ctgagcctgt acgaggccag cttcctggct ctggaaggcg aaaacatcct ggacgaggcg  480
aaggttttcg caatctctca tctgaaagaa ctgtctgaag aaaagatcgg taaagagctg  540
gcagaacagg tgaaccatgc actggaactg ccactgcatc gccgtactca gcgtctggaa  600
gcagtatggt ctatcgaggc ctaccgtaaa aaggaggacg cgaatcaggt tctgctggag  660
ctggcaattc tggattacaa catgatccag tctgtatacc agcgtgatct gcgtgaaacg  720
tcccgttggt ggcgtcgtgt gggtctggcg accaaactgc actttgctcg tgaccgcctg  780
attgagagct tctactgggc cgtgggtgta gcattcgaac cgcaatactc cgactgccgt  840
aactccgtcg caaaaatgtt ttgtttcgta accattatcg acgatatcta cgatgtatac  900
ggcaccctgg acgaactgga gctgtttact gatgcagttg agcgttggga cgtaaacgcc  960
atcaacgacc tgccggatta catgaaactg tgctttctgg ctctgtataa cactattaac  1020
gaaatcgcct acgacaacct gaaagataaa ggtgagaaca tcctgccgta tctgaccaaa  1080
gcctgggctg acctgtgcaa cgctttcctg caagaagcca agtggctgta caacaaatct  1140
actccgacct ttgacgacta cttcggcaac gcatggaaat cctcttctgg cccgctgcaa  1200
ctggtgttcg cttacttcgc tgtcgtgcag aacattaaaa aggaagagat cgaaaacctg  1260
caaaaatacc atgacaccat ctctcgtcct tcccatatct tccgtctgtg caatgacctg  1320
gctagcgcgt ctgcggaaat tgcgcgtggt gaaaccgcaa atagcgtttc ttgttacatg  1380
cgcactaaag gtatctccga agaactggct accgaaagcg tgatgaatct gatcgatgaa  1440
acctggaaaa agatgaacaa ggaaaaactg agtggtagcc tgttcgcgaa accgttcgtg  1500
gaaaccgcga tcaacctggc acgtcaatct cactgcactt atcataacgg cgacgcgcat  1560
acctctccgg atgagctgac ccgcaaacgc gttctgtctg taatcactga accgattctg  1620
ccgtttgaac gctggaagcg gaggaggagg aagcatgcaa acggaacacg tcattttatt  1680
gaatgcacag ggagttccca cgggtacgct ggaaaagtat gccgcacaca cggcagacac  1740
ccgcttacat ctcgcgttct ccagttggct gtttaatgcc aaaggacaat tattagttac  1800
ccgccgcgca ctgagcaaaa aagcatggcc tggcgtgtgg actaactcgg tttgtgggca  1860
cccacaactg ggagaaagca acgaagacgc agtgatccgc cgttgccgtt atgagcttgg  1920
cgtggaaatt acgcctcctg aatctatcta tcctgacttt cgctaccgcg ccaccgatcc  1980
gagtggcatt gtggaaaatg aagtgtgtcc ggtatttgcc gcacgcacca ctagtgcgtt  2040
acagatcaat gatgatgaag tgatggatta tcaatggtgt gatttagcag atgtattaca  2100
cggtattgat gccacgccgt gggcgttcag tccgtggatg gtgatgcagg cgacaaatcg  2160
cgaagccaga aaacgattat ctgcatttac ccagcttaaa                        2200

SEQ ID NO: 16          moltype = DNA  length = 2518
FEATURE                Location/Qualifiers
source                 1..2518
                       mol_type = other DNA
                       organism = synthetic construct
SEQUENCE: 16
atggaagctc gtcgttctgc gaactacgaa cctaacagct gggactatga ttacctgctg  60
tcctccgaca cggacgagtc catcgaagta tacaaagaca aagcgaaaaa gctggaagcc  120
gaagttcgtc gcgagattaa taacgaaaaa gcagaatttc tgaccctgct ggaactgatt  180
gacaacgtcc agcgcctggg cctgggttac cgtttcgagt ctgatatccg tggtgcgctg  240
gatcgcttcg tttcctccgg cggcttcgat gcggtaacca agacttccct gcacggtacg  300
gcactgtctt tccgtctgct gcgtcaacac ggttttgagg tttctcagga agcgttcagc  360
ggcttcaaag accaaaacgg caacttcctg gagaacctga aggaagatat caaagctatc  420
ctgagcctgt acgaggccag cttcctggct ctggaaggcg aaaacatcct ggacgaggcg  480
aaggttttcg caatctctca tctgaaagaa ctgtctgaag aaaagatcgg taaagagctg  540
gcagaacagg tgaaccatgc actggaactg ccactgcatc gccgtactca gcgtctggaa  600
```

```
gcagtatggt ctatcgaggc ctaccgtaaa aaggaggacg cgaatcaggt tctgctggag  660
ctggcaattc tggattacaa catgatccag tctgtatacc agcgtgatct gcgtgaaacg  720
tcccgttggt ggcgtcgtgt gggtctggcg accaaactgc actttgctcg tgaccgcctg  780
attgagagct tctactgggc cgtgggtgta gcattcgaac cgcaatactc cgactgccgt  840
aactccgtcg caaaaatgtt ttgtttcgta accattatcg acgatatcta cgatgtatac  900
ggcaccctgg acgaactgga gctgtttact gatgcagttg agcgttggga cgtaaacgcc  960
atcaacgacc tgccggatta catgaaactg tgctttctgg ctctgtataa cactattaac  1020
gaaatcgcct acgacaacct gaaagataaa ggtgagaaca tcctgccgta tctgaccaaa  1080
gcctgggctg acctgtgcaa cgctttcctg caagaagcca agtggctgta caacaaatct  1140
actccgacct ttgacgacta cttcggcaac gcatggaaat cctcttctgg cccgctgcaa  1200
ctggtgttcg cttacttcgc tgtcgtgcag aacattaaaa aggaagagat cgaaaacctg  1260
caaaaatacc atgacaccat ctctcgtcct tcccatatct tccgtctgtg caatgacctg  1320
gctagcgcgt ctgcggaaat tgcgcgtggt gaaaccgcaa atagcgtttc ttgttacatg  1380
cgcactaaag gtatctccga agaactggct accgaaagcg tgatgaatct gatcgatgaa  1440
acctggaaaa agatgaacaa ggaaaaactg agtggtagcc tgttcgcgaa accgttcgtg  1500
gaaaccgcga tcaacctggc acgtcaatct cactgcactt atcataacgg cgacgcgcat  1560
acctctccgg atgagctgac ccgcaaacgc gttctgtctg taatcactga accgattctg  1620
ccgtttgaac gctggaagcg gaggaggagg aagcatgacc gccgataata actctatgcc  1680
tcacggggct gtatccagct acgcgaaatt agtacaaaat cagaccccgg aagacatcct  1740
ggaggaattc ccagaaatca tccctttaca gcaacgtcct aacacacgta gtagtgagac  1800
atctaacgat gaaagcgggg aaacctgctt ttctgggcat gacgaggagc agattaagct  1860
tatgaacgag aactgcattg ttttggattg ggacgataat gctatcggag cgggtactaa  1920
aaaggtttgc catttaatgg agaatattga aaaaggactg ctgcatcgcg cgttctccgt  1980
attcatcttc aatgagcagg gtgaacttct tttgcaacaa cgcgccaccg aaaagatcac  2040
gttcccagat ctttggacca acacgtgttg ctcacatcct ttgtgtatcg acgatgaact  2100
gggattaaag ggtaagttgg acgacaagat taagggagcc atcacggctg ccgtgcgtaa  2160
gcttgaccat gagttgggaa ttcccgaaga tgaaaccaaa acgcgtggca agttccattt  2220
cctgaatcgt atccattaca tggcaccttc caatgaacca tggggtgagc atgaaatcga  2280
ctatatttta ttttacaaga tcaatgcgaa agagaacctt accgtcaacc cgaatgtgaa  2340
tgaggtccgc gatttcaaat gggttagccc aaacgacctg aaaacgatgt ttgccgatcc  2400
cagctacaag tttacaccgt ggtttaagat tatctgcgag aattacttgt tcaattggtg  2460
ggagcagctt gacgacttat cggaagtaga gaatgaccgt cagatccatc gcatgtta    2518

SEQ ID NO: 17          moltype = DNA  length = 2218
FEATURE                Location/Qualifiers
source                 1..2218
                       mol_type = other DNA
                       organism = synthetic construct
SEQUENCE: 17
atggaagctc gtcgttctgc gaactacgaa cctaacagct gggactatga ttacctgctg  60
tcctccgaca cggacgagtc catcgaagta tacaaagaca aagcgaaaaa gctggaagcc  120
gaagttcgtc gcgagattaa taacgaaaaa gcagaatttc tgaccctgct ggaactgatt  180
gacaacgtcc agcgcctggg cctgggttac cgtttcgagt ctgatatccg tggtgcgctg  240
gatcgcttcg tttcctccgg cggcttcgat gcggtaacca agacttccct gcacggtacg  300
gcactgtctt tccgtctgct gcgtcaacac ggttttgagg tttctcagga agcgttcagc  360
ggcttcaaag accaaaacgg caacttcctg gagaacctga aggaagatat caaagctatc  420
ctgagcctgt acgaggccag cttcctggct ctggaaggcg aaaacatcct ggacgaggcg  480
aaggttttcg caatctctca tctgaaagaa ctgtctgaag aaaagatcgg taaagagctg  540
gcagaacagg tgaaccatgc actggaactg ccactgcatc gccgtactca gcgtctggaa  600
gcagtatggt ctatcgaggc ctaccgtaaa aaggaggacg cgaatcaggt tctgctggag  660
ctggcaattc tggattacaa catgatccag tctgtatacc agcgtgatct gcgtgaaacg  720
tcccgttggt ggcgtcgtgt gggtctggcg accaaactgc actttgctcg tgaccgcctg  780
attgagagct tctactgggc cgtgggtgta gcattcgaac cgcaatactc cgactgccgt  840
aactccgtcg caaaaatgtt ttgtttcgta accattatcg acgatatcta cgatgtatac  900
ggcaccctgg acgaactgga gctgtttact gatgcagttg agcgttggga cgtaaacgcc  960
atcaacgacc tgccggatta catgaaactg tgctttctgg ctctgtataa cactattaac  1020
gaaatcgcct acgacaacct gaaagataaa ggtgagaaca tcctgccgta tctgaccaaa  1080
gcctgggctg acctgtgcaa cgctttcctg caagaagcca agtggctgta caacaaatct  1140
actccgacct ttgacgacta cttcggcaac gcatggaaat cctcttctgg cccgctgcaa  1200
ctggtgttcg cttacttcgc tgtcgtgcag aacattaaaa aggaagagat cgaaaacctg  1260
caaaaatacc atgacaccat ctctcgtcct tcccatatct tccgtctgtg caatgacctg  1320
gctagcgcgt ctgcggaaat tgcgcgtggt gaaaccgcaa atagcgtttc ttgttacatg  1380
cgcactaaag gtatctccga agaactggct accgaaagcg tgatgaatct gatcgatgaa  1440
acctggaaaa agatgaacaa ggaaaaactg agtggtagcc tgttcgcgaa accgttcgtg  1500
gaaaccgcga tcaacctggc acgtcaatct cactgcactt atcataacgg cgacgcgcat  1560
acctctccgg atgagctgac ccgcaaacgc gttctgtctg taatcactga accgattctg  1620
ccgtttgaac gctggaagcg gagaagcagc agcaaaagaa gcagcagcaa aaatgcaaac  1680
ggaacacgtc attttattga atgcacaggg agttcccacg ggtacgctgg aaaagtatgc  1740
cgcacacacg gcagacaccc gcttacatct cgcgttctcc agttggctgt ttaatgccaa  1800
aggacaatta ttagttaccc gccgcgcact gagcaaaaaa gcatggcctg gcgtgtggac  1860
taactcggtt tgtgggcacc cacaactggg agaaagcaac gaagacgcag tgatccgccg  1920
ttgccgttat gagcttggcg tggaaattac gcctcctgaa tctatctatc ctgactttcg  1980
ctaccgcgcc accgatccga gtggcattgt ggaaaatgaa gtgtgtccgg tatttgccgc  2040
acgcaccact agtgcgttac agatcaatga tgatgaagtg atggattatc aatggtgtga  2100
tttagcagat gtattacacg gtattgatgc cacgccgtgg gcgttcagtc cgtggatggt  2160
gatgcaggcg acaaatcgcg aagccagaaa acgattatct gcatttaccc agcttaaa    2218

SEQ ID NO: 18          moltype = DNA  length = 2536
FEATURE                Location/Qualifiers
```

```
source                  1..2536
                        mol_type = other DNA
                        organism = synthetic construct
SEQUENCE: 18
atggaagctc gtcgttctgc gaactacgaa cctaacagct gggactatga ttacctgctg  60
tcctccgaca cggacgagtc catcgaagta tacaaagaca aagcgaaaaa gctggaagcc  120
gaagttcgtc gcgagattaa taacgaaaaa gcagaatttc tgaccctgct ggaactgatt  180
gacaacgtcc agcgcctggg cctgggttac cgtttcgagt ctgatatccg tggtgcgctg  240
gatcgcttcg tttcctccgg cggcttcgat gcggtaacca agacttccct gcacggtacg  300
gcactgtctt tccgtctgct gcgtcaacac ggttttgagg tttctcagga agcgttcagc  360
ggcttcaaag accaaaacgg caacttcctg gagaacctga aggaagatat caaagctatc  420
ctgagcctgt acgaggccag cttcctggct ctggaaggcg aaaacatcct ggacgaggcg  480
aaggttttcg caatctctca tctgaaagaa ctgtctgaag aaaagatcgg taaagagctg  540
gcagaacagg tgaaccatgc actggaactg ccactgcatc gccgtactca gcgtctggaa  600
gcagtatggt ctatcgaggc ctaccgtaaa aaggaggacg cgaatcaggt tctgctggag  660
ctggcaattc tggattacaa catgatccag tctgtatacc agcgtgatct gcgtgaaacg  720
tcccgttggt ggcgtcgtgt gggtctggcg accaaactgc actttgctcg tgaccgcctg  780
attgagagct tctactgggc cgtgggtgta gcattcgaac cgcaatactc cgactgccgt  840
aactccgtcg caaaaatgtt ttgtttcgta accattatcg acgatatcta cgatgtatac  900
ggcaccctgg acgaactgga gctgtttact gatgcagttg agcgttggga cgtaaacgcc  960
atcaacgacc tgccggatta catgaaactg tgctttctgg ctctgtataa cactattaac  1020
gaaatcgcct acgacaacct gaaagataaa ggtgagaaca tcctgccgta tctgaccaaa  1080
gcctgggctg acctgtgcaa cgctttcctg caagaagcca agtggctgta caacaaatct  1140
actccgacct ttgacgacta cttcggcaac gcatggaaat cctcttctgg cccgctgcaa  1200
ctggtgttcg cttacttcgc tgtcgtgcag aacattaaaa aggaagagat cgaaaacctg  1260
caaaaatacc atgacaccat ctctcgtcct tcccatatct tccgtctgtg caatgacctg  1320
gctagcgcgt ctgcggaaat tgcgcgtggt gaaaccgcaa atagcgtttc ttgttacatg  1380
cgcactaaag gtatctccga agaactggct accgaaagcg tgatgaatct gatcgatgaa  1440
acctggaaaa agatgaacaa ggaaaaactg agtggtagcc tgttcgcgaa accgttcgtg  1500
gaaaccgcga tcaacctggc acgtcaatct cactgcactt atcataacgg cgacgcgcat  1560
acctctccgg atgagctgac ccgcaaacgc gttctgtctg taatcactga accgattctg  1620
ccgtttgaac gctggaagcg gagaagcagc agcaaaagaa gcagcagcaa aaatgaccgc  1680
cgataataac tctatgcctc acggggctgt atccagctac gcgaaattag tacaaaatca  1740
gaccccggaa gacatcctgg aggaattccc agaaatcatc cctttacagc aacgtcctaa  1800
cacacgtagt agtgagacat ctaacgatga aagcggggaa acctgctttt ctgggcatga  1860
cgaggagcag attaagctta tgaacgagaa ctgcattgtt ttggattggg acgataatgc  1920
tatcggagcg ggtactaaaa aggtttgcca tttaatggag aatattgaaa aaggactgct  1980
gcatcgcgcg ttctccgtat tcatcttcaa tgagcagggt gaacttcttt tgcaacaacg  2040
cgccaccgaa aagatcacgt tcccagatct ttggaccaac acgtgttgct cacatccttt  2100
gtgtatcgac gatgaactgg gattaaaggg taagttggac gacaagatta agggagccat  2160
cacggctgcc gtgcgtaagc ttgaccatga gttgggaatt cccgaagatg aaaccaaaac  2220
gcgtggcaag ttccatttcc tgaatcgtat ccattacatg gcaccttcca atgaaccatg  2280
gggtgagcat gaaatcgact atattttatt ttacaagatc aatgcgaaag agaaccttac  2340
cgtcaacccg aatgtgaatg aggtccgcga tttcaaatgg gttagcccaa acgacctgaa  2400
aacgatgttt gccgatccca gctacaagtt tacaccgtgg tttaagatta tctgcgagaa  2460
ttacttgttc aattggtggg agcagcttga cgacttatcg gaagtagaga atgaccgtca  2520
gatccatcgc atgtta                                                  2536

SEQ ID NO: 19           moltype = DNA  length = 2211
FEATURE                 Location/Qualifiers
source                  1..2211
                        mol_type = other DNA
                        organism = synthetic construct
SEQUENCE: 19
atgaactcac gtcgttcagc taattatcaa ccaaacctct ggaattttga gtttctgcag  60
agtttggaaa acgaccttaa ggttgagaaa cttgaggaga aggcgacgaa actggaagag  120
gaagttcgct gcatgatcaa tcgtgtggat acacaacctc tgagtttgct tgaactgatt  180
gatgacgtgc agagactcgg actgacgtac aagttcgaaa aagatatcat caaagctctg  240
gagaatatcg tccttctgga tgagaacaag aaaaataagt cagacttgca cgcgacagcg  300
ctgagctttc gtttattaag acaacacggc tttgaagtgt cacaagacgt tttgagcgg  360
ttcaaggata aggagggggg tttcagtggg gaactcaagg gtgacgtgca aggactcctc  420
agtctgtacg aggcgagtta tctcgggttc gagggtgaga atttattaga agaggcacgg  480
actttttcta taacacactt aaaaaataac ttgaaagaag gtataaacac taaagtcgcc  540
gaacaggttt cacatgctct ggagctccct tatcaccaga gactccaccg tctggaggct  600
cgttggttcc tggataaata tgaaccgaag gagccacatc atcaacttct gcttgaattg  660
gctaagttag actttaacat ggttcagaca ctgcaccaga aggaactgca ggacctgtca  720
cgctggtgga ctgagatggg tttagcttcc aagcttgact tcgttcgtga cagactcatg  780
gaggtttatt tttgggcctt gggaatggcg cctgatccgc aatttggtga gtgtcggaaa  840
gcggttacga aaatgttcgg gctggtgacc attatcgacg acgtgtatga tgtttatggg  900
acactggatg aacttcaact ctttacggat gcagtcgaac gctgggatgt gaatgcgata  960
aacaccctcc ctgattacat gaaattgtgc tttttagcgc tctataatac tgttaacgat  1020
acatcctact caatcctcaa agaaaaagga cacaataacc ttagttatct tactaaatct  1080
tggcgcgagc tgtgcaaggc cttcctgcag gaagctaaat ggagtaataa caagataatt  1140
cctgcattta gcaagtactt ggaaaatgca agtgtaagtt cttccggtgt agctttgctc  1200
gccccaagct acttctcagt atgtcaacag caggaggata ttagtgacca tgcgcttcgc  1260
agtttgacgg acttccacgg actcgtccgc tcttcatgcg taattttccg tttgtgcaac  1320
gatctggcca ccagcgcggc cgagttggag cgtggagaaa cgactaatag catcataagc  1380
tatatgcatg aaaatgacgg aacatccgaa gagcaagcac gtgaagagct ccggaagctt  1440
atagacgcag aatggaagaa gatgaaccgg gagcgcgtat cagatagtac cctcttacca  1500
```

-continued

```
aaggctttta tggaaattgc ggtgaatatg gcgcgcgtat cccattgtac ttaccaatat  1560
ggggacggct tgggacgtcc tgattatgcg acagagaatc ggattaaatt attgttaatc  1620
gacccattcc caatcaatca actgatgtac gtaggaggag gaagcatgca aacggaacac  1680
gtcattttat tgaatgcaca gggagttccc acgggtacgc tggaaaagta tgccgcacac  1740
acggcagaca cccgcttaca tctcgcgttc tccagttggc tgtttaatgc caaaggacaa  1800
ttattagtta cccgccgcgc actgagcaaa aaagcatggc ctggcgtgtg gactaactcg  1860
gtttgtgggc acccacaact gggagaaagc aacgaagacg cagtgatccg ccgttgccgt  1920
tatgagcttg gcgtggaaat tacgcctcct gaatctatct atcctgactt tcgctaccgc  1980
gccaccgatc cgagtggcat tgtggaaaat gaagtgtgtc cggtatttgc cgcacgcacc  2040
actagtgcgt tacagatcaa tgatgatgaa gtgatggatt atcaatggtg tgatttagca  2100
gatgtattac acggtattga tgccacgccg tgggcgttca gtccgtggat ggtgatgcag  2160
gcgacaaatc gcgaagccag aaaacgatta tctgcattta cccagcttaa a           2211

SEQ ID NO: 20          moltype = DNA  length = 2529
FEATURE                Location/Qualifiers
source                 1..2529
                       mol_type = other DNA
                       organism = synthetic construct
SEQUENCE: 20
atgaactcac gtcgttcagc taattatcaa ccaaacctct ggaattttga gtttctgcag  60
agtttggaaa acgaccttaa ggttgagaaa cttgaggaga aggcgacgaa actggaagag  120
gaagttcgct gcatgatcaa tcgtgtggat acacaacctc tgagtttgct tgaactgatt  180
gatgacgtgc agagactcgg actgacgtac aagttcgaaa aagatatcat caaagctctg  240
gagaatatcg tccttctgga tgagaacaag aaaaataagt cagacttgca cgcgacagcg  300
ctgagctttc gtttattaag acaacacggc tttgaagtgt cacaagacgt tttgagcgg  360
ttcaaggata aggagggggg tttcagtggg gaactcaagg gtgacgtgca aggactcctc  420
agtctgtacg aggcgagtta tctcgggttc gagggtgaga atttattaga agaggcacgg  480
actttttcta taacacactt aaaaaataac ttgaaagaag gtataaacac taaagtcgcc  540
gaacaggttt cacatgctct ggagctccct tatcaccaga gactccaccg tctggaggct  600
cgttggttcc tggataaata tgaaccgaag gagccacatc atcaacttct gcttgaattg  660
gctaagttag actttaacat ggttcagaca ctgcaccaga aggaactgca ggacctgtca  720
cgctggtgga ctgagatggg tttagcttcc aagcttgact tcgttcgtga cagactcatg  780
gaggtttatt tttgggcctt gggaatggcg cctgatccgc aatttggtga gtgtcggaaa  840
gcggttacga aaatgttcgg gctggtgacc attatcgacg acgtgtatga tgtttatggg  900
acactggatg aacttcaact ctttacggat gcagtcgaac gctgggatgt gaatgcgata  960
aacaccctcc ctgattacat gaaattgtgc tttttagcgc tctataatac tgttaacgat  1020
acatcctact caatcctcaa agaaaaagga cacaataacc ttagttatct tactaaatct  1080
tggcgcgagc tgtgcaaggc cttcctgcag gaagctaaat ggagtaataa caagataatt  1140
cctgcattta gcaagtactt ggaaaatgca agtgtaagtt cttccggtgt agctttgctc  1200
gccccaagct acttctcagt atgtcaacag caggaggata ttagtgacca tgcgcttcgc  1260
agtttgacgg acttccacgg actcgtccgc tcttcatgcg taattttccg tttgtgcaac  1320
gatctggcca ccagcgcggc cgagttggag cgtggagaaa cgactaatag catcataagc  1380
tatatgcatg aaaatgacgg aacatccgaa gagcaagcac gtgaagagct ccggaagctt  1440
atagacgcag aatggaagaa gatgaaccgg gagcgcgtat cagatagtac cctcttacca  1500
aaggctttta tggaaattgc ggtgaatatg gcgcgcgtat cccattgtac ttaccaatat  1560
ggggacggct tgggacgtcc tgattatgcg acagagaatc ggattaaatt attgttaatc  1620
gacccattcc caatcaatca actgatgtac gtaggaggag gaagcatgac cgccgataat  1680
aactctatgc ctcacggggc tgtatccagc tacgcgaaat tagtacaaaa tcagaccccg  1740
gaagacatcc tggaggaatt cccagaaatc atccctttac agcaacgtcc taacacacgt  1800
agtagtgaga catctaacga tgaaagcggg gaaacctgct tttctgggca tgacgaggag  1860
cagattaagc ttatgaacga gaactgcatt gttttggatt gggacgataa tgctatcgga  1920
gcgggtacta aaaaggtttg ccatttaatg gagaatattg aaaaaggact gctgcatcgc  1980
gcgttctccg tattcatctt caatgagcag ggtgaacttc ttttgcaaca acgcgccacc  2040
gaaaagatca cgttcccaga tctttggacc aacacgtgtt gctcacatcc tttgtgtatc  2100
gacgatgaac tgggattaaa gggtaagttg gacgacaaga ttaagggagc catcacggct  2160
gccgtgcgta agcttgacca tgagttggga attcccgaag atgaaaccaa aacgcgtggc  2220
aagttccatt tcctgaatcg tatccattac atggcacctt ccaatgaacc atggggtgag  2280
catgaaatcg actatatttt attttacaag atcaatgcga aagagaacct taccgtcaac  2340
ccgaatgtga atgaggtccg cgatttcaaa tgggttagcc caaacgacct gaaaacgatg  2400
tttgccgatc ccagctacaa gtttacaccg tggtttaaga ttatctgcga gaattacttg  2460
ttcaattggt gggagcagct tgacgactta tcggaagtag agaatgaccg tcagatccat  2520
cgcatgtta                                                        2529

SEQ ID NO: 21          moltype = DNA  length = 2220
FEATURE                Location/Qualifiers
source                 1..2220
                       mol_type = other DNA
                       organism = synthetic construct
SEQUENCE: 21
atgaactcac gtcgttcagc taattatcaa ccaaacctct ggaattttga gtttctgcag  60
agtttggaaa acgaccttaa ggttgagaaa cttgaggaga aggcgacgaa actggaagag  120
gaagttcgct gcatgatcaa tcgtgtggat acacaacctc tgagtttgct tgaactgatt  180
gatgacgtgc agagactcgg actgacgtac aagttcgaaa aagatatcat caaagctctg  240
gagaatatcg tccttctgga tgagaacaag aaaaataagt cagacttgca cgcgacagcg  300
ctgagctttc gtttattaag acaacacggc tttgaagtgt cacaagacgt tttgagcgg  360
ttcaaggata aggagggggg tttcagtggg gaactcaagg gtgacgtgca aggactcctc  420
agtctgtacg aggcgagtta tctcgggttc gagggtgaga atttattaga agaggcacgg  480
actttttcta taacacactt aaaaaataac ttgaaagaag gtataaacac taaagtcgcc  540
gaacaggttt cacatgctct ggagctccct tatcaccaga gactccaccg tctggaggct  600
```

```
cgttggttcc tggataaata tgaaccgaag gagccacatc atcaacttct gcttgaattg  660
gctaagttag actttaacat ggttcagaca ctgcaccaga aggaactgca ggacctgtca  720
cgctggtgga ctgagatggg tttagcttcc aagcttgact tcgttcgtga cagactcatg  780
gaggtttatt tttgggcctt gggaatggcg cctgatccgc aatttggtga gtgtcggaaa  840
gcggttacga aaatgttcgg gctggtgacc attatcgacg acgtgtatga tgtttatggg  900
acactggatg aacttcaact ctttacggat gcagtcgaac gctgggatgt gaatgcgata  960
aacaccctcc ctgattacat gaaattgtgc tttttagcgc tctataatac tgttaacgat  1020
acatcctact caatcctcaa agaaaaagga cacaataacc ttagttatct tactaaatct  1080
tggcgcgagc tgtgcaaggc cttcctgcag gaagctaaat ggagtaataa caagataatt  1140
cctgcattta gcaagtactt ggaaaatgca agtgtaagtt cttccggtgt agctttgctc  1200
gccccaagct acttctcagt atgtcaacag caggaggata ttagtgacca tgcgcttcgc  1260
agtttgacgg acttccacgg actcgtccgc tcttcatgcg taattttccg tttgtgcaac  1320
gatctggcca ccagcgcggc cgagttggag cgtggagaaa cgactaatag catcataagc  1380
tatatgcatg aaaatgacgg aacatccgaa gagcaagcac gtgaagagct ccggaagctt  1440
atagacgcag aatggaagaa gatgaaccgg gagcgcgtat cagatagtac cctcttacca  1500
aaggctttta tggaaattgc ggtgaatatg gcgcgcgtat cccattgtac ttaccaatat  1560
ggggacggct tgggacgtcc tgattatgcg acagagaatc ggattaaatt attgttaatc  1620
gacccattcc caatcaatca actgatgtac gtaggaagcg gaggaggagg aagcatgcaa  1680
acggaacacg tcattttatt gaatgcacag ggagttccca cgggtacgct ggaaaagtat  1740
gccgcacaca cggcagacac ccgcttacat ctcgcgttct ccagttggct gtttaatgcc  1800
aaaggacaat tattagttac ccgccgcgca ctgagcaaaa aagcatggcc tggcgtgtgg  1860
actaactcgg tttgtgggca cccacaactg ggagaaagca acgaagacgc agtgatccgc  1920
cgttgccgtt atgagcttgg cgtggaaatt acgcctcctg aatctatcta tcctgacttt  1980
cgctaccgcg ccaccgatcc gagtggcatt gtggaaaatg aagtgtgtcc ggtatttgcc  2040
gcacgcacca ctagtgcgtt acagatcaat gatgatgaag tgatggatta tcaatggtgt  2100
gatttagcag atgtattaca cggtattgat gccacgccgt gggcgttcag tccgtggatg  2160
gtgatgcagg cgacaaatcg cgaagccaga aaacgattat ctgcatttac ccagcttaaa  2220

SEQ ID NO: 22          moltype = DNA  length = 2538
FEATURE                Location/Qualifiers
source                 1..2538
                       mol_type = other DNA
                       organism = synthetic construct
SEQUENCE: 22
atgaactcac gtcgttcagc taattatcaa ccaaacctct ggaattttga gtttctgcag  60
agtttggaaa acgaccttaa ggttgagaga cttgaggaga aggcgacgaa actggaagag  120
gaagttcgct gcatgatcaa tcgtgtggat acacaacctc tgagtttgct tgaactgatt  180
gatgacgtgc agagactcgg actgacgtac aagttcgaaa aagatatcat caaagctctg  240
gagaatatcg tccttctgga tgagaacaag aaaaataagt cagacttgca cgcgacagcg  300
ctgagctttc gtttattaag acaacacggc tttgaagtgt cacaagacgt ttttgagcgg  360
ttcaaggata aggagggggg tttcagtggg gaactcaagg gtgacgtgca aggactcctc  420
agtctgtacg aggcgagtta tctcgggttc gagggtgaga atttattaga agaggcacgg  480
actttttcta taacacactt aaaaaataac ttgaaagaag gtataaacac taaagtcgcc  540
gaacaggttt cacatgctct ggagctccct tatcaccaga gactccaccg tctggaggct  600
cgttggttcc tggataaata tgaaccgaag gagccacatc atcaacttct gcttgaattg  660
gctaagttag actttaacat ggttcagaca ctgcaccaga aggaactgca ggacctgtca  720
cgctggtgga ctgagatggg tttagcttcc aagcttgact tcgttcgtga cagactcatg  780
gaggtttatt tttgggcctt gggaatggcg cctgatccgc aatttggtga gtgtcggaaa  840
gcggttacga aaatgttcgg gctggtgacc attatcgacg acgtgtatga tgtttatggg  900
acactggatg aacttcaact ctttacggat gcagtcgaac gctgggatgt gaatgcgata  960
aacaccctcc ctgattacat gaaattgtgc tttttagcgc tctataatac tgttaacgat  1020
acatcctact caatcctcaa agaaaaagga cacaataacc ttagttatct tactaaatct  1080
tggcgcgagc tgtgcaaggc cttcctgcag gaagctaaat ggagtaataa caagataatt  1140
cctgcattta gcaagtactt ggaaaatgca agtgtaagtt cttccggtgt agctttgctc  1200
gccccaagct acttctcagt atgtcaacag caggaggata ttagtgacca tgcgcttcgc  1260
agtttgacgg acttccacgg actcgtccgc tcttcatgcg taattttccg tttgtgcaac  1320
gatctggcca ccagcgcggc cgagttggag cgtggagaaa cgactaatag catcataagc  1380
tatatgcatg aaaatgacgg aacatccgaa gagcaagcac gtgaagagct ccggaagctt  1440
atagacgcag aatggaagaa gatgaaccgg gagcgcgtat cagatagtac cctcttacca  1500
aaggctttta tggaaattgc ggtgaatatg gcgcgcgtat cccattgtac ttaccaatat  1560
ggggacggct tgggacgtcc tgattatgcg acagagaatc ggattaaatt attgttaatc  1620
gacccattcc caatcaatca actgatgtac gtaggaagcg gaggaggagg aagcatgacc  1680
gccgataata actctatgcc tcacggggct gtatccagct acgcgaaatt agtacaaaat  1740
cagaccccgg aagacatcct ggaggaattc ccagaaatca tccctttaca gcaacgtcct  1800
aacacacgta gtagtgagac atctaacgat gaaagcgggg aaacctgctt ttctgggcat  1860
gacgaggagc agattaagct tatgaacgag aactgcattg ttttggattg ggacgataat  1920
gctatcggag cgggtactaa aaaggtttgc catttaatgg agaatattga aaaaggactg  1980
ctgcatcgcg cgttctccgt attcatcttc aatgagcagg gtgaacttct tttgcaacaa  2040
cgcgccaccg aaaagatcac gttcccagat ctttggacca acacgtgttg ctcacatcct  2100
ttgtgtatcg acgatgaact gggattaaag ggtaagttgg acgacaagat taagggagcc  2160
atcacggctg ccgtgcgtaa gcttgaccat gagttgggaa ttcccgaaga tgaaaccaaa  2220
acgcgtggca agttccattt cctgaatcgt atccattaca tggcaccttc caatgaacca  2280
tggggtgagc atgaaatcga ctatatttta ttttacaaga tcaatgcgaa agagaacctt  2340
accgtcaacc cgaatgtgaa tgaggtccgc gatttcaaat gggttagccc aaacgacctg  2400
aaaacgatgt ttgccgatcc cagctacaag tttacaccgt ggtttaagat tatctgcgag  2460
aattacttgt tcaattggtg ggagcagctt gacgacttat cggaagtaga gaatgaccgt  2520
cagatccatc gcatgtta                                                2538

SEQ ID NO: 23          moltype = DNA  length = 2238
```

```
FEATURE              Location/Qualifiers
source               1..2238
                     mol_type = other DNA
                     organism = synthetic construct
SEQUENCE: 23
atgaactcac gtcgttcagc taattatcaa ccaaacctct ggaattttga gtttctgcag  60
agtttggaaa acgaccttaa ggttgagaaa cttgaggaga aggcgacgaa actggaagag  120
gaagttcgct gcatgatcaa tcgtgtggat acacaacctc tgagtttgct tgaactgatt  180
gatgacgtgc agagactcgg actgacgtac aagttcgaaa aagatatcat caaagctctg  240
gagaatatcg tccttctgga tgagaacaag aaaaataagt cagacttgca cgcgacagcg  300
ctgagctttc gtttattaag acaacacggc tttgaagtgt cacaagacgt tttgagcggg  360
ttcaaggata aggagggggg tttcagtggg gaactcaagg gtgacgtgca aggactcctc  420
agtctgtacg aggcgagtta tctcgggttc gagggtgaga atttattaga agaggcacgg  480
actttttcta taacacactt aaaaaataac ttgaaagaag gtataaacac taaagtcgcc  540
gaacaggttt cacatgctct ggagctccct tatcaccaga gactccaccg tctggaggct  600
cgttggttcc tggataaata tgaaccgaag gagccacatc atcaacttct gcttgaattg  660
gctaagttag actttaacat ggttcagaca ctgcaccaga aggaactgca ggacctgtca  720
cgctggtgga ctgagatggg tttagcttcc aagcttgact tcgttcgtga cagactcatg  780
gaggtttatt tttgggcctt gggaatggcg cctgatccgc aatttggtga gtgtcggaaa  840
gcggttacga aaatgttcgg gctggtgacc attatcgacg acgtgtatga tgtttatggg  900
acactggatg aacttcaact ctttacggat gcagtcgaac gctgggatgt gaatgcgata  960
aacaccctcc ctgattacat gaaattgtgc tttttagcgc tctataatac tgttaacgat  1020
acatcctact caatcctcaa agaaaaagga cacaataacc ttagttatct tactaaatct  1080
tggcgcgagc tgtgcaaggc cttcctgcag gaagctaaat ggagtaataa caagataatt  1140
cctgcattta gcaagtactt ggaaaatgca agtgtaagtt cttccggtgt agctttgctc  1200
gccccaagct acttctcagt atgtcaacag caggaggata ttagtgacca tgcgcttcgc  1260
agtttgacgg acttccacgg actcgtccgc tcttcatgcg taattttccg tttgtgcaac  1320
gatctggcca ccagcgcggc cgagttggag cgtggagaaa cgactaatag catcataagc  1380
tatatgcatg aaaatgacgg aacatccgaa gagcaagcac gtgaagagct ccggaagctt  1440
atagacgcag aatggaagaa gatgaaccgg gagcgcgtat cagatagtac cctcttacca  1500
aaggctttta tggaaattgc ggtgaatatg gcgcgcgtat cccattgtac ttaccaatat  1560
ggggacggct tgggacgtcc tgattatgcg acagagaatc ggattaaatt attgttaatc  1620
gacccattcc caatcaatca actgatgtac gtaggaagcg gagaagcagc agcaaaagaa  1680
gcagcagcaa aaatgcaaac ggaacacgtc attttattga atgcacaggg agttcccacg  1740
ggtacgctgg aaaagtatgc cgcacacacg gcagacaccc gcttacatct cgcgttctcc  1800
agttggctgt ttaatgccaa aggacaatta ttagttaccc gccgcgcact gagcaaaaaa  1860
gcatggcctg gcgtgtggac taactcggtt tgtgggcacc cacaactggg agaaagcaac  1920
gaagacgcag tgatccgccg ttgccgttat gagcttggcg tggaaattac gcctcctgaa  1980
tctatctatc ctgactttcg ctaccgcgcc accgatccga gtggcattgt ggaaaatgaa  2040
gtgtgtccgg tatttgccgc acgcaccact agtgcgttac agatcaatga tgatgaagtg  2100
atggattatc aatggtgtga tttagcagat gtattacacg gtattgatgc cacgccgtgg  2160
gcgttcagtc cgtggatggt gatgcaggcg acaaatcgcg aagccagaaa acgattatct  2220
gcatttaccc agcttaaa                                                2238

SEQ ID NO: 24        moltype = DNA  length = 2556
FEATURE              Location/Qualifiers
source               1..2556
                     mol_type = other DNA
                     organism = synthetic construct
SEQUENCE: 24
atgaactcac gtcgttcagc taattatcaa ccaaacctct ggaattttga gtttctgcag  60
agtttggaaa acgaccttaa ggttgagaaa cttgaggaga aggcgacgaa actggaagag  120
gaagttcgct gcatgatcaa tcgtgtggat acacaacctc tgagtttgct tgaactgatt  180
gatgacgtgc agagactcgg actgacgtac aagttcgaaa aagatatcat caaagctctg  240
gagaatatcg tccttctgga tgagaacaag aaaaataagt cagacttgca cgcgacagcg  300
ctgagctttc gtttattaag acaacacggc tttgaagtgt cacaagacgt tttgagcggg  360
ttcaaggata aggagggggg tttcagtggg gaactcaagg gtgacgtgca aggactcctc  420
agtctgtacg aggcgagtta tctcgggttc gagggtgaga atttattaga agaggcacgg  480
actttttcta taacacactt aaaaaataac ttgaaagaag gtataaacac taaagtcgcc  540
gaacaggttt cacatgctct ggagctccct tatcaccaga gactccaccg tctggaggct  600
cgttggttcc tggataaata tgaaccgaag gagccacatc atcaacttct gcttgaattg  660
gctaagttag actttaacat ggttcagaca ctgcaccaga aggaactgca ggacctgtca  720
cgctggtgga ctgagatggg tttagcttcc aagcttgact tcgttcgtga cagactcatg  780
gaggtttatt tttgggcctt gggaatggcg cctgatccgc aatttggtga gtgtcggaaa  840
gcggttacga aaatgttcgg gctggtgacc attatcgacg acgtgtatga tgtttatggg  900
acactggatg aacttcaact ctttacggat gcagtcgaac gctgggatgt gaatgcgata  960
aacaccctcc ctgattacat gaaattgtgc tttttagcgc tctataatac tgttaacgat  1020
acatcctact caatcctcaa agaaaaagga cacaataacc ttagttatct tactaaatct  1080
tggcgcgagc tgtgcaaggc cttcctgcag gaagctaaat ggagtaataa caagataatt  1140
cctgcattta gcaagtactt ggaaaatgca agtgtaagtt cttccggtgt agctttgctc  1200
gccccaagct acttctcagt atgtcaacag caggaggata ttagtgacca tgcgcttcgc  1260
agtttgacgg acttccacgg actcgtccgc tcttcatgcg taattttccg tttgtgcaac  1320
gatctggcca ccagcgcggc cgagttggag cgtggagaaa cgactaatag catcataagc  1380
tatatgcatg aaaatgacgg aacatccgaa gagcaagcac gtgaagagct ccggaagctt  1440
atagacgcag aatggaagaa gatgaaccgg gagcgcgtat cagatagtac cctcttacca  1500
aaggctttta tggaaattgc ggtgaatatg gcgcgcgtat cccattgtac ttaccaatat  1560
ggggacggct tgggacgtcc tgattatgcg acagagaatc ggattaaatt attgttaatc  1620
gacccattcc caatcaatca actgatgtac gtaggaagcg gagaagcagc agcaaaagaa  1680
gcagcagcaa aaatgaccgc cgataataac tctatgcctc acggggctgt atccagctac  1740
```

-continued

```
gcgaaattag tacaaaatca gaccccggaa gacatcctgg aggaattccc agaaatcatc  1800
cctttacagc aacgtcctaa cacacgtagt agtgagacat ctaacgatga aagcggggaa  1860
acctgctttt ctgggcatga cgaggagcag attaagctta tgaacgagaa ctgcattgtt  1920
ttggattggg acgataatgc tatcggagcg ggtactaaaa aggtttgcca tttaatggag  1980
aatattgaaa aggactgct  gcatcgcgcg ttctccgtat tcatcttcaa tgagcagggt  2040
gaacttcttt tgcaacaacg cgccaccgaa aagatcacgt tcccagatct ttggaccaac  2100
acgtgttgct cacatccttt gtgtatcgac gatgaactgg gattaaaggg taagttggac  2160
gacaagatta agggagccat cacggctgcc gtgcgtaagc ttgaccatga gttgggaatt  2220
cccgaagatg aaaccaaaac gcgtggcaag ttccatttcc tgaatcgtat ccattacatg  2280
gcaccttcca atgaaccatg gggtgagcat gaaatcgact atattttatt ttacaagatc  2340
aatgcgaaag agaaccttac cgtcaacccg aatgtgaatg aggtccgcga tttcaaatgg  2400
gttagcccaa acgacctgaa aacgatgttt gccgatccca gctacaagtt tacaccgtgg  2460
tttaagatta tctgcgagaa ttacttgttc aattggtggg agcagcttga cgacttatcg  2520
gaagtagaga atgaccgtca gatccatcgc atgtta                            2556

SEQ ID NO: 25          moltype = AA  length = 544
FEATURE                Location/Qualifiers
source                 1..544
                       mol_type = protein
                       organism = unidentified
SEQUENCE: 25
MEARRSANYE PNSWDYDYLL SSDTDESIEV YKDKAKKLEA EVRREINNEK AEFLTLLELI  60
DNVQRLGLGY RFESDIRGAL DRFVSSGGFD AVTKTSLHGT ALSFRLLRQH GFEVSQEAFS  120
GFKDQNGNFL ENLKEDIKAI LSLYEASFLA LEGENILDEA KVFAISHLKE LSEEKIGKEL  180
AEQVNHALEL PLHRRTQRLE AVWSIEAYRK KEDANQVLLE LAILDYNMIQ SVYQRDLRET  240
SRWWRRVGLA TKLHFARDRL IESFYWAVGV AFEPQYSDCR NSVAKMFCFV TIIDDIYDVY  300
GTLDELELFT DAVERWDVNA INDLPDYMKL CFLALYNTIN EIAYDNLKDK GENILPYLTK  360
AWADLCNAFL QEAKWLYNKS TPTFDDYFGN AWKSSSGPLQ LVFAYFAVVQ NIKKEEIENL  420
QKYHDTISRP SHIFRLCNDL ASASAEIARG ETANSVSCYM RTKGISEELA TESVMNLIDE  480
TWKKMNKEKL SGSLFAKPFV ETAINLARQS HCTYHNGDAH TSPDELTRKR VLSVITEPIL  540
PFER                                                                544

SEQ ID NO: 26          moltype = AA  length = 551
FEATURE                Location/Qualifiers
source                 1..551
                       mol_type = protein
                       organism = unidentified
SEQUENCE: 26
MNSRRSANYQ PNLWNFEFLQ SLENDLKVEK LEEKATKLEE EVRCMINRVD TQPLSLLELI  60
DDVQRLGLTY KFEKDIIKAL ENIVLLDENK KNKSDLHATA LSFRLLRQHG FEVSQDVFER  120
FKDKEGGFSG ELKGDVQGLL SLYEASYLGF EGENLLEEAR TFSITHLKNN LKEGINTKVA  180
EQVSHALELP YHQRLHRLEA RWFLDKYEPK EPHHQLLLEL AKLDFNMVQT LHQKELQDLS  240
RWWTEMGLAS KLDFVRDRLM EVYFWALGMA PDPQFGECRK AVTKMFGLVT IIDDVYDVYG  300
TLDELQLFTD AVERWDVNAI NTLPDYMKLC FLALYNTVND TSYSILKEKG HNNLSYLTKS  360
WRELCKAFLQ EAKWSNNKII PAFSKYLENA SVSSSGVALL APSYFSVCQQ QEDISDHALR  420
SLTDFHGLVR SSCVIFRLCN DLATSAAELE RGETTNSIIS YMHENDGTSE EQAREELRKL  480
IDAEWKKMNR ERVSDSTLLP KAFMEIAVNM ARVSHCTYQY GDGLGRPDYA TENRIKLLLI  540
DPFPINQLMY V                                                        551

SEQ ID NO: 27          moltype = AA  length = 4
FEATURE                Location/Qualifiers
source                 1..4
                       mol_type = protein
                       organism = unidentified
SEQUENCE: 27
GGGS                                                                4

SEQ ID NO: 28          moltype = AA  length = 7
FEATURE                Location/Qualifiers
source                 1..7
                       mol_type = protein
                       organism = unidentified
SEQUENCE: 28
GSGGGGS                                                             7

SEQ ID NO: 29          moltype = AA  length = 13
FEATURE                Location/Qualifiers
source                 1..13
                       mol_type = protein
                       organism = unidentified
SEQUENCE: 29
GSGEAAAKEA AAK                                                      13

SEQ ID NO: 30          moltype = AA  length = 182
FEATURE                Location/Qualifiers
source                 1..182
                       mol_type = protein
                       organism = unidentified
SEQUENCE: 30
```

-continued

```
MQTEHVILLN AQGVPTGTLE KYAAHTADTR LHLAFSSWLF NAKGQLLVTR RALSKKAWPG  60
VWTNSVCGHP QLGESNEDAV IRRCRYELGV EITPPESIYP DFRYRATDPS GIVENEVCPV  120
FAARTTSALQ INDDEVMDYQ WCDLADVLHG IDATPWAFSP WMVMQATNRE ARKRLSAFTQ  180
LK                                                                182

SEQ ID NO: 31          moltype = AA  length = 288
FEATURE                Location/Qualifiers
source                 1..288
                       mol_type = protein
                       organism = unidentified
SEQUENCE: 31
MTADNNSMPH GAVSSYAKLV QNQTPEDILE EFPEIIPLQQ RPNTRSSETS NDESGETCFS  60
GHDEEQIKLM NENCIVLDWD DNAIGAGTKK VCHLMENIEK GLLHRAFSVF IFNEQGELLL  120
QQRATEKITF PDLWTNTCCS HPLCIDDELG LKGKLDDKIK GAITAAVRKL DHELGIPEDE  180
TKTRGKFHFL NRIHYMAPSN EPWGEHEIDY ILFYKINAKE NLTVNPNVNE VRDFKWVSPN  240
DLKTMFADPS YKFTPWFKII CENYLFNWWE QLDDLSEVEN DRQIHRML              288

SEQ ID NO: 32          moltype = DNA  length = 9909
FEATURE                Location/Qualifiers
source                 1..9909
                       mol_type = other DNA
                       organism = synthetic construct
SEQUENCE: 32
aggttccaac tttcaccata atgaaataag atcactaccg ggcgtatttt ttgagttatc  60
gagattttca ggagctaagg aagctaaaat ggagaaaaaa atcactggat ataccaccgt  120
tgatatatcc caatggcatc gtaaagaaca ttttgaggca tttcagtcag ttgctcaatg  180
tacctataac cagaccgttc agctggatat tacggccttt ttaaagaccg taaagaaaaa  240
taagcacaag ttttatccgg cctttattca cattcttgcc cgcctgatga atgctcatcc  300
ggaatttcgt atggcaatga aagacggtga gctggtgata tgggatagtg ttcacccttg  360
ttacaccgtt ttccatgagc aaactgaaac gttttcatcg ctctggagtg aataccacga  420
cgatttccgg cagtttctac acatatattc gcaagatgtg gcgtgttacg gtgaaaacct  480
ggcctatttc cctaaagggt ttattgagaa tatgtttttc gtctcagcca atccctgggt  540
gagtttcacc agttttgatt taaacgtggc caatatggac aacttcttcg cccccgtttt  600
caccatgggc aaatattata cgcaaggcga caaggtgctg atgccgctgg cgattcaggt  660
tcatcatgcc gtttgtgatg gcttccatgt cggcagaatg cttaatgaat tacaacagta  720
ctgcgatgag tggcagggcg gggcgtaatt tgatatcgag ctcgcttgga ctcctgttga  780
tagatccagt aatgacctca gaactccatc tggatttgtt cagaacgctc ggttgccgcc  840
gggcgttttt tattggtgag aatccaagca ctagtaacaa cttatatcgt atggggctga  900
cttcaggtgc tacatttgaa gagataaatt gcactgaaat ctagaaatat tttatctgat  960
taataagatg atcttcttga gatcgttttg gtctgcgcgt aatctcttgc tctgaaaacg  1020
aaaaaaccgc cttgcagggc ggtttttcga aggttctctg agctaccaac tctttgaacc  1080
gaggtaactg gcttggagga gcgcagtcac caaaacttgt cctttcagtt tagccttaac  1140
cggcgcatga cttcaagact aactcctcta aatcaattac cagtggctgc tgccagtggt  1200
gcttttgcat gtctttccgg gttggactca agacgatagt taccggataa ggcgcagcgg  1260
tcggactgaa cggggggttc gtgcatacag tccagcttgg agcgaactgc ctacccggaa  1320
ctgagtgtca ggcgtggaat gagacaaacg cggccataac agcggaatga caccggtaaa  1380
ccgaaaggca ggaacaggag agcgcacgag ggagccgcca gggggaaacg cctggtatct  1440
ttatagtcct gtcgggtttc gccaccactg atttgagcgt cagatttcgt gatgcttgtc  1500
aggggggcgg agcctatgga aaaacggctt tgccgcggcc ctctcacttc cctgttaagt  1560
atcttcctgg catcttccag gaaatctccg ccccgttcgt aagccatttc cgctcgccgc  1620
agtcgaacga ccgagcgtag cgagtcagtg agcgaggaag cggaatatat ccctaggtat  1680
aaacgcagaa aggcccaccc gaaggtgagc cagtgtgact ctagtagaga gcgttcaccg  1740
acaaacaaca gataaaacga aaggcccagt ctttcgactg agcctttcgt tttatttgat  1800
gcctggagat ccttactcga gtttggatcc taatcactta tccagatacg tttccgggtc  1860
cttctccttg cgaacacccc agtcggcctg cgtaacatcc agccattgga ctttgctgaa  1920
acgtttgtcg ttggccgttt gtgcgcgcag atcgacgtcc tgtttcgtga tgacggcaat  1980
ggcgtcgtaa ccacccgcgc ccggaatcag gcacgttaac acgcccttta aggtttgaca  2040
gtcgtccagc agagacgtct ggaccggtgg ttcgatatcc gcgccgctct ccttcgtaat  2100
tttgcggaag ctacggcgaa tcgttgccac ggcatcgcgg acctccgtga tctccgggta  2160
cttctggcag gtgcagtcat tgcgctccag gctctcgaag atttggtcgc tgtagtcgtc  2220
gtgggtttcg tgcaggcggt ccagcttgct cagaccatcc atgaaacggc tattggcgtg  2280
gtccagctcc gtgtaaatct tcaggctttc cggcatgtgg ctgtcgtacc agtttttcac  2340
tttctgcacc agcttaaccg tttcgctgcc gttcttgata tcgcccatcc ataacgttaa  2400
gccgctcggc aggtgattag acttaatggt gatgttccag tcttcttcgt ccaccagatg  2460
cgccagtttg ctaccatacg tcgcagagcc gatgtccggc agattgctga tcagggccgg  2520
cggaaagcgg cgatagcgga tagagccata ggcggccgct gccacatcaa aaccagagcc  2580
aatcttacct tgggcctgac aatgtgccac ctgcgccagg ttatgaatca cttcgcggta  2640
cttgtccacg ttgttctcca ggtcgctcac gaagaagctc gctaacgccg tcgttaagac  2700
ggtaactaaa ccggcgctag aacccagacc cgtcttcggc acctcctcaa tgcgatggct  2760
gtggaagctc aggcggcggt taccacgatg ctccgtaaca gagtcctctt ggctgtggta  2820
cgcgtcgtcg ctgaaaatgt cgatgacgaa caggttgcgg ttgcagtaat cgtccatatt  2880
cggcttgaag tagctgaaga cgttggcaat gaccttctcg ataaatgggt tcttgctgcc  2940
accaatgcta accgggatga agccgctctt tgggctaatg tggtacagcc actcgccgtc  3000
cttgaactgc ttgctcttca cacgcacttc gaacttgtca gagccctgca ggctaccata  3060
cgggtgggca actgcatgca tacgggcaga taagccgacg acgaacgcct cgtacttggt  3120
gtctaacacc aggtagccac cggccagcag tgccttacct ggcgcgctga atgcacgtaa  3180
ttcgctcata tgatctccct cctagatcct taagacgtcc acggcagatt ggtgttaccc  3240
ggcagtaaca ggtcgtcgat ctgctgcttc gtggtcgtct tgttttcgaa cagctggaac  3300
accaggcttt tgatcttcag gtccttgttc agatttttgg cgctcagcag gcaacagccc  3360
```

-continued

```
gtgccgccca ggtccgtctc gaacgtctcg tagctgaagt cgtcctgcag cttcttcttg  3420
aagctgtcga tttgctcctg cgtaatgtca cggcgcagca gcgttaaaga gcagccaccg  3480
ccacctgcac ccgttaattt cgtagagcca atgcgcaggt cgtcgctcag gtttttgatc  3540
agttccaggc ccgggtgaga cacaccgata gaaaccagca ggccgtgatt gatacggatc  3600
agctccagca gctgctcgta cagctcattg ttggtttcca ccgcctcatc gtcggtgccc  3660
ttgcacttgc tcagcttggt catgatctcc agaccctgca gcgcgcactc gcccatcgcg  3720
tccaggatcg gcttcatcac ctccgggaac ttttcggtga ctaaaacacg cacgcgggcg  3780
actaaatcct tggtgctgcg tgggatacgg gtgtaggtca gaatcatcgg gatcgccggg  3840
aagtcgtcca ggaacttgaa gttgttcgtg ttgatcgtgc cgttgtggct gtctttctcg  3900
aacagcaggg cgttgccata cgtggcaact gcgttgtcaa tgccgctcgg ggtgccatga  3960
atgcacttct cgccgataaa ggcccactgg ttcacgatgt gcttgtcgtt ttcgctcagt  4020
ttctccaggt cgttgctgcc aatcaggcca cccagatagg ccatcgccag cgccaggctc  4080
acgctgatag atgcgctaga gcctaagcct gcgccaatcg gcagcgtgct cttcaggctg  4140
aacttgatgt tctttgcgtg cgggcacagg caaacgaaca tgtacaggaa gcagaacgcg  4200
gcgtggtaat ggaagctctc gcttaactgc gctaacagcg ggtccagcag agacaccagc  4260
tcctgagaca gaccgtcggt tgcttgctgg gctttggcca gcttttggct gttcacctgg  4320
tcctccgtga tcgcgttgaa gtcgttgatg ctccacttgt ggttgaagct gatgtccgga  4380
aagtccagct cgatcgtgtc cggtgcagaa gattcgctga tcagcaggta ggtgcgtaac  4440
gcagacacag aggcggcgac ggccggctta ttgtacaccg cagagtgctc gccgaagatg  4500
atcaccttac ctggcgcaga cgtcaggaat ggcagagaca tggttatttc ctcctagatc  4560
ctttagatcc agatcctaat tattgttgtc taatttcttg taaaatatgt tccgctgctt  4620
gtgtatttgc acggggttct tttttcaaag cttcagctac tttagcaatt tcatcacctt  4680
ttgcccctac aacgatagct aatgatttat attgtaaact catatgacct tgttgaatac  4740
cttctgacac aagcgcgcga catgctgcaa agttttgcgc taaaccaacg gcagcaacta  4800
catgacctaa ttcttgtgct gactctacat ttagtagctc taatgaagct ttagcaattg  4860
gtaatacttt tgtaccaccg ccaacgattg ccaatgtcat aggcacttca attgtaccaa  4920
tcaatcgttg acgatcttga tcgtaacgcc atgtagcaat accacgatac tgtccgtcac  4980
gactcgcgta tgcatgcgca cttgcttctg caccacgcgt atcatttcct gttgctaaaa  5040
caacagcatg tatgccattc ataacacctt tattatgtgt tgctgcacga tgaatatcta  5100
cttgggccaa tacagaagca cgttccattc gtttggcaac ctcttctcca gttctctcgc  5160
cccttgctaa atctttaaca tcaatttcgc cttgaacttt aacaacggac gctgttgcat  5220
gattggataa aatactcatt aaaatgtcgc tttgcggaaa ttcatttttt aaaaatgcag  5280
ttatggcctc taaaatcgta ttaagcatat tagcgcccat agcatctttc gtatcaacaa  5340
atacttttaa agatagtaac tgttgctcag gaaatgtatc aatcgctata cgttggtaac  5400
caccaccacg cgctttaata gaaggatatg cctcatccgc aattttatga atttgctttt  5460
ctaaagcttt aatgtctgct gataattttt cagtatcgtc aacgccatca aagacgattt  5520
gacctatcat aatacgttca gaagataccg ttttaaatcc gccagtctga ttcactagct  5580
ttgcaccata actagctgca gcgacaactg aaggctcttc caccatcata ggtacaacat  5640
atgccttatc gtccacaatg atattcggta ataatccaac gggtaatgca ccttgcgcga  5700
tgacattttc aattaaacta ttggctactt cttcatcgat taatggatga ttcagtaaaa  5760
tgtcgaattg ttcttctgat aaccattgct tatcaaccaa ttgttgtaac ttttctttac  5820
gagataaatg tcgaaaattc ttatctaaac tttgcatgga catggtctgt ttcctgaata  5880
gatcctaatt actctggtct gtgatattcg cgaacgttat tttcaatatt tgataagtag  5940
aaaatatgac gatcttcatg aacagcatct tgttcttcgt caaattcaac gtcatcaaaa  6000
cgtttgaaga atgtttcata tgcatcaaca gatacttcag tacggttatt taataatgct  6060
ttatgtgcag cttgatctaa atgatctttg tagccttcaa ctaatgtcgc actataaaat  6120
tcaccaactg aacctgagcc ataactgaat aaaccgattg tttcaccagc ttgtaaatct  6180
cgattttcaa gtaatgatat taggcttaaa tataatgatc cagtataaat attaccgaca  6240
taacggttat aatctacagc atcttcatat cctgaacgta aacgctcttg agttgtttca  6300
tcagcgttat caatgattga ctctaatgcc tttttaccca tttttgtaaa tggaacatgg  6360
aagcatagag atgcgaagtc agctagcgac ttaccttgac gttttgcgta ttcattccag  6420
ctttgttgga atgagcggat ataagcatct ttagataatg caccatcaac taatggatat  6480
ttatgtccag ttggacgcca gaaatcataa acgtcttcag tgtaagcaac agcatcttca  6540
tttaatgcca aaatgcttgg attatgtgca ataaccatcg caactgcgcc agcaccttgt  6600
gttggctcgc cgcctgagtt caatccataa cgtgctgtat ctgtagcaat aactaatact  6660
ttttcattcg gtctagttgc taaataatct ttagctaatt gaattgctgg tgttgcagca  6720
taacaagctt ctttcatttc aaagcagcgt gcaaaaggtt gaatacctaa taagttgtga  6780
atttgaacag cggctgcttt agcagcatca actgctgatt cagttgccac aattaccata  6840
ccaattttct ttttgtcttc gtctgttata atgtccttag cagcgttagc gcccattgaa  6900
acgatgtctt ggtttacagg actaacagcc atttcagttt gaccaattcc aattaaaaat  6960
ttgtttgggt ctacttggcg tgcttctgct aatttagcca tgtctacata gtactttgga  7020
acgtaaaagt ttattttatc gatacctatt gtcataaggt ttctcctgaa tagatcctca  7080
attcaaccgt tcaatcacca tcgcaattcc ctgaccgccg ccaatgcaca gtgttgccag  7140
ccccagcgtt ttatcgcgtg cctgcatggc atgtaatagt gtgaccagaa tacgagcacc  7200
actggcaccg ataggatgcc cgagcgcgat ggccccgccg ttgacattca ctttctcaga  7260
atcaaagccc aggtttttcc caacggcaag gaactgtgca gcaaatgctt cattagcctc  7320
aatgagatca atatccgcca gttgcagccc cgccagttgt aacgcttttt gcgtggcagg  7380
tactggcccc atacccatca atgcgggggg cacgccaccg ctggcataac ttttaatgcg  7440
agccaggggg gtaaggcctg ctgccagcgc cgcagattct tccataatca ccagagcggc  7500
agcaccgtcg ttaataccag acgcgttccc agcggtgact gttcctgctt tatcgaaggc  7560
cgggcgcaat gcacctaacg cttcagccgt tgagttcgct ttcgggaact cgtcttgact  7620
gaagacgaag gttttctttc gagtgacaac atttaccggg acgatttcgg ctgtaaaagc  7680
accggactca attgcggctg ccgctttacg ctgtgaatgt agcgccagtt catcctgcat  7740
ttcacgggta attccgtact ctttagccac gttttcggcg gtaatcccca tatgataacc  7800
atgggtggcg cacatcaggc catcgcgcag gattacgtca taaacctgtc cgtctccaag  7860
acgataacca gagcgtgctt ttgcatcgag taagtagggg gctaaactca tattttccat  7920
acccccgcc acaatgctct gcgcctgacc tgcctgaatg gcctgggcgg caagcgccac  7980
acttttaaga cccgaaccac atactttatt gaccgtgaat ccgcacaccg tttctgccag  8040
cccgcttttt aacagtgcct gacgcgccgg attttgcccc agcccggctt gtaacacgtt  8100
```

-continued

```
acccataatc acttcatcaa cgtgttgtga atcgattttt gcacgttcaa tggcggcttt  8160
aattactgtc gccccaggt cgatggcgct ggtggaagcg agtgaaccgt taaaactacc  8220
gatagcagta cgtaccgcac tgacgatgac acaatttttc attttatatt cctcctaaga  8280
tcttttgaat tctgaaattg ttatccgctc acaattccac acattatacg agccggaagc  8340
ataaagtgta aagcctgggg tgcctaaacg atctcgatcc tctacgccgg acgcatcgtg  8400
gccggcatca ccggcgccac aggtgcggtt gctggcgcct atatcgccga catcaccgat  8460
ggggaagatc gggctcgcca cttcgggctc atgagcgctt gtttcggcgt gggtatggtg  8520
gcaggccccg tggccggggg actgttgggc gccatctcct tgcatgcacc attccttgcg  8580
gcggcggtgc tcaacggcct caacctacta ctgggctgct tcctaatgca ggagtcgcat  8640
aagggagagc gtcgagatcc cggacaccat cgaatggcgc aaaacctttc gcggtatggc  8700
atgatagcgc ccggaagaga gtcaattcag ggtggtgaat gtgaaaccag taacgttata  8760
cgatgtcgca gagtatgccg gtgtctctta tcagaccgtt tcccgcgtgg tgaaccaggc  8820
cagccacgtt tctgcgaaaa cgcgggaaaa agtggaagcg gcgatggcgg agctgaatta  8880
cattcccaac cgcgtggcac aacaactggc gggcaaacag tcgttgctga ttggcgttgc  8940
cacctccagt ctggccctgc acgcgccgtc gcaaattgtc gcggcgatta aatctcgcgc  9000
cgatcaactg ggtgccagcg tggtggtgtc gatggtagaa cgaagcggcg tcgaagcctg  9060
taaagcggcg gtgcacaatc ttctcgcgca acgcgtcagt gggctgatca ttaactatcc  9120
gctggatgac caggatgcca ttgctgtgga agctgcctgc actaatgttc cggcgttatt  9180
tcttgatgtc tctgaccaga cacccatcaa cagtattatt ttctcccatg aagacggtac  9240
gcgactgggc gtggagcatc tggtcgcatt gggtcaccag caaatcgcgc tgttagcggg  9300
cccattaagt tctgtctcgg cgcgtctgcg tctggctggc tggcataaat atctcactcg  9360
caatcaaatt cagccgatag cggaacggga aggcgactgg agtgccatgt ccggttttca  9420
acaaaccatg caaatgctga atgagggcat cgttcccact gcgatgctgg ttgccaacga  9480
tcagatggcg ctgggcgcaa tgcgcgccat taccgagtcc gggctgcgcg ttggtgcgga  9540
catctcggta gtgggatacg acgataccga agacagctca tgttatatcc cgccgttaac  9600
caccatcaaa caggattttc gcctgctggg gcaaaccagc gtggaccgct tgctgcaact  9660
ctctcagggc caggcggtga agggcaatca gctgttgccc gtctcactgg tgaaaagaaa  9720
aaccaccctg gcgcccaata cgcaaaccgc ctctccccgc gcgttggccg attcattaat  9780
gcagctggca cgacaggttt cccgactgga aagcgggcag tgagcgcaac gcaattaatg  9840
taagttagct cactcattag gcaccgacgt cgatatctgg cgaaaatgag acgttgatcg  9900
gcacgtaag                                                          9909

SEQ ID NO: 33          moltype = DNA  length = 7617
FEATURE                Location/Qualifiers
source                 1..7617
                       mol_type = other DNA
                       organism = synthetic construct
SEQUENCE: 33
gctgctgcca gtggcgataa gtcgtgtctt accgggttgg actcaagacg atagttaccg  60
gataaggcgc agcggtcggg ctgaacgggg ggttcgtgca cacagcccag cttggagcga  120
acgacctaca ccgaactgag atacctacag cgtgagctat gagaaagcgc cacgcttccc  180
gaagggagaa aggcggacag gtatccggta agcggcaggg tcggaacagg agagcgcacg  240
agggagcttc caggggaaac gcctggtatc tttatagtcc tgtcgggttt cgccacctct  300
gacttgagcg tcgatttttg tgatgctcgt caggggggcg gagcctatgg aaaaacgcca  360
gcaacgcggc ctttttacgg ttcctggcct tttgctggcc ttttgctcac atgttctttc  420
ctgcgttatc ccctgattct gtggataacc gtattaccgc ctttgagtga gctgataccg  480
ctcgccgcag ccgaacgacc gagcgcagcg agtcagtgag cgaggaagcg gaagagcgcc  540
tgatgcggta ttttctcctt acgcatctgt gcggtatttc acaccgcata tggtgcactc  600
tcagtacaat ctgctctgat gccgcatagt taagccagta tacactccgc tatcgctacg  660
tgactgggtc atggctgcgc cccgacaccc gccaacaccc gctgacgcgc cctgacgggc  720
ttgtctgctc ccggcatccg cttacagaca agctgtgacc gtctccggga gctgcatgtg  780
tcagaggttt tcaccgtcat caccgaaacg cgcgaggcag cagatcaatt cgcgcgcgaa  840
ggcgaagcgg catgcattta cgttgacacc atcgaatggt gcaaaacctt tcgcggtatg  900
gcatgatagc gcccggaaga gagtcaattc agggtggtga atgtgaaacc agtaacgtta  960
tacgatgtcg cagagtatgc cggtgtctct tatcagaccg tttcccgcgt ggtgaaccag  1020
gccagccacg tttctgcgaa aacgcgggaa aaagtggaag cggcgatggc ggagctgaat  1080
tacattccca accgcgtggc acaacaactg gcgggcaaac agtcgttgct gattggcgtt  1140
gccacctcca gtctggccct gcacgcgccg tcgcaaattg tcgcggcgat taaatctcgc  1200
gccgatcaac tgggtgccag cgtggtggtg tcgatggtag aacgaagcgg cgtcgaagcc  1260
tgtaaagcgg cggtgcacaa tcttctcgcg caacgcgtca gtgggctgat cattaactat  1320
ccgctggatg accaggatgc cattgctgtg gaagctgcct gcactaatgt tccggcgtta  1380
tttcttgatg tctctgacca gacacccatc aacagtatta ttttctccca tgaagacggt  1440
acgcgactgg gcgtggagca tctggtcgca ttgggtcacc agcaaatcgc gctgttagcg  1500
ggcccattaa gttctgtctc ggcgcgtctg cgtctggctg gctggcataa atatctcact  1560
cgcaatcaaa ttcagccgat agcggaacgg gaaggcgact ggagtgccat gtccggtttt  1620
caacaaacca tgcaaatgct gaatgagggc atcgttccca ctgcgatgct ggttgccaac  1680
gatcagatgg cgctgggcgc aatgcgcgcc attaccgagt ccgggctgcg cgttggtgcg  1740
gatatctcgg tagtgggata cgacgatacc gaagacagct catgttatat cccgccgtta  1800
accaccatca aacaggattt tcgcctgctg gggcaaacca gcgtggaccg cttgctgcaa  1860
ctctctcagg gccaggcggt gaagggcaat cagctgttgc ccgtctcact ggtgaaaaga  1920
aaaaccaccc tggcgcccaa tacgcaaacc gcctctcccc gcgcgttggc cgattcatta  1980
atgcagctgg cacgacaggt ttcccgactg gaaagcgggc agtgagcgca acgcaattaa  2040
tgtaagttag cgcgaattga tctggtttga cagcttatca tcgactgcac ggtgcaccaa  2100
tgcttctggc gtcaggcagc catcggaagc tgtggtatgg ctgtgcaggt cgtaaatcac  2160
tgcataattc gtgtcgctca aggcgcactc ccgttctgga taatgttttt tgcgccgaca  2220
tcataacggt tctggcaaat attctgaaat gagctgttga caattaatca tccggctcgt  2280
ataatgtgtg gaattgtgag cggataacaa tttcacacag gaaacagacc atgggaattc  2340
aaaagatctt ttaagaagga gatatacata tgcaaacgga acacgtcatt ttattgaatg  2400
cacagggagt tcccacgggt acgctggaaa agtatgccgc acacacggca gacacccgct  2460
```

-continued

```
tacatctcgc gttctccagt tggctgttta atgccaaagg acaattatta gttacccgcc  2520
gcgcactgag caaaaaagca tggcctggcg tgtggactaa ctcggtttgt gggcacccac  2580
aactgggaga aagcaacgaa gacgcagtga tccgccgttg ccgttatgag cttggcgtgg  2640
aaattacgcc tcctgaatct atctatcctg actttcgcta ccgcgccacc gatccgagtg  2700
gcattgtgga aaatgaagtg tgtccggtat ttgccgcacg caccactagt gcgttacaga  2760
tcaatgatga tgaagtgatg gattatcaat ggtgtgattt agcagatgta ttacacggta  2820
ttgatgccac gccgtgggcg ttcagtccgt ggatggtgat gcaggcgaca aatcgcgaag  2880
ccagaaaacg attatctgca tttacccagc ttaaataaca gaatttaaaa ctaatacgcg  2940
ggaggttttt tatggaagct cgtcgttctg cgaactacga acctaacagc tgggactatg  3000
attacctgct gtcctccgac acggacgagt ccatcgaagt atacaaagac aaagcgaaaa  3060
agctggaagc cgaagttcgt cgcgagatta ataacgaaaa agcagaattt ctgaccctgc  3120
tggaactgat tgacaacgtc cagcgcctgg gcctgggtta ccgtttcgag tctgatatcc  3180
gtggtgcgct ggatcgcttc gtttcctccg gcggcttcga tgcggtaacc aagacttccc  3240
tgcacggtac ggcactgtct ttccgtctgc tgcgtcaaca cggttttgag gtttctcagg  3300
aagcgttcag cggcttcaaa gaccaaaacg gcaacttcct ggagaacctg aaggaagata  3360
tcaaagctat cctgagcctg tacgaggcca gcttcctggc tctggaaggc gaaaacatcc  3420
tggacgaggc gaaggtttc gcaatctctc atctgaaaga actgtctgaa gaaaagatcg  3480
gtaaagagct ggcagaacag gtgaaccatg cactggaact gccactgcat cgccgtactc  3540
agcgtctgga agcagtatgg tctatcgagg cctaccgtaa aaaggaggac gcgaatcagg  3600
ttctgctgga gctggcaatt ctggattaca acatgatcca gtctgtatac cagcgtgatc  3660
tgcgtgaaac gtcccgttgg tggcgtcgtg tgggtctggc gaccaaactg cactttgctc  3720
gtgaccgcct gattgagagc ttctactggg ccgtgggtgt agcattcgaa ccgcaatact  3780
ccgactgccg taactccgtc gcaaaaatgt tttgtttcgt aaccattatc gacgatatct  3840
acgatgtata cggcaccctg gacgaactgg agctgtttac tgatgcagtt gagcgttggg  3900
acgtaaacgc catcaacgac ctgccggatt acatgaaact gtgctttctg gctctgtata  3960
acactattaa cgaaatcgcc tacgacaacc tgaaagataa aggtgagaac atcctgccgt  4020
atctgaccaa agcctgggct gacctgtgca acgctttcct gcaagaagcc aagtggctgt  4080
acaacaaatc tactccgacc tttgacgact acttcggcaa cgcatggaaa tcctcttctg  4140
gcccgctgca actggtgttc gcttacttcg ctgtcgtgca gaacattaaa aaggaagaga  4200
tcgaaaacct gcaaaaatac catgacacca tctctcgtcc ttcccatatc ttccgtctgt  4260
gcaatgacct ggctagcgcg tctgcggaaa ttgcgcgtgg tgaaaccgca aatagcgttt  4320
cttgttacat gcgcactaaa ggtatctccg aagaactggc taccgaaagc gtgatgaatc  4380
tgatcgatga aacctggaaa aagatgaaca aggaaaaact gagtggtagc ctgttcgcga  4440
aaccgttcgt ggaaaccgcg atcaacctgg cacgtcaatc tcactgcact tatcataacg  4500
gcgacgcgca tacctctccg gatgagctga cccgcaaacg cgttctgtct gtaatcactg  4560
aaccgattct gccgtttgaa cgctaaggat ccaaactcga gttcggatct aggaggatta  4620
tgagatgacc gtttacacag catccgttac cgcacccgtc aacatcgcaa cccttaagta  4680
ttgggggaaa agggacacga agttgaatct gcccaccaat tcgtccatat cagtgacttt  4740
atcgcaagat gacctcagaa cgttgacctc tgcggctact gcacctgagt ttgaacgcga  4800
cactttgtgg ttaaatggag aaccacacag catcgacaat gaaagaactc aaaattgtct  4860
gcgcgaccta cgccaattaa gaaaggaaat ggaatcgaag gacgcctcat tgcccacatt  4920
atctcaatgg aaactccaca ttgtctccga aaataacttt cctacagcag ctggtttagc  4980
ttcctccgct gctggctttg ctgcattggt ctctgcaatt gctaagttat accaattacc  5040
acagtcaact tcagaaatat ctagaatagc aagaaagggg tctggttcag cttgtagatc  5100
gttgtttggc ggatacgtgg cctgggaaat gggaaaagct gaagatggtc atgattccat  5160
ggcagtacaa atcgcagaca gctctgactg gcctcagatg aaagcttgtg tcctagttgt  5220
cagcgatatt aaaaaggatg tgagttccac tcagggtatg caattgaccg tggcaacctc  5280
cgaactattt aaagaaagaa ttgaacatgt cgtaccaaag agatttgaag tcatgcgtaa  5340
agccattgtt gaaaaagatt tcgccacctt tgcaaaggaa acaatgatgg attccaactc  5400
tttccatgcc acatgtttgg actctttccc tccaatattc tacatgaatg acacttccaa  5460
gcgtatcatc agttggtgcc acaccattaa tcagttttac ggagaaacaa tcgttgcata  5520
cacgtttgat gcaggtccaa atgctgtgtt gtactactta gctgaaaatg agtcgaaact  5580
ctttgcattt atctataaat tgtttggctc tgttcctgga tgggacaaga aatttactac  5640
tgagcagctt gaggctttca accatcaatt tgaatcatct aactttactg cacgtgaatt  5700
ggatcttgag ttgcaaaagg atgttgccag agtgatttta actcaagtcg gttcaggccc  5760
acaagaaaca aacgaatctt tgattgacgc aaagactggt ctaccaaagg aataactgca  5820
ggcatgcaag cttggctgtt ttggcggatg agagaagatt ttcagcctga tacagattaa  5880
atcagaacgc agaagcggtc tgataaaaca gaatttgcct ggcggcagta gcgcggtggt  5940
cccacctgac cccatgccga actcagaagt gaaacgccgt agcgccgatg gtagtgtggg  6000
gtctccccat gcgagagtag ggaactgcca ggcatcaaat aaaacgaaag gctcagtcga  6060
aagactgggc ctttcgtttt atctgttgtt tgtcggtgaa cgctctcctg agtaggacaa  6120
atccgccggg agcggatttg aacgttgcga agcaacggcc cggagggtgg cgggcaggac  6180
gcccgccata aactgccagg catcaaatta agcagaaggc catcctgacg gatggccttt  6240
ttgcgtttct acaaactctt ttgtttattt ttctaaatac attcaaatat gtatccgctc  6300
atgagacaat aaccctgata aatgcttcaa taatattgaa aaaggaagag tatgagtatt  6360
caacatttcc gtgtcgccct tattcccttt tttgcggcat tttgccttcc tgtttttgct  6420
cacccagaaa cgctggtgaa agtaaaagat gctgaagatc agttgggtgc acgagtgggt  6480
tacatcgaac tggatctcaa cagcggtaag atccttgaga gttttcgccc cgaagaacgt  6540
tttccaatga tgagcacttt taaagttctg ctatgtggcg cggtattatc ccgtgttgac  6600
gccgggcaag agcaactcgg tcgccgcata cactattctc agaatgactt ggttgagtac  6660
tcaccagtca cagaaaagca tcttacggat ggcatgacag taagagaatt atgcagtgct  6720
gccataacca tgagtgataa cactgcggcc aacttacttc tgacaacgat cggaggaccg  6780
aaggagctaa ccgctttttt gcacaacatg ggggatcatg taactcgcct tgatcgttgg  6840
gaaccggagc tgaatgaagc cataccaaac gacgagcgtg acaccacgat gcctgtagca  6900
atggcaacaa cgttgcgcaa actattaact ggcgaactac ttactctagc ttcccggcaa  6960
caattaatag actggatgga ggcggataaa gttgcaggac cacttctgcg ctcggccctt  7020
ccggctggct ggtttattgc tgataaatct ggagccggtg agcgtgggtc tcgcggtatc  7080
attgcagcac tggggccaga tggtaagccc tcccgtatcg tagttatcta cacgacgggg  7140
agtcaggcaa ctatggatga acgaaataga cagatcgctg agataggtgc ctcactgatt  7200
```

-continued

```
aagcattggt aactgtcaga ccaagtttac tcatatatac tttagattga tttaaaactt  7260
catttttaat ttaaaaggat ctaggtgaag atcctttttg ataatctcat gaccaaaatc  7320
ccttaacgtg agttttcgtt ccactgagcg tcagaccccg tagaaaagat caaaggatct  7380
tcttgagatc cttttttctt gcgcgtaatc tgctgcttgc aaacaaaaaa accaccgcta  7440
ccagcggtgg tttgtttgcc ggatcaagag ctaccaactc tttttccgaa ggtaactggc  7500
ttcagcagag cgcagatacc aaatactgtc cttctagtgt agccgtagtt aggccaccac  7560
ttcaagaact ctgtagcacc gcctacatac ctcgctctgc taatcctgtt accagtg     7617

SEQ ID NO: 34          moltype = DNA  length = 7528
FEATURE                Location/Qualifiers
source                 1..7528
                       mol_type = other DNA
                       organism = synthetic construct
SEQUENCE: 34
aacagaattt gcctggcggc agtagcgcgg tggtcccacc tgaccccatg ccgaactcag  60
aagtgaaacg ccgtagcgcc gatggtagtg tggggtctgc cccatgcgaga gtagggaact  120
gccaggcatc aaataaaacg aaaggctcag tcgaaagact gggcctttcg ttttatctgt  180
tgtttgtcgg tgaacgctct cctgagtagg acaaatccgc cgggagcgga tttgaacgtt  240
gcgaagcaac ggcccggagg gtggcgggca ggacgcccgc cataaactgc caggcatcaa  300
attaagcaga aggccatcct gacggatggc ctttttgcgt ttctacaaac tctttttgtt  360
tatttttcta aatacattca aatatgtatc cgctcatgag acaataaccc tgataaatgc  420
ttcaataata ttgaaaaagg aagagtatga gtattcaaca tttccgtgtc gcccttattc  480
ccttttttgc ggcattttgc cttcctgttt ttgctcaccc agaaacgctg gtgaaagtaa  540
aagatgctga agatcagttg ggtgcacgag tgggttacat cgaactggat ctcaacagcg  600
gtaagatcct tgagagtttt cgccccgaag aacgttttcc aatgatgagc acttttaaag  660
ttctgctatg tggcgcggta ttatcccgtg ttgacgccgg gcaagagcaa ctcggtcgcc  720
gcatacacta ttctcagaat gacttggttg agtactcacc agtcacagaa aagcatctta  780
cggatggcat gacagtaaga gaattatgca gtgctgccat aaccatgagt gataacactg  840
cggccaactt acttctgaca acgatcggag gaccgaagga gctaaccgct tttttgcaca  900
acatggggga tcatgtaact cgccttgatc gttgggaacc ggagctgaat gaagccatac  960
caaacgacga gcgtgacacc acgatgccta cagcaatggc aacaacgttg cgcaaactat  1020
taactggcga actacttact ctagcttccc ggcaacaatt aatagactgg atggaggcgg  1080
ataaagttgc aggaccactt ctgcgctcgg cccttccggc tggctggttt attgctgata  1140
aatctggagc cggtgagcgt gggtcacgcg gtatcattgc agcactgggg ccagatggta  1200
agccctcccg tatcgtagtt atctacacga cggggagtca ggcaactatg gatgaacgaa  1260
atagacagat cgctgagata ggtgcctcac tgattaagca ttggtaactg tcagaccaag  1320
tttactcata tatactttag attgatttaa aacttcattt ttaatttaaa aggatctagg  1380
tgaagatcct ttttgataat ctcatgacca aaatccctta acgtgagttt tcgttccact  1440
gagcgtcaga ccccgtagaa aagatcaaag gatcttcttg agatcctttt tttctgcgcg  1500
taatctgctg cttgcaaaca aaaaaaccac cgctaccagc ggtggtttgt ttgccggatc  1560
aagagctacc aactcttttt ccgaaggtaa ctggcttcag cagagcgcag ataccaaata  1620
ctgtccttct agtgtagccg tagttaggcc accacttcaa gaactctgta gcaccgccta  1680
catacctcgc tctgctaatc ctgttaccag tggctgctgc cagtggcgat aagtcgtgtc  1740
ttaccgggtt ggactcaaga cgatagttac cggataaggc gcagcggtcg ggctgaacgg  1800
ggggttcgtg cacacagccc agcttggagc gaacgaccta caccgaactg agatacctac  1860
agcgtgagct atgagaaagc gccacgcttc ccgaagggag aaaggcggac aggtatccgg  1920
taagcggcag ggtcggaaca ggagagcgca cgagggagct tccaggggga aacgcctggt  1980
atctttatag tcctgtcggg tttcgccacc tctgacttga gcgtcgattt ttgtgatgct  2040
cgtcaggggg gcggagccta tggaaaaacg ccagcaacgc ggccttttta cggttcctgg  2100
ccttttgctg gccttttgct cacatgttct ttcctgcgtt atcccctgat tctgtggata  2160
accgtattac cgcctttgag tgagctgata ccgctcgccg cagccgaacg accgagcgca  2220
gcgagtcagt gagcgaggaa gcggaagagc gcctgatgcg gtattttctc cttacgcatc  2280
tgtgcggtat ttcacaccgc atatggtgca ctctcagtac aatctgctct gatgccgcat  2340
agttaagcca gtatacactc cgctatcgct acgtgactgg gtcatggctg cgccccgaca  2400
cccgccaaca cccgctgacg cgccctgacg ggcttgtctg ctcccggcat ccgcttacag  2460
acaagctgtg accgtgtccg ggagctgcat gtgtcagagg ttttcaccgt catcaccgaa  2520
acgcgcgagg cagcagatca attcgcgcgc gaaggcgaag cggcatgcat ttacgttgac  2580
accatcgaat ggtgcaaaac ctttcgcggt atggcatgat agcgcccgga agagagtcaa  2640
ttcagggtgg tgaatgtgaa accagtaacg ttatacgatg tcgcagagta tgccggtgtc  2700
tcttatcaga ccgtttcccg cgtggtgaac caggccagcc acgtttctgc gaaaacgcgg  2760
gaaaaagtgg aagcggcgat ggcggagctg aattacattc ccaaccgcgt ggcacaacaa  2820
ctggcgggca aacagtcgtt gctgattggc gttgccacct ccagtctggc cctgcacgcg  2880
ccgtcgcaaa ttgtcgcggc gattaaatct cgcgccgatc aactgggtgc cagcgtggtg  2940
gtgtcgatgg tagaacgaag cggcgtcgaa gcctgtaaag cggcggtgca caatcttctc  3000
gcgcaacgcg tcagtgggct gatcattaac tatccgctgg atgaccagga tgccattgct  3060
gtggaagctg cctgcactaa tgttccggcg ttatttcttg atgtctctga ccagacaccc  3120
atcaacagta ttattttctc ccatgaagac ggtacgcgac tgggcgtgga gcatctggtc  3180
gcattgggtc accagcaaat cgcgctgtta gcgggcccat taagttctgt ctcggcgcgt  3240
ctgcgtctgg ctggctggca taaatatctc actcgcaatc aaattcagcc gatagcggaa  3300
cgggaaggcg actggagtgc catgtccggt tttcaacaaa ccatgcaaat gctgaatgag  3360
ggcatcgttc ccactgcgat gctggttgcc aacgatcaga tggcgctggg cgcaatgcgc  3420
gccattaccg agtccgggct gcgcgttggt gcggatatct cggtagtggg atacgacgat  3480
accgaagaca gctcatgtta tatcccgccg tcaaccacca tcaaacagga ttttcgcctg  3540
ctggggcaaa ccagcgtgga ccgcttgctg caactctctc agggccaggc ggtgaagggc  3600
aatcagctgt tgcccgtgtc actggtgaaa agaaaaacca ccctggcgcc caatacgcaa  3660
accgcctctc cccgcgcgtt ggccgattca ttaatgcagc tggcacgaca ggtttcccga  3720
ctggaaagcg ggcagtgagc gcaacgcaat taatgtgagt tagcgcgaat tgatctggtt  3780
tgacagctta tcatcgactg cacggtgcac caatgcttct ggcgtcaggc agccatcgga  3840
agctgtggta tggctgtgca ggtcgtaaat cactgcataa ttcgtgtcgc tcaaggcgca  3900
```

-continued

```
ctcccgttct ggataatgtt ttttgcgccg acatcataac ggttctggca aatattctga  3960
aatgagctgt tgacaattaa tcatccggct cgtataatgt gtggaattgt gagcggataa  4020
caatttcaca caggaaacag accatgggaa ttcaaaagat cttttaagaa ggagatatac  4080
atatgcaaac ggaacacgtc attttattga atgcacaggg agttcccacg ggtacgctgg  4140
aaaagtatgc cgcacacacg gcagacaccc gcttacatct cgcgttctcc agttggctgt  4200
ttaatgccaa aggacaatta ttagttaccc gccgcgcact gagcaaaaaa gcatggcctg  4260
gcgtgtggac taactcggtt tgtgggcacc cacaactggg agaaagcaac gaagacgcag  4320
tgatccgccg ttgccgttat gagcttggcg tggaaattac gcctcctgaa tctatctatc  4380
ctgactttcg ctaccgcgcc accgatccga gtggcattgt ggaaaatgaa gtgtgtccgg  4440
tatttgccgc acgcaccact agtgcgttac agatcaatga tgatgaagtg atggattatc  4500
aatggtgtga tttagcagat gtattacacg gtattgatgc cacgccgtgg gcgttcagtc  4560
cgtggatggt gatgcaggcg acaaatcgcg aagccagaaa acgattatct gcatttaccc  4620
agcttaaata acagaattta aaactaatac gcgggaggtt ttttatggaa gctcgtcgtt  4680
ctgcgaacta cgaacctaac agctgggact atgattacct gctgtcctcc gacacggacg  4740
agtccatcga agtatacaaa gacaaagcga aaaagctgga agccgaagtt cgtcgcgaga  4800
ttaataacga aaaagcagaa tttctgaccc tgctggaact gattgacaac gtccagcgcc  4860
tgggcctggg ttaccgtttc gagtctgata tccgtggtgc gctggatcgc ttcgtttcct  4920
ccggcggctt cgatgcggta accaagactt ccctgcacgg tacggcactg tctttccgtc  4980
tgctgcgtca acacggtttt gaggtttctc aggaagcgtt cagcggcttc aaagaccaaa  5040
acggcaactt cctggagaac ctgaaggaag atatcaaagc tatcctgagc ctgtacgagg  5100
ccagcttcct ggctctggaa ggcgaaaaca tcctggacga ggcgaaggtt ttcgcaatct  5160
ctcatctgaa agaactgtct gaagaaaaga tcggtaaaga gctggcagaa caggtgaacc  5220
atgcactgga actgccactg catcgccgta ctcagcgtct ggaagcagta tggtctatcg  5280
aggcctaccg taaaaaggag gacgcgaatc aggttctgct ggagctggca attctggatt  5340
acaacatgat ccagtctgta taccagcgtg atctgcgtga aacgtcccgt tggtggcgtc  5400
gtgtgggtct ggcgaccaaa ctgcactttg ctcgtgaccg cctgattgag agcttctact  5460
gggccgtggg tgtagcattc gaaccgcaat actccgactg ccgtaactcc gtcgcaaaaa  5520
tgttttgttt cgtaaccatt atcgacgata tctacgatgt atacggcacc ctggacgaac  5580
tggagctgtt tactgatgca gttgagcgtt gggacgtaaa cgccatcaac gacctgccgg  5640
attacatgaa actgtgcttt ctggctctgt ataacactat taacgaaatc gcctacgaca  5700
acctgaaaga taaaggtgag aacatcctgc cgtatctgac caaagcctgg gctgacctgt  5760
gcaacgcttt cctgcaagaa gccaagtggc tgtacaacaa atctactccg acctttgacg  5820
actacttcgg caacgcatgg aaatcctctt ctggcccgct gcaactggtg ttcgcttact  5880
tcgctgtcgt gcagaacatt aaaaaggaag agatcgaaaa cctgcaaaaa taccatgaca  5940
ccatctctcg tccttcccat atcttccgtc tgtgcaatga cctggctagc gcgtctgcgg  6000
aaattgcgcg tggtgaaacc gcaaatagcg tttcttgtta catgcgcact aaaggtatct  6060
ccgaagaact ggctaccgaa agcgtgatga atctgatcga tgaaacctgg aaaaagatga  6120
acaaggaaaa actgagtggt agcctgttcg cgaaaccgtt cgtggaaacc gcgatcaacc  6180
tggcacgtca atctcactgc acttatcata acggcgacgc gcatacctct ccggatgagc  6240
tgacccgcaa acgcgttctg tctgtaatca ctgaaccgat tctgccgttt gaacgctaag  6300
gatccaaact cgagttcgga tctaggagga ttatgagatg accgtttaca cagcatccgt  6360
taccgcaccc gtcaacatcg caacccttaa gtattggggg aaaagggaca cgaagttgaa  6420
tctgcccacc aattcgtcca tatcagtgac tttatcgcaa gatgacctca gaacgttgac  6480
ctctgcggct actgcacctg agtttgaacg cgacactttg tggttaaatg gagaaccaca  6540
cagcatcgac aatgaaagaa ctcaaaattg tctgcgcgac ctacgccaat taagaaagga  6600
aatggaatcg aaggacgcct cattgcccac attatctcaa tggaaactcc acattgtctc  6660
cgaaaataac tttcctacag cagctggttt agcttcctcc gctgctggct ttgctgcatt  6720
ggtatctgca attgccaagt tataccaatt accacagtca acttcagaaa tatctagaat  6780
agcaagaaag gggtctggtt cagcttgtag atcgttgttt ggcggatacg tggcctggga  6840
aatgggaaaa gctgaagatg gtcatgattc catggcagta caaatcgcag acagctctga  6900
ctggcctcag atgaaagctt gtgtcctagt tgtcagcgat attaaaaagg atgtgagttc  6960
cactcagggt atgcaattga ccgtggcaac ctccgaacta tttaaagaaa gaattgaaca  7020
tgtcgtacca aagagatttg aagtcatgcg taaagccatt gttgaaaaag atttcgccac  7080
ctttgcaaag gaaacaatga tggattccaa ctctttccat gccacatgtt tggactcttt  7140
ccctccaata ttctacatga atgacacttc caagcgtatc atcagttggt gccacaccat  7200
taatcagttt tacggagaaa caatcgttgc atacacgttt gatgcaggtc caaatgctgt  7260
gttgtactac ttagctgaaa atgagtcgaa actctttgca tttatctata aattgtttgg  7320
ctctgttcct ggatgggaca agaaatttac tactgagcag cttgaggctt tcaaccatca  7380
atttgaatca tctaacttta ctgcacgtga attggatctt gagttgcaaa aggatgttgc  7440
cagagtgatt ttaactcaag tcggttcagg cccacaagaa acaaacgaat ctttgattga  7500
cgcaaagact ggtctaccaa aggaataa                                    7528
```